US006783956B2

(12) United States Patent
Ish-Horowicz et al.

(10) Patent No.: US 6,783,956 B2
(45) Date of Patent: Aug. 31, 2004

(54) NUCLEOTIDE AND PROTEIN SEQUENCES OF VERTEBRATE DELTA GENES AND METHODS BASED THEREON

(75) Inventors: David Ish-Horowicz, Oxford (GB); Domingos Manuel Pinto Henrique, Queijas (PT); Julian Hart Lewis, Oxford (GB); Spyridon Artavanis-Tsakonas, Hamden, CT (US); Grace E. Gray, New Haven, CT (US)

(73) Assignees: Yale University, Hew Haven, CT (US); Imperial Cancer Research Technology, Ltd., London (GB)

( * ) Notice: Subject to any disclaimer, the term of this patent is extended or adjusted under 35 U.S.C. 154(b) by 0 days.

(21) Appl. No.: 09/908,322

(22) Filed: Jul. 17, 2001

(65) Prior Publication Data

US 2002/0107194 A1 Aug. 8, 2002

Related U.S. Application Data

(62) Division of application No. 08/981,392, filed as application No. PCT/US96/11178 on Jun. 28, 1996, now Pat. No. 6,262,025.
(60) Provisional application No. 60/000,589, filed on Jun. 28, 1995.

(51) Int. Cl.[7] .............................................. C12P 21/06
(52) U.S. Cl. .................................................... 435/69.1
(58) Field of Search ....................... 435/69.1; 530/300, 530/350; 536/23.1

(56) References Cited

U.S. PATENT DOCUMENTS

| | | | |
|---|---|---|---|
| 5,637,471 A | 6/1997 | Artavanis-Tsakonas et al. | |
| 5,648,464 A | 7/1997 | Artavanis-Tsakonas et al. | |
| 5,750,652 A | 5/1998 | Artavanis-Tsakonas et al. | |
| 5,780,300 A | 7/1998 | Artavanis-Tsakonas et al. | |
| 5,786,158 A | 7/1998 | Artavanis-Tsakonas et al. | |
| 5,789,195 A | 8/1998 | Artavanis-Tsakonas et al. | |
| 5,849,869 A | 12/1998 | Artavanis-Tsakonas et al. | |
| 5,856,441 A | 1/1999 | Artavanis-Tsakonas et al. | |
| 5,869,282 A | 2/1999 | Ish-Horowicz et al. | |
| 6,004,924 A | 12/1999 | Ish-Horowicz et al. | |
| 6,083,904 A | 7/2000 | Artavanis-Tsakonas et al. | |
| 6,090,922 A | 7/2000 | Artavanis-Tsakonas et al. | |
| 6,149,902 A | 11/2000 | Artavanis-Tsakonas et al. | |
| 2002/0010137 A1 * | 1/2002 | Ashkenazi et al. ............ | 514/12 |

FOREIGN PATENT DOCUMENTS

| | | |
|---|---|---|
| EP | 0 861 894 | 9/1998 |
| WO | WO 92/19734 | 11/1992 |
| WO | WO 93/12141 | 6/1993 |
| WO | WO 94/07474 | 4/1994 |
| WO | WO 96/27610 | 9/1996 |
| WO | WO 97/01571 | 1/1997 |
| WO | WO 97/11716 | 4/1997 |
| WO | WO 97/18822 | 5/1997 |
| WO | WO 97/19172 | 5/1997 |
| WO | WO 97/45143 | 12/1997 |
| WO | WO 98/17793 | 4/1998 |
| WO | WO 98/20142 | 5/1998 |
| WO | WO 98/45434 | 10/1998 |
| WO | WO 98/51799 | 11/1998 |
| WO | WO 00/02897 | 1/2000 |

OTHER PUBLICATIONS

Henderson ST, Gao D, Lambie EJ, Kimble J. lag–2 may encode a signaling ligand for the GLP–1 and LIN–12 receptors of C. elegans. Development. Oct. 1994;120(10):2913–24.*
U.S. patent application Ser. No. 09/195,524, Artavanis–Tsakonas et al., filed Nov. 19, 1998.
U.S. patent application Ser. No. 09/121,457, Artavanis–Tsakonas et al., filed Jul. 23, 1998.
U.S. patent application Ser. No. 09/113,824, Artavanis–Tsakonas et al., filed Jul. 10, 1998.
U.S. patent application Ser. No. 09/113,399, Artavanis–Tsakonas et al., filed Jul. 10, 1998.
U.S. patent application Ser. No. 09/043,847, Artavanis–Tsakonas et al., filed Jun. 1, 1998.
U.S. patent application Ser. No. 08/947,956, Artavanis–Tsakonas et al., filed Oct. 9, 1997.
U.S. patent application Ser. No. 08/937,132, Artavanis–Tsakonas et al., filed Sep. 24, 1997.
U.S. patent application Ser. No. 08/899,232, Artavanis–Tsakonas et al., filed Jul. 23, 1997.
U.S. patent application Ser. No. 08/561,963, Artavanis–Tsakonas et al., filed Nov. 22, 1995.
U.S. patent application Ser. No. 09/908,322, Ish–Horowicz et al., filed Jul. 17, 2001.
U.S. patent application Ser. No. 09/352,585, Ish–Horowicz et al., filed Jul. 13, 1999.

(List continued on next page.)

*Primary Examiner*—Karen Cochrane Carlson
*Assistant Examiner*—Sheridan K Snedden
(74) *Attorney, Agent, or Firm*—Jones Day

(57) ABSTRACT

The present invention relates to nucleotide sequences of vertebrate Delta genes, and amino acid sequences of their encoded proteins, as well as derivatives (e.g., fragments) and analogs thereof. In a specific embodiment, the vertebrate Delta protein is a human protein. The invention further relates to fragments (and derivatives and analogs thereof) of Delta which comprise one or more domains of the Delta protein, including but not limited to the intracellular domain, extracellular domain, DSL domain, domain amino-terminal to the DSL domain, transmembrane region, or one or more EGF-like repeats of a Delta protein, or any combination of the foregoing. Antibodies to Delta, its derivatives and analogs, are additionally provided. Methods of production of the Delta proteins, derivatives and analogs, e.g., by recombinant means, are also provided. Therapeutic and diagnostic methods and pharmaceutical compositions are provided. In specific examples, isolated Delta genes, from Xenopus, chick, mouse, and human, are provided.

67 Claims, 40 Drawing Sheets-

OTHER PUBLICATIONS

Apella et al., 1987, "The receptor–binding sequence of urokinase", J. Biol. Chem. 262:4437–4440.

Artavanis–Tsakonas, 1995, "Notch signaling", Science 268:225–232.

Artavanis–Tsakonas, 1988, "The molecular biology of the Notch locus and the fine tuning of differentiation in Drosophila", Trends Genet. 4:95–100.

Artavanis–Tsakonas & Simpson, 1991, "Choosing a cell fate: a view from the Notch locus", Trends Genet. 7:403–408.

Bierkamp & Campos–Ortega, 1993, "A zebrafish homologue of the Drosophila neurogenic gene Notch and its pattern of transcription during early embryogenesis", Mech. Dev. 43:87–100.

Campos–Ortega, 1993, "Mechanisms of early neurogenesis in Drosophila melanogaster", J. Neurobiol. 24:1305–1327.

Chou, P. & Fasman, G., 1974, "Prediction of protein conformation", Biochemistry 13:222.

Coffman et al., 1990, "Xotch, the xenopus homolog of drosophila notch", Science 249:1438–1441.

Coffman et al., 1993, "Expression of an extracellular deletion of Xotch diverts fate in Xenopus embryos", Cell 73:659–671.

Conlon et al., 1995, "Notch 1 is required for the coordinate segmentation of somites", Development 121:1533–1545.

De la Concha et al., 1988, "Functional interactions of neurogenic genes of Drosophila melanogaster", Genetics 118:499–508.

Doe, 1992, "Molecular markers for identified neuroblasts and gangolin mother cells in the Drosophila central nervous system", Development 116:855–863.

Doe & Goodman, 1985, "Early events in insect neurogenesis", Dev. Biol. 111:206–219.

Fehon et al., 1990, "Molecular interactions between the protein products of the neurogenic loci notch and delta, two EGF–homologous genes in drosophila", Cell 61:523–534.

Fleming et al., 1990, "The gene Serrate encodes a putative EGF–like transmembrane protein essential for proper ectodermal development in Drosophila melanogaster", Genes Dev. 4:2188–2201.

Fortini & Artavanis–Tsakonas, 1993, "Notch: neurogenesis is only part of the picture", Cell 75:1245–1247.

Furie & Furie, 1988, "The molecular basis of blood coagulation", Cell 53:505–518.

Greenwald, 1994, "Structure/function studies of lin–12/notch proteins", Curr. Opin. Genet. Dev. 4:556–562.

Haenlin et al., 1990, "The pattern of transcription of the neurogenic gene Delta of Drosophila melanogaster", Development 110:905–914.

Heitzler & Simpson, 1991, "The choice of cell fate in the epidermis of drosophila", Cell 64:1083–1092.

Henderson et al., 1994, "lag–2 may encode a signaling ligand for the GLP–1 and LIN–12 receptors of C. elegans", Development 120:2913–2924.

Hopp, T. & Woods, K., 1981, "Prediction of protein antigenic determinants from amino acid sequences", PNAS USA 78:3824.

Kidd & Young, 1986, "Sequence of the notch locus of Drosophila melanogaster: relationship of the encoded protein to mammalian clotting and growth factors", Mol. Cell. Biol. 6:3094–3108.

Knust et al., 1987, "EGF homologous sequences encoded in the genome of drosophila melanogaster", EMBO J. 6(3): 761–766.

Kooh et al., 1993, "Implications of dynamic patterns of Delta and Notch expression for cellular interactions during drosophila development", Development 117:493–507.

Kopan & Weintraub, 1993, "Mouse Notch: expression in hair follicles correlates with cell fate determination", J. Cell. Biol. 121:631–641.

Kopan et al., 1994, "The intracellular domain of mouse Notch: a constitutively activated repressor of myogenesis directed at the basic helix–loop–helix region of MyoD", Development 120:2385–2396.

Kopczynski et al., 1988, "Delta, a Drosophila neurogenic gene, is transcriptionally complex and encodes a protein related to blood coagulation factors and epidermal growth factor of vertebrates", Genes Dev. 2:1723–1735.

Kurosawa et al., 1988, "A 10–kDa cyanogen bromide fragment from the epidermal growth factor homology domain of rabbit thrombomodulin contains the primary thrombin binding site", J. Biol. Chem. 263:5993–5996.

Lardelli & Lendahl, 1993, "Motch A and motch B–two mouse Notch homologues coexpressed in a wide variety of tissues", Exp. Cell. Res. 204:364–372.

Lardelli et al., 1994, "The novel Notch homologue mouse Notch 3 lacks specific epidermal growth factor–repeats and is expressed in proliferating neuroepithelium", Mech. Dev. 46:123–136.

Mello et al., 1994, "The maternal genes apx–1 and glp–1 and establishment of Dorsal ventral polarity in the early C. elegans embryo", Cell 77:95–106.

Muskavitch, 1994, "Delta–notch signaling and Drosophila cell fate choice", Dev. Biol. 166:415–430.

Nüsslein–Volhard et al., 1984, "Mutations affecting the pattern of the larval cuticle in Drosophila melanogaster", Dev. Biol. 193:267–282.

Nye et al., 1994, "An activated Notch suppresses neurogenesis and myogenesis but not gliogenesis in mammalian cells", Development 120:2421–2430.

Rebay et al., 1991, "Specific EGF repeats of Notch mediate interactions with delta and serrate: implications for notch as a multi–functional receptor", Cell 67:687–699.

Rebay et al., 1993, "Specific truncations of Drosophila Notch define dominant activated and dominant negative forms of the receptor", Cell 74:319–329.

Rees et al., 1988, "The role of β–hydroxyaspartate and adjacent carboxylate residues in the first EGF domain of human factor IX", EMBO J. 7:2053–2061.

Rothberg et al., 1988, "slit: An EGF–homologous locus of D. melanogaster involved in the development of the embryonic central nervous system", Cell 55:1047–1059.

Stemberg, 1993, "Falling off the knife edge", Current Biol. 3:763–765.

Sudhof et al., 1985, "The LDL receptor gene: a mosaic of exons shared with different proteins", Science 228:815–822.

Suzuki et al., 1987, "Structure and expression of human thrombomodulin, a thrombin receptor on endothelium acting as a cofactor for protein C activation", EMBO J. 6:1891–1897.

Swiatek et al., 1994, "Notch1 is essential for postimplantation development in mice", Genes Dev. 8:707–719.

Tax et al., 1994, "Sequence of C. elegans lag–2 reveals a cell–signalling domain shared with Delta and Serrate of Drosophila", Nature 368:150–154.

Technau & Campos–Ortega, 1986, "Lineage analysis of transplanted individual cells in embryos of *Drosophila melanogaster*", Dev. Biol. 195:445–454.

Thomas et al., 1991, "The *Drosophila* gene *Serrate* encodes an EGF–like transmembrane protein with a complex expression pattern in embryos and wing discs", Development 111:749–761.

Vässain et al., 1987, "the neurogenic gene Delta of *Drosophila melanogaster* is expressed in neurogenic territories and encodes a putative transmembrane protein with EGF–like repeats", EMBO J. 6:3431–3440.

Vässain et al., 1985, "Genetic interactions in early neurogenesis of *Drosophila melanogaster*", J. Neurogenet. 2:291–308.

Weinmaster et al., 1991, "A homolog of drosophila Notch expressed during mammalian development", Development 113:199–205.

Weinmaster et al., 1992, "Notch2: a second mammalian Notch gene", Development 116:931–941.

Wharton et al., 1985, "Nucleotide sequence from the neurogenic locus Notch implies a gene product that shares homology with proteins containing EGF–like repeats", Cell 43:567–581.

Wieschaus et al., 1984, "Mutations affecting the pattern of the larval cuticle in *Drosophila melanogaster*", Dev. Biol. 193:296–307.

Xu et al., 1990, "The *notch* locus and the genetic circuitry involved in early *drosophila* neurogenesis", Genes Dev. 4:464–475.

Yochem et al., 1988, "The *Caenorhabditis elegans lin–12* gene encodes a transmembrane protein with overall similarity to *Drosophila Notch*", Nature 335:547–550.

Henrique D, Adam J, 1995, Expression of a Delta homologue in prospective neurons in the chick. Nature 375(6534):787–90.

Bettenhausen et al., 1995, "Transient and restricted expression during mouse embryogenesis of DIII, a murine gene closely related to Drosophila Delta", Development.121(8):2407–18.

Chitnis et al., 1995, "Primary neurogenesis in Xenopus embryos regulated by a homologue of the *Drosophila neurogenic* gene Delta", Nature. 375(6534):761–6.

Lindsell et al., 1995, "Jagged: A Mammalian Ligand that Activates Notch 1", Cell 80:909–917.

Nye and Kopan, 1995, "Vertebrate Ligands for Notch", Current Biology 5(9):966–969.

Ellien et al., 1991, "TAN–1, the Human Homolog of the Drosophilia Notch Gene, is Broken by Chromosomal Translocations in T Lymphoblastic Neoplasms", Cell 66:649–661.

Bettenhausen et al., 1995, "Efficient isolation of novel mouse genes differentially expressed in early postimplantation embryos", Genomics 28:436–441.

Artavanis–Tsakonas et al., 1991, "The Notch locus and the cell biology of neuroblast segregation", Annu. Rev. Cell. Biol. 7:427–452.

Austin et al., 1995, "Vertebrate retinal ganglion cells are selected from competent progenitors by the action of *Notch*", Development 121:3637–3650.

Myat et al., 1996, "A chick homologue of Serrate and Its Relationship with Notch and Delta Homologues during Central Neurogenesis", Developmental Biology 174:233–247.

* cited by examiner

```
       GAATTCGGCACGAGGTTTTTTTTTTTTTTTTCCCCTCTTTTCTTTCTTTTCCTTTTGCC
  1    ---------+---------+---------+---------+---------+---------+ 60

ATCCGAAAGAGCTGTCAGCCGCCGCCGGGCTGCACCTAAAGGCGTCGGTAGGGGGATAAC
 61    ---------+---------+---------+---------+---------+---------+ 120

AGTCAGAGACCCTCCTGAAAGCAGGAGACGGGACGGTACCCCTCCGGCTCTGCGGGGCGG
121    ---------+---------+---------+---------+---------+---------+ 180

CTGCGGCCCCTCCGTTCTTTCCCCCTCCCCGAGAGACACTCTTCCTTTCCCCCCACGAAG
181    ---------+---------+---------+---------+---------+---------+ 240

ACACAGGGGCAGGAACGCGAGCGCTGCCCCTCCGCCATGGGAGGCCGCTTCCTGCTGACG
241    ---------+---------+---------+---------+---------+---------+ 300

CTCGCCCTCCTCTCGGCGCTGCTGTGCCGCTGCCAGGTTGACGGCTCCGGGGTGTTCGAG
301    ---------+---------+---------+---------+---------+---------+ 360

CTGAAGCTGCAGGAGTTTGTCAACAAGAAGGGGCTGCTCAGCAACCGCAACTGCTGCCGG
361    ---------+---------+---------+---------+---------+---------+ 420

GGGGGCGGCCCCGGAGGCGCCGGGCAGCAGCAGTGCGACTGCAAGACCTTCTTCCGCGTC
421    ---------+---------+---------+---------+---------+---------+ 480

TGCCTGAAGCACTACCAGGCCAGCGTCTCCCCCGAGCCGCCCTGCACCTACGGCAGCGCC
481    ---------+---------+---------+---------+---------+---------+ 540

ATCACCCCCGTCCTCGGCGCCAACTCCTTCAGCGTCCCCGACGGCGCGGGCGGCGCCGAC
541    ---------+---------+---------+---------+---------+---------+ 600

CCCGCCTTCAGCAACCCCATCCGCTTCCCCTTCGGCTTCACCTGGCCCGGCACCTTCTCG
601    ---------+---------+---------+---------+---------+---------+ 660

CTCATCATCGAGGCTCTGCACACCGACTCCCCCGACGACCTCACCACAGAAAACCCCGAG
661    ---------+---------+---------+---------+---------+---------+ 720

CGCCTCATCAGCCGCCTGGCCACCCAGAGGCACCTGGCGGTGGGCGAGGAGTGGTCCCAG
721    ---------+---------+---------+---------+---------+---------+ 780

GACCTGCACAGCAGCGGCCGCACCGACCTCAAGTACTCCTATCGCTTTGTGTGTGATGAG
781    ---------+---------+---------+---------+---------+---------+ 840
```

FIG. 1A1

```
              CACTACTACGGGGAAGGCTGCTCTGTCTTCTGCCGGCCCCGTGACGACCGCTTCGGTCAC
       841   ---------+---------+---------+---------+---------+---------+  900

TTCACCTGTGGAGAGCGTGGCGAGAAGGTCTGCAACCCAGGCTGGAAGGGCCAGTACTGC
       901   ---------+---------+---------+---------+---------+---------+  960

ACTGAGCCGATTTGCTTGCCTGGGTGTGACGAGCAGCACGGCTTCTGCGACAAACCTGGG
       961   ---------+---------+---------+---------+---------+---------+ 1020

GAATGCAAGTGCAGAGTGGGTTGGCAGGGGCGGTACTGTGACGAGTGCATCCGATACCCA
      1021   ---------+---------+---------+---------+---------+---------+ 1080

GGCTGCCTGCACGGTACCTGTCAGCAGCCATGGCAGTGCAACTGCCAGGAAGGCTGGGGC
      1081   ---------+---------+---------+---------+---------+---------+ 1140

GGCCTTTTCTGCAACCAGGACCTGAACTACTGCACTCACCACAAGCCATGCAAGAATGGT
      1141   ---------+---------+---------+---------+---------+---------+ 1200

CGGTGTACGTGGTTGTGGCCAGTCCCCTCGATGTGAACAAGAACGGCTGGACCCATGTGT
      1201   ---------+---------+---------+---------+---------+---------+ 1260

GGCTCCAGCTGCGAGATTGAAATCAACGAATGTGATGCCAACCCTTGCAAGAATGGTGGA
      1261   ---------+---------+---------+---------+---------+---------+ 1320

AGCTGCACGGATCTCGAGAACAGCTATTCCTGTACCTGCCCCCCAGGCTTCTATGGTAAA
      1321   ---------+---------+---------+---------+---------+---------+ 1380

AACTGTGAGCTGAGTGCAATGACTTGTGCTGATGGACCGTGCTTCAATGGAGGGCGATGC
      1381   ---------+---------+---------+---------+---------+---------+ 1440

ACTGACAACCCTGATGGTGGATACAGCTGCCGCTGCCCACTGGGTTATTCTGGGTTCAAC
      1441   ---------+---------+---------+---------+---------+---------+ 1500

TGTGAAAAGAAAATCGATTACTGCAGTTCCAGCCCTTGTGCTAATGGAGCCCAGTGCGTT
      1501   ---------+---------+---------+---------+---------+---------+ 1560

GACCTGGGGAACTCCTACATATGCCAGTGCCAGGCTGGCTTCACTGGCAGGCACTGTGAC
      1561   ---------+---------+---------+---------+---------+---------+ 1620

GACAACGTGGACGATTGCGCCTCCTTCCCCTGCGTCAATGGAGGGACCTGTCAGGATGGG
      1621   ---------+---------+---------+---------+---------+---------+ 1680
```

FIG. 1A2

```
      GTCAACGACTACTCCTGCACCTGCCCCCCGGGATACAACGGGAAGAACTGCAGCACGCCG
1681  ------------+---------+---------+---------+---------+---------+ 1740

GTGAGCAGATGCGAGCACAACCCCTGCCACAATGGGGCCACCTGCCACGAGAGAAGCAAC
1741  ------------+---------+---------+---------+---------+---------+ 1800

CGCTACGTGTGCGAGTGCGCTCGGGGCTACGGCGGCCTCAACTGCCAGTTCCTGCTCCCC
1801  ------------+---------+---------+---------+---------+---------+ 1860

GAGCCACCTCAGGGGCCGGTCATCGTTGACTTCACCGAGAAGTACACAGAGGGCCAGAAC
1861  ------------+---------+---------+---------+---------+---------+ 1920

AGCCAGTTTCCCTGGATCGCAGTGTGCGCCGGGATTATTCTGGTCCTCATGCTGCTGCTG
1921  ------------+---------+---------+---------+---------+---------+ 1980

TACCAGTCGGTGTACGTCATATCAGAAGAGAAAGATGAGTGCATCATAGCAACTGAGGTG
2401  ------------+---------+---------+---------+---------+---------+ 2460

TAAAACAGACGTGACGTGGCAAAGCTTATCGATACCGTCATCAAGCTT
2461  ------------+---------+---------+---------+-------- 2508
```

FIG. 1A3

```
   1 GAATTCGGCACGAGGTTTTTTTTTTTCCCCTCTCTTTCTTTTCCTTTTGCCATCCGAAAG     69
  70 AGCTGTCAGCCGCCGCGGGCTGCACCTAAAGGCGTCGGTAGGGGATAACAGTCAGAGACCCTCCTGA  138
 139 AAGCAGGAGACGGGACGGGTACCCCTCCGGCTCTGCGGGGCGGCTGCGGCCCCTTCTTTCCCCCTC    207
 208 CCCGAGAGACACTCTTCCTTCCCCCACGAAGACACAGGAAACGGCAGGAGCGCTGCCCCTCCGCC    276
 277 ATGGGAGGCCGCTTCGAGCTGAAGCTGCCCCTCCTCGGCGCTGCGTGCCGCTGCCAGGTTGACGGC   345
 346 TCCGGGGTGTTCGAGCTGAAGCTGCAGGAGTTTGTCAACAAGAAGGGGCTGCTCAGCAACCGCAACTGC  414
 415 TGCCGGGGGGCGGCCCCGGAGGGGCCGGGCAGCAGCAGTGCAGCTTCTTCCGGCTCTGC   483
 484 CTGAAGCACTACCAGGCCAGCGTCTCCCCCGAGCCGCACCTACGGCAGCGCCATCACCCCGTC   552
 553 CTCGGCGCCAACTCCTTCAGCGTCCCCGAGGACCTGCACCTACGGCGCCGGGACCCCGCCATC   621
 622 CGCTTCCCCCTTCGGCTTCACCTGGCCCGGCACCTTCTGCTCATCGAGGCTCTGCACACCGACTCC   690
 691 CCCGACGACCTCACCACAGAAAACCCGAGCGCCTCATCAGCCGCCTGGCCACCAGAGGCACCTGGCG   759
 760 GTGGGGAGGAGTGGTCCCAGGACCTGCACAGCAGGGCTGCAACCAGGTCTGCAACCCAAGTACTCCTATGCTTT   828
 829 GTGTGTGATGAGCACTACTAGGGGAAGGCTGCTCTGTCTTCTGCCGGCTGGGAATGCAAGTGCAGA   897
 898 CACTTCACCTGTGGAGAGCGTGGCGAGAAGGTCTGCAACCAGGCTGGAAGGGCCAGTACTGCACTGAG   966
 967 CCGATTTGCTTGCCTGGGTGTGACAGGCGGTACTGTGACAGGGTGCATCGACATACCCAGCTGTCAG  1035
1036 GTGGGTTGGCAGGGGCGGTCAACTGCCAGGAATGGTGCCACATGCCAGGGCCCTTTCTGCAACCAGACCGGT  1104
1105 CAGCCATGGCAGTGCAGTGCAACTGCAAGAATGGTGCCACATGCCAGGGAGAATCAACCGGTCAGGGAGCTACACTTGTTCT  1173
1174 ACTCACCACAAGCCATGCAAGATGGTGCCACATGCCAGGGCTCCAGCTGCGAGATTGAAATCAACGAATGTGATGCAACCCTTGCAAG  1242
1243 TGCCGACCTGGGTACACAGGCTCCAGCTGCGAGATTGAAATCAACGAATGTGATGCCAACCCTTGCAAG  1311
1312 AATGGTGGAAGCTGCACGGATCTCGAGAACAGCTATTCCTGTACCTGCCCCCAGGCTTCTATGGTAAA  1380
1381 AACTGTGAGCTGAATGACTTGTGCTGATGACCGTGCTTCAATGGAGGCGATGCACTGACAAC  1449
1450 CCTGATGGTGGATACAGCTGCGCTGCCACTGGGTTATTCTGGGTTCAACTGTGAAAAGAAAATCGAT  1518
1519 TACTGCAGTTCCAGTGGAAGCTGCCCTTGTGCTAATGGAGCCAGTGCGTTGACCTGGGAACTCCTACATGCCAG  1587
1588 TGCCAGGCTGGCTTCACTGGCCAGGCACTGCTGACAACGTGACGACACTACTCCTGCCCCTCCCCTGGTC  1656
1657 AATGGAGGGACCTGTCAGGATGGGGTCAACGACTACTCCTGCACCTGCCCCCCGGGATACAACGGGAAG  1725
1726 AACTGCAGCACGCCGGTGAGCGAGAGCGACATGCGAGCAGATGGGAGCACAACCCCTGCCACCCTGCCACGAGAGA  1794
```

FIG. 1B1

```
1795 AGCAACCGCTACGTGTGCGAGTGCGCTCGGGGCTACGGCGGCCTCAACTGCCAGTTCCTGCTCCCCGAG 1863
1864 CCACCTCAGGGGCCGGTCATCGTTGACTTCACCGAGAAGTACACAGAGGGCCAGAACAGCCAGTTTCCC 1932
1933 TGGATGCAGTGTGCGCGGGATTATTCTGGTCTCCTCATGTCTGTGGGTTGCGCCGCCATGTCGTGTC 2001
2002 TGCGTCAGGCTGAAGGTGCAGAAGAGGCACCACCAGCCCGAGGCCTGCAGGAGTGAAACGGAGACCATG 2070
2071 AACAACCTGGGCGAACTGCCAGGCGGAGAAGGACATCTCCATCAGGTGTCATCGGTGCCACTCAGATTAAA 2139
2140 AACACAAATAGAAAAGTAGACTTTCACGCGATAACTCCGATAAAAACGGCTACAAAGTTAGATACCCA 2208
2209 TCAGTGGATTACAATTTGGTGCATGAACTCAAGAATGAGGACTCTGTGAAAGAGGAGCATGCAAATGC 2277
2278 GAAGCCAAGTGTGAAACGTATGATTCAGAGGCAGAGAGAAAAGCGCAGTACAGTTAAAAAGTAGTGAC 2346
2347 ACTTCTGAAAGAGAAAACGGCCAGATTCAGTATATTCCACTTCAAGGACACAAAGTACCAGTCGGTAC 2415
2416 GTCATATCAGAGAAGAATGAGTGCATCATAGCAACTGAGGTTAGTATCCACCTGGCAGTCGGACA 2484
2485 AGTCTTGGTGTGTGATTCCCATCCAGGCAGGTCAGGGCCAAACCATTCTACCTGTTGCTGCCACAGTC 2553
2554 ATCTGTACCCAATGAAAACTGAAAAACTGGCCACCTTCAGTGTGTGGCACTGTGTGCAGAGGCGGTGAAAAACTGTTGTGG 2622
2623 ATTAACATAAGCTTACTAACCCTGAGTGGGGGTTACAGGGACAATTTTTGCAGGCAAGGTATAACTGTAGTGCA 2691
2692 GTTGTAGCTTACTAACCTACTGACTCATTCTTCGTGTGCTTCCTGCAGAGCCTGTTTTTGCTTGGCA 2760
2761 TTGAGGTGAAGTCCTGACCCTCTGCATCCTCATAGTCCTCTGCTTTCTTTTTATTAACCTCTTCTGTC 2829
2830 TCTGCTTGTGTTTCTCTCAACAGGTGTAAAACAGAGCGTGACGTGGCAAAGCTT 2883
```

FIG. 1B2

```
  1 MGGRFLLTLA LLSALLCRCQ VDGSGVFELK LQEFVNKKGL LSNRNCCRGG GPGGAGQQQC
 61 DCKTFFRVCL KHYQASVSPE PPCTYGSAIT PVLGANSFSV PDGAGGADPA FSNPIRFPFG
121 FTWPGTFSLI IEALHTDSPD DLTTENPERL ISRLATQRHL AVGEEWSQDL HSSGRTDLKY
181 SYRFVCDEHY YGEGCSVFCR PRDDRFGHFT CGERGEKVCN PGWKGQYCTE PICLPGCDEQ
241 HGFCDKPGEC KCRVGWQGRY CDECIRYPGC LHGTCQQPWQ CNCQEGWGGL FCNQDLNYCT
301 HHKPCKNGAT CTNTGQGSYT CSCRPGYTGS SCEIEINECD ANPCKNGGSC TDLENSYSCT
361 CPPGFYGKNC ELSAMTCADG PCFNGGRCTD NPDGGYSCRC PLGYSGFNCE KKIDYCSSSP
421 CANGAQCVDL GNSYICQCQA GFTGRHCDDN VDDCASFPCV NGGTCQDGVN DYSCTCPPGY
481 NGKNCSTPVS RCEHNPCHNG ATCHERSNRY VCECARGYGG LNCQFLLPEP PQGPVIVDFT
541 EKYTEGQNSQ FPWIAVCAGI ILVLMLLLGC AAIVVCVRLK VQKRHHQPEA CRSETETMNN
601 LANCQREKDI SISVIGATQI KNTNKKVDFH SDNSDKNGYK VRYPSVDYNL VHELKNEDSV
661 KEEHGKCEAK CETYDSEAEE KSAVQLKSSD TSERKRPDSV YSTSKDTKYQ SVYVISEEKD
721 ECIIATEV
```

|  |  |  |  |  |  |  |  |
|---|---|---|---|---|---|---|---|
| C-Delta-1 | 184 | V-CDEHYYGE | GCSVFCRPRD | DRFGHFTCGE | RGEKVCNPGW | RGQYC | 228 |
| Delta | 182 | VTCDLNYYGS | GCAKFCRPRD | DSFGHSTCSE | TGEIICLTGW | QGDYC | 226 |
| Serrate | 235 | VQCAVTYYNT | TCTTFCRPRD | DQFGHYACGS | EGQKLCLNGW | QGVNC | 279 |
| C-Serrate-1 |  | VTCAEHYYGF | GCNKFCRPRD | DFFTHHTCDQ | NGNKTCLEGW | TGPEC |  |
|  |  |  |  |  |  |  |  |
| Apx-1 | 130 | NLCSSNYHGK | RCNRYCIAN- | AKLHWE-CST | HGVRRCSAGW | SGEDC | 172 |
| Lag-2 | 120 | VTCARNYFGN | RCENFCDAHL | AKAARKRCDA | MGRLRCDIGW | MGPHC | 166 |

```
CTGCAGGAAT TCSMYCGCAT GCTCCCCGGCC GCCATGGGCC GTCGGAGCGC GCTAGCCCTT    60
GCCGTGGTCT CTGCCCCTGCT GTGCCAGGTC TGGAGCTCCG GCGTATTTGA GCTGAAGCTG   120
CAGGAGTTCG TCAACAAGAA GGGGCTGCTG GGGAACCGCA ACTGCTGCCG CGGGGGCTCT   180
GGCCCGCCTT GCGCCTGCAG GACCTTCTTT CGCGTATGCC TCAAGCACTA CCAGGCCAGC   240
GTGTCACCGG AGCCACCCTG CACCTACGGC AGTGCCGTCA CGCCAGTGCT GGGTGTCGAC   300
TCCTTCAGCC TGCCTGATGG CGCAGGCATC GACCCCGCCT TCAGCAACCC CATCCGATTC   360
CCCTTCGGCT TCACCTGGCC AGTTACCTTC TCTCTGATCA TTTGAAGCCCT CCATACAGAC   420
TCTCCCGATG ACCTCGCAAC AGAAAACCCA GAAAGACTCA TCAGCCGCCT GACCACACAG   480
AGGCACCTCA CTGTGGGAGA AGAATGGTCT CAGGACCTTC ACAGTAGCGG CCGCACAGAC   540
CTCCGGTACT CTTACCGGTT TGTGTGTGAC GAGCACTACT ACGGAGAAGG TTGCTCTGTG   600
TTCTGCCGAC CTCGGGATGA CGCCCTTTGGC CACTTCACCT GCGGGGACAG AGGGGAGAAG   660
ATGTGCGACC CTGGCTGGAA AGGCCAGTAC TGCACTGACC CAATCTGTCT GCCAGGGTGT   720
GATGACCAAC ATGGATACTG TGACAAACCA GGGGAGTGCA AGTGCAGAGT TGGCTGGCAG   780
GGCCGCTACT GCGATGAGTG CATCCGATAC CCAGGTTGTC TCCATGGCAC CTGCCAGCAA   840
CCCTGGCAGT GTAACTGCCA GGAAGGCTGG GGGGCCTTT TCTGCAACCA AGACCTGAAC   900
TACTGTACTC ACCATAAGCC GTGCAGGAAT GGAGCCACCT TCTGCCAACC GCACCAAACAC   960
AGCTACACAT GTTCCTGCCG ACCTGGGTAT ACAGGTGCCA ACTGTGAGCT GGAAGTAGAT  1020
GAGTGTGCTC CTAGCCCCTG CAAGAACGGA GCCAGCTGCA CGGACCTTGA GGACAGCTTC  1080
TCTTGCACCT GCCCTCCCGG CTTCTATGGC AAGGTCTGTG AGCTGAGCGC CATGACCTGT  1140
GCAGATGGCC CTTGCTTCAA TGGAGGACGA TGTTCAGATA ACCCTGACGG AGGCTACACC  1200
TGCCATTGCC CCTTGGGCTT CTCTGGCTTC AACTGTGAGA AGAAGATGGA TCTCTGCGGC  1260
TCTTCCCCTT GTTCTAACGG TGCCAAGTGT GTGGACCTCG GCAACTCTTA CCTGTGCCGG  1320
TGCCAGGCTG GCTTCTCCGG GAGGTACTGC GAGGACAATG TGGATGACTG TGCCTCCTCC  1380
```

| | | | | |
|---|---|---|---|---|
| CCGTGTGCAA | ATGGGGGCAC | CTGCCGGGAC | AGTGTGAACG | ACTTCTCCTG | TACCTGCCCA | 1440 |
| CCTGGCTACA | CGGGCAAGAA | CTGCAGCGCC | CCTGTCAGCA | GGTGTGAGCA | TGCACCCTGC | 1500 |
| CATAATGGGG | CCACCTGCCA | CCAGAGGGGC | CAGCGCTACA | TGTGTGAGTG | CGCCCAGGGC | 1560 |
| TATGGCGGCC | CCAACTGCCA | GTTTCTGCTC | CCTGAGCCAC | CACCAGGGCC | CATGGTGGTG | 1620 |
| GACCTCAGTG | AGAGGCATAT | GGAGAGCCAG | GGCGGGCCCT | TCCCCTGGGT | GGCCGTGTGT | 1680 |
| GCCGGGGTGG | TGCTTGTCCT | CCTGCTGCTG | CTGGGCTGTG | CTGTCTGCGT | GGTCTGCGTC | 1740 |
| CGGCTGAAGC | TACAGAAACA | CCAGCCTCCA | CCTGAACCCT | GTGGGGGAGA | GACAGAAACC | 1800 |
| ATGAACAACC | TAGCCAATTG | CCAGCGCGAG | AAGGACGTTT | CTGTTAGCAT | CATTGGGGCT | 1860 |
| ACCAGATCA | AGAACACCAA | CAAGAAGGCG | GACTTTCACG | GGGACCATGG | AGCCGAGAAG | 1920 |
| AGCAGCTTTA | AGGTCCGATA | CCCCACTGTG | GACTATAACC | TCGTTCGAGA | CCTCAAGGGA | 1980 |
| GATGAAGCCA | CGGTCAGGGA | TACACACAGC | AAACGTGACA | CCAAGTGCCA | GTCACAGAGC | 2040 |
| TCTGCAGGAG | AAGAGAAGAT | CGCCCAACA | CTTAGGGGTG | GGGAGATTCC | TGACAGAAAA | 2100 |
| AGGCCAGAGT | CTGTCTACTC | TACTTCAAAG | GACACCAAGT | ACCAGTCGGT | GTATGTTCTG | 2160 |
| TCTGCAGAGT | AGGATGAGTG | TGTTATAGCG | ACTGAGGTGT | AAGATGGAAG | CGATGTGGCA | 2220 |
| AAATTCCCAT | TTCTCTAAA | TAAAATTCCA | AGGATATAGC | CCCGATGAAT | GCTGCTGAGA | 2280 |
| GAGGAAGGGA | GAGGAAACCC | AGGGACTGCT | GCTGAGAACC | AGGTTCAGGC | GAACGTGGTT | 2340 |
| CTCTCAGAGT | TAGCAGAGGC | GCCCGACACT | GCCAGCCCTAG | GCTTTGGCTG | CCGCTGGACT | 2400 |
| GCCTGCTGGT | TGTTCCCATT | GCACTATGGA | CAGTTGCTTT | GAAGAGTATA | TATTTAAATG | 2460 |
| GACGAGTGAC | TTGATTCATA | TAGGAAGCAC | GCACTGCCCA | CACGTCTATC | TTGGATTACT | 2520 |
| ATGAGCCAGT | CTTTCCTTGA | ACTAGAAACA | GCACTGCCCTT | TATTGTCCTT | TTTGATACTG | 2580 |
| AGATGTGTTT | TTTTTTTTC | CTAGACGGGA | AAAAGAAAAC | GTGTGTTATT | TTTTTTTGGA | 2640 |
| TTTGTAAAAA | TATTTTTCAT | GATTATGGGA | GAGCTCCCAA | CGCGGTTGGAG | GT | 2692 |

FIG. 7B

| | | | | |
|---|---|---|---|---|
| MGRRSALALA | VVSALLCQVW | SSGVFELKLQ | EFVNKKGLLG | NRNCCRGGSG | 50 |
| PPCACRTFFR | VCLKHYQASV | SPEPPCTYGS | AVTPVLGVDS | FSLPDGAGID | 100 |
| PAFSNPIRFP | FGFTWPGTFS | LIIEALHTDS | PDDLATENPE | RLISRLTTQR | 150 |
| HLTVGEEWSQ | DLHSSGRTDL | RYSYRFVCDE | HYYGEGCSVF | CRPRDDAFGH | 200 |
| FTCGDRGEKM | CDPGWKGQYC | TDPICLPGCD | DQHGYCDKPG | ECKCRVGWQG | 250 |
| RYCDECIRYP | GCLHGTCQQP | WQCNCQEGWG | GLFCNQDLNY | CTHHKPCRNG | 300 |
| ATCTNTGQGS | YTCSCRPGYT | GANCELEVDE | CAPSPCKNGA | SCTDLEDSFS | 350 |
| CTCPPGFYGK | VCELSAMTCA | DGPCFNGGRC | SDNPDGGYTC | HCPLGFSGFN | 400 |
| CEKKMDLCGS | SPCSNGAKCV | DLGNSYLCRC | QAGFSGRYCE | DNVDDCASSP | 450 |
| CANGGTCRDS | VNDFSCTCPP | GYTGKNCSAP | VSRCEHAPCH | NGATCHQRGQ | 500 |
| RYMCECAQGY | GGPNCQFLLP | EPPPGPMVVD | LSERHMESQG | GPFPWVAVCA | 550 |
| GVVLVLLLLL | GCAAVVVCVR | LKLQKHQPPP | EPCGGETETM | NNLANCQREK | 600 |
| DVSVSIIGAT | QIKNTNKKAD | FHGDHGAEKS | SFKVRYPTVD | YNLVRDLKGD | 650 |
| EATVRDTHSK | RDTKCQSQSS | AGEEKIAPTL | RGGEIPDRKR | PESVYSTSKD | 700 |
| TKYQSVYVLS | AEKDECVIAT | EV | | | 722 |

FIG. 8

```
CHICK DELTA      MGGRFLLTLA LLSALLCRCQ VDGSGVFELK LQEFVNKKGL LSNRNCCRGG  50
MOUSE DELTA.PEP  MGRRSALALA VVSALLCQ—  VWSSGVFELK LQEFVNKKGL LGNRNCCRGG  48

CONSENSUS        MG.R..L.LA ..SALLC... V..SGVFELD LQEFVNKKGL L.NRNCCRGG  50

CHICK DELTA      GPGGAGQQQC DCKTFFRVCL KHYQASVSPE PPCTYGSAIT PVLGANSFSV 100
MOUSE DELTA.PEP  —SGP——PC ACRTFFRVCL KHYQASVSPE PPCTYGSAVT PVLGVDSFSL  93

CONSENSUS        ...G.....C .C.TFFRVCL KHYQASVSPE PPCTYGSA.T PVLG..SFS. 100

CHICK DELTA      PDGAGGADPA FSNPIRFPFG FTWPGTFSLI IEALHTDSPD DLTTENPERL 150
MOUSE DELTA.PEP  PDGAG-IDPA FSNPIRFPFG FTWPGTFSLI IEALHTDSPD DLATENPERL 142

CONSENSUS        PDGAG..DPA FSNPIRFPFG FTWPGTFSLI IEALHTDSPD DL.TENPERL 150

CHICK DELTA      ISRLATQRHL AVGEEWSQDL HSSGRTDLKY SYRFVCDEHY YGEGCSVFCR 200
MOUSE DELTA.PEP  ISRLTTQRHL TVGEEWSQDL HSSGRTDLRY SYRFVCDEHY YGEGCSVFCR 192

CONSENSUS        ISRL.TQRHL .VGEEWSQDL HSSGRTDL.Y SYRFVCDEHY YGEGCSVFCR 200

CHICK DELTA      PRDDRFGHFT CGERGEKVCN PGWKGQYCTE PICLPGCDEQ HGFCDKPGEC 250
MOUSE DELTA.PEP  PRDDAFGHFT CGDRGEKVCD PGWKGQYCTD PICLPGCDDQ HGYCDKPGEC 242

CONSENSUS        PRDD.FGHFT CG.RGEK.C. PGWKGQYCT. PICLPGCD.Q HG.CDKPGEC 250

CHICK DELTA      KCRVGWQGRY CDECIRYPGC LHGTCQQPWQ CNCQEGWGGL FCNQDLNYCT 300
MOUSE DELTA      KCRVGWQGRY CDECIRYPGC LHFTCQQPWQ CNCQEGWGGL FCNQDLNYCT 292

CONSENSUS        KCRVGWQGRY CDECIRYPGC LHGTCQQPWQ CNCQEGWGGL FCNQDLNYCT 300

CHICK DELTA      HHKPCKNGAT CTNTGQGSTY CSCRPGYTGS SCEIEINECD ANPCKNGGSC 350
MOUSE DELTA.PEP  HHKPCRNGAT CTNTGQGSYT CSCRPGYTGA NCELEVDECA PSPCKNGASC 342

CONSENSUS        HHKPC.NGAT CTNTGQGSYT CSCRPGYTG. .CE.E..EC. ..PCKNG.SC 350

CHICK DELTA      TDLENSYSCT CPPGFYGKNC ELSAMTCADG PCFNGGRCTD NPDGGYSCRC 400
MOUSE DELTA.PEP  TDLEDSFSCT CPPGFYGKVC ELSAMTCADG PCFNGGRCSD NPDGGYTCHC 392

CONSENSUS        TDLE.S.SCT CPPGFYGK.C ELSAMTCADG PCFNGGRC.D NPDGGY.C.C 400

CHICK DELTA      PLGYSGFNCE KKIDYCSSSP CANGAQCVDL GNSYICQCQA GFTGRHCDDN 450
MOUSE DELTA.PEP  PLGFSGFNCE KKMDLCGSSP CSNGAKCVDL GNSYLCRCQA GFSGRYCEDN 442

CONSENSUS        PLG.SGFNCE KK.D.C.SSP C.NGA.CVDL GNSY.C.CQA GF.GR.C.DN 450
```

FIG.9A

```
CHICK DELTA       VDDCASFPQV NGGTCQDGVN DYSCTCPPGY NGKNCSTPVS RCEHNPCHNG 500
MOUSE DELTA.PEP   VDDCASSPQA NGGTCRDSVN DFSCTCPPGY TGKNCSAPVS RCEHAPCHNG 492

CONSENSUS         VDDCAS.PQ. NGGTC.D.VN D.SCTCPPGY .GKNCS.PVS RCEH.PCHNG 500

CHICK DELTA       ATCHERSNRY VCECARGYGG LNCQFLLPEP PGGFVIVDFT EKYTEGQNSQ 550
MOUSE DELTA       ATCHQRGQRY MCECAQGYGG PNCQFLLPEP PPGPMVWDLS ERHMESQGGP 542

CONSENSUS         ATCH.R..RY .CECA.GYGG ..NCQFLLPEP P.GP..VD.. E...E.Q... 550

CHICK DELTA       FPWIAVCAGI ILVLMLLGC  AAIVVCVRLK VQKRHHQPEA CRSETETMNN 600
MOUSE DELTA.PEP   FPWMAVCAGV VLVLLLLGC  AAVVVCVRLK LQKHQPPPEP CGGETETMNN 592

CONSENSUS         FPW.AVCAG. .LVL.LLGC  AA.VVCVRLK .QK....PE. C..ETETMNN 600

CHICK DELTA       LANCQREKDI SISVIGATQI KNTNKKVDFH SDN-SDKNGY KVRYPSVDYN 649
MOUSE DELTA       LANCQREKDV SVSIIGATQI KNTNKKADFH GDHGAEKSSF KVRYPTVDYN 642

CONSENSUS         LANCQREKD. S.S.IGATQI KNTNKK.DFH .D....K... KVRYP.VDYN 650

CHICK DELTA       LVHELKNED- SVKEEHGKCE AKCETYDSEA EEKSAVQLKS SDTSERKRPD 698
MOUSE DELTA.PEP   LVRDLKGDEA TVRDTHSKRD TKCQSQSSAG EEKIAPTLRG GEIPDRKRPE 692

CONSENSUS         LV..LK.... .M..H.K... .KC.....S. EEK.A..L.. .....RKRP. 700

CHICK DELTA       SVYSTSKDTK YQSVYVISEE KDECIIATEV 728
MOUSE DELTA.PEP   SVYSTSKDTK YQSVYVLSAE KDECVIATEV 722
CONSENSUS         SVYSTSKDTK YQSVYV.S.E KDEC.IATEV 730
```

FIG.9B

```
         10         20         30         40         50         60
                     *                     *                     *
TACGATGAAY AACCTGGCGA ACTGCCAGCG TCAGAAGGAC ATCTCAGTCA GCATCATCGG
 Y D E      X P G E    L P A     * E G      H L S Q     H H R>
  T M N     N L A     N C Q R    E K D      I S V       S I I G>
   R * X     T W R     T A S      V R R T    S Q S       A S S>

70         80         90        100        110        120
                     *                     *                     *
GGCYACGTCA GATCARGAAC ACCAACAAGA AGGCGGACTT YMCASCGGGG GACCASAGCG
 G X V      R S X T    P T R     R R T      X X R G     T X A>
  A T S     D Q E     H Q Q E    G G L      X X G       G P X R>
   G X R Q   I X N     T N K      K A D F    X X G       D X S>

130        140        150        160        170        180
                     *                     *                     *
TCCGACAAGA ATGGMTTTCA AGGCCYGCTA CCCCAGCGTG GACTATAACT CGTGCAGGAC
 S D K      N G F Q    G P L     P Q R      G L * L     V Q D>
  P T R     M X F      K A R Y    P S V     D Y N       S C R T>
   V R Q E   W X S      R P A     T P A W    T I T       R A G>

190        200        210        220        230        240
                     *                     *                     *
CTCAAGGGTG ACGACACCGC CGTCAGGACG TCGCACAGCA AGCGTGACAC CAAGTGCCAG
 L K G      D D T A    V R T     S H S      K R D T     K C Q>
  S R V     T T P     P S G R    R T A      S V T       P S A S>
   P Q G *   R H R     R Q D     V A Q Q    A * H       Q V P>

250        260        270        280        290        300
                     *                     *                     *
TCCCCAGGCT CCTCAGGGAG GAGAAGGGGA CCCCGACCAC ACTCAGGGGK TGCGTGCTGC
 S P G      S S G R    R R G     P R P      H S G X     A C C>
  P Q A     P Q G     G E G D    P D H      T Q G       X R A A>
   V P R L   L R E     E K G      T P T T    L R G       C V L>

310        320        330        340        350        360
                     *                     *                     *
GGGCCGGGCT CAGGAGGGGG TACCTGGGGG GTGTCTTCCT GGAACCACTG CTCCGTTTCT
 G P G      S G G G    T W G     V S S      W N H C     S V S>
  G R A     Q E G     V P G G    C L P      G T T       A P F L>
   R A G L   R R G     Y L G      G V F L    E P L       L R F>
```

FIG. 10A

```
           370        380        390        400        410        420
                       *                     *                     *
        CTTCCCAAAT GTTCTCATGC ATTCATTGTG GATTTTCTCT ATTTTCCTTT TAGTGGAGAA
         L  P  K    C  S  H  A  F  I  V    D  F  L    Y  F  P  F   S  G  E>
          F  P  N   V  L  M    H  S  L  W  I  F  S    I  F  L     L  V  E  K>
        S  S  Q  M   F  S  C    I  H  C   G  F  S  L   F  S  F    *  W  R>

430        440        450        460        470        480
                       *                     *                     *
        GCATCTGAAA GAAAAAGGCC GGACTCGGGC TGTTCAACTT CAAAAGACAC CAAGTACCAG
         A  S  E    R  K  R  P  D  S  G    C  S  T    S  K  D  T   K  Y  Q>
          H  L  K   E  K  G    R  T  R  A  V  Q  L    Q  K  T     P  S  T  S>
        S  I  *  K   K  K  A    G  L  G  L  F  N  F    K  R  H    Q  V  P>

490        500        510        520
             *                     *
        TCGGTGTACG TCATATCCGA GGAGAAGGAC GAGTGCGTCA TCGCA
         S  V  Y    V  I  S  E   E  K  D   E  C  V    I  A>
          R  C  T   S  Y  P     R  R  R  T  S  A  S    S>
        V  G  V  R  H  I  R    G  E  G   R  V  R  H    R>
```

FIG. 10B

```
  1 TMNNLANCQREKDISVSIIGATQIXNTNKKADFXXGDXSSDKNGFQKARY  50
    |||||||||||||:|:|||||||||||·||  ::    |||||: |·||
597 TMNNLANCQREKDISISVIGATQIKNTNKKVDFHSDN..SDKNGY.KVRY 643

51 PSVDYNLVQDLKGDDTAVRTSHSKRDTKCQSPGSSGRRRGPRPHSGXACC 100
    ||||||||::||·:|  .|:..|:|  :.||:  ·:|.:    :::
644 PSVDYNLVHELKNED.SVKEEHGKCEAKCETYDSEAEEKSA........ 683

101 GPGSGGGTWGVSSWNHCSVSLPKCSHAFIVDFLYFPFSGEASERKRPDSG 150
                          |::       |::·||||||||·
684 .........................VQLK....SSDTSERKRPDSV 700

151 CSTSKDTKYQSVYVISEEKDECVIA  175
    :|||||||||||||||||||||||:||
701 YSTSKDTKYQSVYVISEEKDECIIA 725
```

FIG.11

```
          10         20         30         40         50         60
           *          *          *          *          *          *
     CATTGGGTAC GGGCCCCCCT CGAGGTCGAC GGTATCGATA AGCTTGATAT CGAATTCCGG
          70         80         90        100        110        120
           *          *          *          *          *          *
     CTTCACCTGG CCGGGCACCT TCTCTCTGAT TATTGAAGCT CTCCACACAG ATTCTCCTGA
         130        140        150        160        170        180
           *          *          *          *          *          *
     TGACCTCGCA ACAGAAAACC CAGAAAGACT CATCAGCCGC CTGGCCACCC AGAGGCACCT
         190        200        210        220        230        240
           *          *          *          *          *          *
     GACGGTGGGC GAGGAGTGGT CCCAGGACCT GCACAGCAGC GGCCGCACGG ACCTCAAGTA
         250        260        270        280        290        300
           *          *          *          *          *          *
     CTCCTACCGC TTCGTGTGTC ACCAACACTA CTACGGAGAG GGCTGCTCCG TTTTCTGCCG
         310        320        330        340        350        360
           *          *          *          *          *          *
     TCCCCGGGAC GATGCCTTCG GCCACTTCAC CTGTGGGGAG CGTGGGGAGA AAGTGTGCAA
         370        380        390        400        410        420
           *          *          *          *          *          *
     CCCTGGCTCG AAAGGGCCCT ACTGCACAGA GCCGATCTGC CTGCCTGGAT GTGATGAGCA
         430        440        450        460        470        480
           *          *          *          *          *          *
     GCATGGATTT TGTGACAAAC CAGGGGAATG CAAGTGCAGA GTGGGCTGGC AGGGCCGGTA
         490        500        510        520        530        540
           *          *          *          *          *          *
     GTGTGACGAG TGTATCCGCT ATCCAGGCTG TCTCCATGGC ACCTGCCAGC AGCCCTGGCA
         550        560        570        580        590        600
           *          *          *          *          *          *
     GTGCAACTGC CAGGAAGGNT GGGGGGGGCCT TTTCTGCAAC CAGGACCTGA ACTACTGCAC
         610        620        630        640        650        660
           *          *          *          *          *          *
     ACACCATAAG CCCTGCAAGA ATGGAGCCAC CTGCAACAAA CACGGGCCAG GGGAGCTAC
         670        680        690        700        710        720
           *          *          *          *          *          *
     ACTTGGTCTT TGGCCGGNCT GGGGTACANA GGGTGCCACC TGCGAAGCTT GGGGATTGGA
         730        740        750        760        770        780
           *          *          *          *          *          *
     CGAGTTGTTG ACCCCAGCCC TTGGTAAGAA CGGAGGGAGC TTGACGGATC TTCGGAGAAC
         790        800        810        820        830        840
           *          *          *          *          *          *
     AGCTACTCCT GTACCTGCCC ACCCGGCTTC TACGGCAAAA TCTGTGAATT GAGTGCCATG
         850        860        870        880        890        900
           *          *          *          *          *          *
     ACCTGTGCGG ACGGCCCTTG CTTTAACGGG GGTCGGTGCT CAGACAGCCC CGATGGAGGG
```

FIG. 12A1

```
        910         920         930         940         950         960
     *     *     *     *     *     *     *     *     *     *     *     *
   TACAGCTGCC  GCTGCCCCGT  GGGCTACTCC  GGCTTCAACT  GTGAGAAGAA  AATTGACTAC
        970         980         990        1000        1010        1020
     *     *     *     *     *     *     *     *     *     *     *     *
   TGCAGCTCTT  CACCCTGTTC  TAATGGTGCC  AAGTGTGTGG  ACCTCGGTGA  TGCCTACCTG
       1030        1040        1050        1060        1070        1080
     *     *     *     *     *     *     *     *     *     *     *     *
   TGCCGCTGCC  AGGCCGGCTT  CTCGGGGAGG  CACTGTGACG  ACAACGTGGA  CGACTGCGCC
       1090        1100        1110        1120        1130        1140
     *     *     *     *     *     *     *     *     *     *     *     *
   TCCTCCCCGT  GCGCCAACGG  ACCTCGGTGA  CGGGATGGCG  TGAACGACTT  CTCCTGCACC
       1150        1160        1170        1180        1190        1200
     *     *     *     *     *     *     *     *     *     *     *     *
   TGCCCGCCTG  GCTACACGGG  CAGGAACTGC  AGTGCCCCCG  CCAGCACCTG  CGAGCACGCA
       1210        1220        1230        1240        1250        1260
     *     *     *     *     *     *     *     *     *     *     *     *
   CCCTGCCACA  ATGGGGCCAC  CTGCCACGAG  AGGGGCCACC  GCTATNTGTG  CGAGCACGCA
       1270        1280        1290        1300        1310        1320
     *     *     *     *     *     *     *     *     *     *     *     *
   CGAAGCTACG  GGGGTCCCAA  CTCCCANTTC  CTGCTCCCCC  AAACTGCCCC  CCCGGCCCCA
       1330        1340        1350        1360        1370        1380
     *     *     *     *     *     *     *     *     *     *     *     *
   CGGTGGTGGA  AACTCCCCTA  AAAAAACCTA  AAAGGGCCGG  GGGGGGCCCA  TCCCCTTGGT
       1390        1400        1410        1420        1430        1440
     *     *     *     *     *     *     *     *     *     *     *     *
   GGACGTGTGC  GCCGGGGTCA  TCCTTGTCCT  CATGCTGCTG  CTGGGCTGTG  CCGCTGTGGT
       1450        1460        1470        1480        1490        1500
     *     *     *     *     *     *     *     *     *     *     *     *
   GGTCTGCGTC  CGGCTGAGGC  TGCAGAAGCA  CCGGCCCCCA  GCCGACCCCT  GNCGGGGGGA
       1510        1520        1530        1540        1550        1560
     *     *     *     *     *     *     *     *     *     *     *     *
   GACGGAGACC  ATGAACAACC  TGGNCAACTG  CCAGCGTGAG  AAGGACATCT  CAGTCAGCAT
       1570        1580        1590        1600        1610        1620
     *     *     *     *     *     *     *     *     *     *     *     *
   CATCGGGGNC  ACGCAGATCA  AGAACACCAA  CAAGAAGGCG  GACTTCCACG  GGGACCACAG
       1630        1640        1650        1660        1670        1680
     *     *     *     *     *     *     *     *     *     *     *     *
   NGCCGACAAG  AATGGCTTCA  AGGCCCGCTA  CCCAGNGGTG  GACTATAACC  TCGTGCAGGA
       1690        1700        1710        1720        1730        1740
     *     *     *     *     *     *     *     *     *     *     *     *
   CCTCAAGGGT  GACGACACCG  CCGTCAGCCA  CGCGCACAGC  AAGCGTGACA  CCAAGTGNCA
       1750        1760        1770        1780        1790        1800
     *     *     *     *     *     *     *     *     *     *     *     *
   GCCCCAGGGC  TCCTCAGGGG  AGGAGAAGGG  GACCCCCGAC  CCACACTCAG  GGGGTGGAGG
```

FIG.12A2

```
        1810       1820       1830       1840       1850       1860
         *  *       *  *       *  *       *  *       *  *       *  *
     AAGCATCTTG AAAGAAAAAG GCCGGACTTC GGGCTTGTTC AACTTTCAAA AGACAANCAA
        1870       1880       1890       1900       1910       1920
         *  *       *  *       *  *       *  *       *  *       *  *
     NGTACAAGTC GGTGTNCGTC ATTTCCGNAG GAGGAAGGNT GACTGCGTCA TAGGAANTTG
        1930       1940       1950       1960       1970       1980
         *  *       *  *       *  *       *  *       *  *       *  *
     AGGTNGTAAA NTGGNAGTTG ANNTTGGAAA GNNNTCCCCG GATTCCGNTT TCAAAGTTTT
    T
```

FIG. 12A3

```
              10          20          30          40          50          60
               *           *           *           *           *           *    a.a.no.
          CATTGGGTAC GGGCCCCCCT CGAGGTCGAC GGTATCGATA AGCTTGATAT CGAATTCCGG
           H  W  V   R  A  P  L  E  V  D  G  I  D   K  L  D  I   E  F  R>    20
            I  G  Y  G  P  P   S  R  S  T  V  S  I   S  L  I   S  N  S  G>   20
           L  G  T   G  P  P   R  G  R   R  Y  R  *   A  *  Y   R  I  P>     19

70          80          90         100         110         120
               *           *           *           *           *           *
          CTTCACCTGG CCGGGCACCT TCTCTCTGAT TATTGAAGCT CTCCACACAG ATTCTCCTGA
           L  H  L   A  G  H  L  L  S  D  Y  *  S   S  P  H  R   F  S  *>   40
            F  T  W  P  G  T   F  S  L  I   I  E  A  L  H  T   D  S  P  D>  40
           A  S  P   G  R  A   P  S  L  *   L  L  K  L  S  T  Q  I  L  L>   39

130         140         150         160         170         180
               *           *           *           *           *           *
          TGACCTCGCA ACAGAAAACC CAGAAAGACT CATCAGCCGC CTGGCCACCC AGAGGCACCT
           *  P  R   N  K  P  R  K  T   H  Q  P   P  G  H  P   E  A  P>     60
            D  L  A  T  E  N   P  E  R  L  I  S  R   L  A  T   Q  R  H  L>  60
           M  T  S  Q  K  T   Q  K  D  S  S  A  A  W  P  P   R  G  T>       59

190         200         210         220         230         240
               *           *           *           *           *           *
          GACGGTGGGC GAGGAGTGGT CCCAGGACCT GCACAGCAGC GGCCGCACGG ACCTCAAGTA
           D  G  G   R  G  V  V  P  G  P   A  Q  Q   R  P  H  G  P  Q  V>   80
            T  V  G  E  E  W   S  Q  D  L   H  S  S  G  R  T   D  L  K  Y>  80
           *  R  W   A  R  S   G  P  R   T  C  A  A  A  A  R   T  S  S>    79

250         260         270         280         290         300
               *           *           *           *           *           *
          CTCCTACCGC TTCGTGTGTG ACGAACACTA CTACGGAGAG GGCTGCTCCG TTTTCTGCCG
           L  L  P   L  R  V  *  R  T  L   L  R  R   G  L  L  R  F  L  P>  100
            S  Y  R  F  V  C   D  E  H  Y  Y  G  E   G  C  S   V  F  C  R> 100
           T  P  T   A  S  C   V  *  N  T   T  T  E  R  A  A  P  F  S  A>   99

310         320         330         340         350         360
               *           *           *           *           *           *
          TCCCCGGGAC GATGCCTTCG GCCACTTCAC CTGTGGGGAG CGTGCGGAGA AAGTGTGCAA
           S  P  G   R  C  L  R  P  L  H  L  W  G  A  W  G  E   S  V  Q>   120
            P  R  D  D  A  F   G  H  F  T   C  G  E  R  G  E   K  V  C  N> 120
           V  P  G   T  M  P   S  A  T  S   P  V  C  S  V  G   R  K  C  A> 119
```

FIG.12B1

```
              370        380        390        400        410        420
               *  *       *  *       *  *       *  *       *  *       *  *
          CCCTGGCTGG AAAGGGCCCT ACTGCACAGA GCCGATCTGC CTGCCTGGAT GTGATGAGCA
            P  W  L   E  R  A  L   L  H  R   A  D  L   P  A  W  M  *  *  A>  140
           [ P  G  W   K  G  P   Y  C  T  E   P  I  C   L  P  G   C  D  E  Q>] 140
            T  L  A  G   K  G  P   T  A  Q   S  R  S   A  C  L   D  V  M  S>  139

430        440        450        460        470        480
               *  *       *  *       *  *       *  *       *  *       *  *
          GCATGGATTT TGTGACAAAC CAGCCCAATG CAAGTGCAGA GTGGGCTGGC AGGGCCCGTA
            A  W  I  L   *  Q  T   R  G  M   Q  V  Q   S  G  L   A  G  P  V>  160
           [ H  G  F   C  D  K   P  G  E  C   K  C  R   V  G  W   Q  G  R  Y>] 160
            S  M  D  F   V  T  N   Q  G  N   A  S  A  E   W  A  G   R  A  G>  159

490        500        510        520        530        540
               *  *       *  *       *  *       *  *       *  *       *  *
          CTGTGACGAG TGTATCCGCT ATCCAGGCTG TCTCCATGGC ACCTGCCAGC AGCCCTGGCA
            L  *  R   V  Y  P  L   S  R  L   S  P  W   H  L  P   A  A  L  A>  180
           [ C  D  E   C  I  R   Y  P  G  C   L  H  G   T  C  Q   Q  P  W  Q>] 180
            T  V  T  S   V  S  A   I  Q  A   V  S  M  A   P  A  S   S  P  G>  179

550        560        570        580        590        600
               *  *       *  *       *  *       *  *       *  *       *  *
          GTGCAACTGC CAGGAAGGNT GGGGGGGCCT TTTCTGCAAC CAGGACCTGA ACTACTGCAC
            V  Q  L   P  G  R  X   G  G  P   F  L  Q   P  G  P  E   L  L  H> 200
           [ C  N  C   Q  E  G   W  G  G  L   F  C  N   Q  D  L   N  Y  C  T>] 200
            S  A  T  A   R  K  X   G  G  A   F  S  A  T   R  T  *   T  T  A>  199

610        620        630        640        650        660
               *  *       *  *       *  *       *  *       *  *       *  *
          ACACCATAAG CCCTGCAAGA ATCGAGCCAC CTGCAACAAA CACGGGCCAG GGGGAGCTAC
            T  P  *   A  L  Q  E   W  S  H   L  Q  Q   T  R  A  R  G  [ S  Y>] 220
          [ H  H  K   P  C  K   N  G  A  T   C ] N  K   H  G  P   G  G  A  T>  220
            H  T  I  S   P  A  R   M  E  P   P  A  [ T   N  T  G  Q   G ] E  L>  219

670        680        690        700        710        720
               *  *       *  *       *  *       *  *       *  *       *  *
          ACTTGGTCTT TGGCCGGNCT GGGGTACANA GGGTGCCACC TGCGAAGCTT GGGGATTGGA
           [T] W  S   L  A  G  L   G  Y  X   G  C  H   L  R  S   L  G  I  G>  240
            L  G  L   W  P  X  W   G  T  X   G  A  T   C  E  A   W  G  L  D>  240
            H  L  V  F   G  R  X   C  V  X   R  V  P   P  A  K   L  G  D  W>  239
```

FIG.12B2

```
         730        740        750        760        770        780
          *    *     *    *     *    *     *    *     *    *     *    *
      CGAGTTGTTG ACCCCAGCCC TTGGTAAGAA CGGAGGGAGC TTGACGGATC TTCGGAGAAC
       R  V  V  D │P  S  P │W  *  E  R  R  E  L  D  G  S  S │E  N>│ 260
       E  L  L  T  P  A  L  G │K  N  G  G  S  L  T  D  L │R  R  T>  260
       T  S  C  *  P  Q  P  L  V  R  T  E  Q  A  *  R  I  F  G  E>  259

790        800        810        820        830        840
          *    *     *    *     *    *     *    *     *    *     *    *
      AGCTACTCCT GTACCTGCCC ACCCGGCTTC TACGGCAAAA TCTGTGAATT GAGTGCCATG
      │S  Y  S  C  T  C  P  P  G  F  Y  G  K  I  C  E  L  S  A  M>│ 280
       A  T  P  V  P  A  H  P  A  S  T  A  K  S  V  N  *  V  P  *>  280
       Q  L  L  Y  L  P  T  R  L  L  R  Q  N  L  *  I  E  C  H>     279

850        860        870        880        890        900
          *    *     *    *     *    *     *    *     *    *     *    *
      ACCTGTGCGG ACGGCCCTTG CTTTAACGGG GGTCGGTGCT CAGACAGCCC CGATGGAGGG
      │T  C  A  D  G  P  C  F  N  G  G  R  C  S  D  S  P  D  G  G>│ 300
       P  V  R  T  A  L  A  L  T  G  V  G  A  Q  T  A  P  M  E  G>  300
       D  L  C  G  R  P  L  L  *  R  G  S  V  L  R  Q  P  R  W  R>  299

910        920        930        940        950        960
          *    *     *    *     *    *     *    *     *    *     *    *
      TACAGCTGCC GCTGCCCCGT GGGCTACTCC GGCTTCAACT GTGAGAAGAA AATTGACTAC
      │Y  S  C  R  C  P  V  G  Y  S  G  F  N  C  E  K  K  I  D  Y>│ 320
       T  A  A  A  A  P  W  A  T  P  A  S  T  V  R  R  K  L  T  T>  320
       V  Q  L  P  L  P  R  G  L  L  R  L  Q  L  *  E  E  N  *  L>  319

970        980        990       1000       1010       1020
          *    *     *    *     *    *     *    *     *    *     *    *
      TGCAGCTCTT CACCCTGTTC TAATGGTGCC AAGTGTGTGG ACCTCGGTGA TGCCTACCTG
      │C  S  S  S  P  C  S  N  G  A  K  C  V  D  L  G  D  A  Y  L>│ 340
       A  A  L  H  P  V  L  M  V  P  S  V  W  T  S  V  M  P  T  C>  340
       L  Q  L  F  T  L  F  *  W  C  Q  V  C  G  P  R  *  C  L  P>  339

1030       1040       1050       1060       1070       1080
          *    *     *    *     *    *     *    *     *    *     *    *
      TGCCGCTGCC AGGCCGGCTT CTCGGGGAGG CACTGTGACG ACAACGTGGA CGACTGCGCC
      │C  R  C  Q  A  G  F  S  G  R  H  C  D  D  N  V  D  D  C  A>│ 360
       A  A  A  R  P  A  S  R  G  G  T  V  T  T  T  W  T  T  A  P>  360
       V  P  L  P  G  R  L  L  G  E  A  L  *  R  Q  G  R  L  R>     359
```

FIG.12B3

```
         1090       1100       1110       1120       1130       1140
       *    *    *    *    *    *    *    *    *    *    *    *
     TCCTCCCCGT GCCCCAACGG GGGCACCTGC CGGGATGGCG TGAACGACTT CTCCTGCACC
      S  S  P   C  A  N  G   G  T  C   R  D  G   V  N  D  F   S  C  T>   380
      P  P  R   A  P  T   G  A  P  A   G  M  A   *  T  T    S  P  A  P>  380
      L  L  P  V  R  Q  R   G  H  L   P  G  W  R   E  R  L   L  L  H>    379

1150       1160       1170       1180       1190       1200
       *    *    *    *    *    *    *    *    *    *    *    *
     TGCCCGCCTG GCTACACGGG CAGGAACTGC AGTGCCCCCG CCAGCAGGTG CGAGCACGCA
      C  P  P   G  Y  T  G   R  N  C   S  A  P   A  S  R   C  E  H  A>   400
      A  R  L   A  T  R   A  G  T   A  V  P  P   P  A  G   A  S  T  H>   400
      L  P  A  W  L  H  G   Q  E  L   Q  C  P  R   Q  Q  V   R  A  R>    399

1210       1220       1230       1240       1250       1260
       *    *    *    *    *    *    *    *    *    *    *    *
     CCCTGCCACA ATGGGGCCAC CTGCCACGAG AGGGGCCACC GCTATNTGTG CGAGTGTGCC
      P  C  H   N  G  A  T   C  H  E   R  G  H  R  Y  X   C  E  C  A>    420
      P  A  T   M  G  P   P  A  T  R   G  A  T   A  I    C  A  S  V  P>  420
      T  L  P  Q  W  G  H   L  P  R   E  G  P  P   L  F  V   R  V  C>    419

1270       1280       1290       1300       1310       1320
       *    *    *    *    *    *    *    *    *    *    *    *
     CGAAGCTACG GGGGTCCCAA CTGCCANTTC CTGCTCCCCG AAACTGCCCC CCCGGCCCCA
      R  S  Y   G  G  P  N   C  X   F  L  L  P  E   T  A  P   P  A  P>   440
      E  A  T   G  V  P   T  A  X   S  C  S  P   K  L  P   P  R  P  H>   440
      P  K  L  R   G  S  Q   L  P  X   P  A  P  R   N  C  P  P  G  P>    439

1330       1340       1350       1360       1370       1380
       *    *    *    *    *    *    *    *    *    *    *    *
     CGGTGGTGGA AACTCCCCTA AAAAAACCTA AAAGGGCCGG GGGGGGCCCA TCCCCTTGGT
      R  W  W   K  L  P   *  K  N  L   K  G  P   G  G  A  H   P  L  G>   460
      G  G   N  S  P   K  K  T   *  K  G  R   G  G  P   I  P  L  V>      460
      T  V  V  E   T  P  L   K  K  P   K  R  A  G   G  G  P   S  P  W>   459

1390       1400       1410       1420       1430       1440
       *    *    *    *    *    *    *    *    *    *    *    *
     GGACGTGTGC GCCCGGCGTCA TCCTTGTCCT CATGCTCCTG CTCGGCTGTC CGCTGTGGT
      G  R  V   R  R  G  H   P  C  P   H  A  A   A  G  L   C  R  C  G>   480
      D  V  C   A  G  V   I  L  V  L   M  L  L   L  G  C   A  A  V  V>   480
      W  T  C  A   P  G  S   S  L  S   S  C  C  C   W  A  V   P  L  W>   479
```

FIG.12B4

```
          1450       1460       1470       1480       1490       1500
           *    *     *    *     *    *     *    *     *    *     *    *
        GGTCTGCGTC CGGCTGAGGC TGCAGAAGCA CCGGCCCCCA GCCGACCCCT GNCGGGGGGA
         G  L  R   P  A  E  A   A  E  A   P  A  P   S  R  P  L  X  G  C>  500
         V  C  V   R  L  R  L   Q  K  H   R  P  P   A  D  P  X  R  G  E>  500
        W  S  A  S  G  *  G   C  R  S   T  G  P   Q  P  T  P   X  G  G>   499

1510       1520       1530       1540       1550       1560
           *    *     *    *     *    *     *    *     *    *     *    *
        GACGGAGACC ATGAACAACC TGGNCAACTG CCAGCGTCAG AAGGACATCT CAGTCAGCAT
         D  C  D   H  E  Q  P   G  Q  L   P  A  *   E  G  H  L  S  Q  H>  520
         T  E  T   M  N  N  L  X  N  C   Q  R  E   K  D  I  S  V  S  I>   520
        R  R  R  P  *  T  T   W  X  T   A  S  V   R  R  T  S   Q  S  A>   519

1570       1580       1590       1600       1610       1620
           *    *     *    *     *    *     *    *     *    *     *    *
        CATCGGGGNC ACGCAGATCA AGAACACCAA CAAGAAGGCG GACTTCCACG GGGACCACAG
         H  R  G   H  A  D  Q   E  H  Q   Q  E  G   G  L  P  R  G  P  Q>  540
         I  G  X   T  Q  I   K  N  T  N   K  K  A   D  F  H  G  D  H  X>  540
        S  S  G  X  R  R  S   R  T  P   T  R  R   R  T  S  T   G  T  T>   539

1630       1640       1650       1660       1670       1680
           *    *     *    *     *    *     *    *     *    *     *    *
        NGCCGACAAG AATGGCTTCA AGGCCCGCTA CCCAGNGGTG GACTATAACC TCGTGCAGGA
         X  R  Q   E  W  L  Q   G  P  L   P  X  G   L  *  P  R  A  G>     560
         A  D  K   N  G  F  K   A  R  Y  P  X  V   D  Y  N  L  V  Q  D>   560
        X  P  T  R  M  A  S   R  P  A   T  Q  X   W  T  I  T   S  C  R>   559

1690       1700       1710       1720       1730       1740
           *    *     *    *     *    *     *    *     *    *     *    *
        CCTCAAGGGT GACGACACCG CCGTCAGGGA CGCGCACAGC AAGCGTGACA CCAAGTGNCA
         P  Q  G   *  R  H  R   R  Q  G   R  A  Q   Q  A  *  H  Q  V  X>  580
         L  K  G   D  D  T  A  V  R  D   A  H  S   K  R  D  T  K  X  Q>   580
        T  S  R  V  T  T  P   P  S  G   T  R  T   A  S  V  T   P  S  X>   579

1750       1760       1770       1780       1790       1800
           *    *     *    *     *    *     *    *     *    *     *    *
        GCCCCAGGGC TCCTCAGGGG AGGAGAAGGG GACCCCCGAC CCACACTCAG GGGGTGGAGG
         A  P  G   L  L  R  G   G  E  G   D  P  R  P  T  L  R  G  W  R>   600
         P  Q  G   S  S  G  E   E  K  G   T  P  D   P  H  S  G  G  G  G>  600
        S  P  R  A  P  Q  G   R  R  R   G  P  P   T  H  T  Q   G  V  E>   599
```

FIG.12B5

```
              1810       1820       1830       1840       1850       1860
                *  *      *  *      *  *      *  *      *  *      *  *
            AAGCATCTTG AAAGAAAAAG GCCGGACTTC GGGCTTGTTC AACTTTCAAA AGACAANCAA
             K  H  L  E  R  K  R  P  D  F  G  L  V  Q  L  S  K  D  X  Q>  620
             S  I  L  K  E  K  G  R  T  S  G  L  F  N  F  Q  K  T  X  X>  620
             E  A  S  *  K  K  K  A  G  L  R  A  C  S  T  F  K  R  Q  X>  619

1870       1880       1890       1900       1910       1920
                *  *      *  *      *  *      *  *      *  *      *  *
            NGTACAAGTC GGTGTNCGTC ATTTCCGNAG GAGGAAGGNT GACTGCGTCA TAGGAANTTG
             X  T  S  R  C  X  S  F  P  X  E  E  G  *  L  R  H  R  X  L>  640
             V  Q  V  G  V  R  H  F  R  R  R  K  X  D  C  V  I  G  X  *>  640
             X  Y  K  S  V  X  V  I  S  X  G  G  R  X  T  A  S  *  E  X>  639

1930       1940       1950       1960       1970       1980
                *  *      *  *      *  *      *  *      *  *      *  *
            AGGTNGTAAA NTGGNAGTTG ANNTTGGAAA GNNNTCCCCC GATTCCCNTT TCAAAGTTTT
             R  X  *  X  G  S  *  X  W  K  X  X  P  G  F  R  F  Q  S  F>  660
             G  X  K  X  X  V  X  X  G  K  X  S  P  D  S  X  F  K  V  F>  660
             E  V  V  X  W  X  L  X  L  E  X  X  P  R  I  P  X  S  K  F>  659
```

FIG.12B6

```
MOUSE DELTA DNA   GTCCAGCGGT  ACCATGGCC   GTCGGAGCGC  GCTAGCCCTT  GCCGTGGTCT   50
HUMAN DELTA       ----------  ----------  ----------  ----------  ----------

CONSENSUS         GTCCAGCGGT  ACCATGGGCC  GTCGGAGCGC  GCTAGCCCTT  GCCGTGGTCT   50

MOUSE DELTA DNA   CTGCCCTGCT  GTGCCAGGTC  TGGAGCTCCG  GCGTATTTGA  GCTGAAGCTG  100
HUMAN DELTA       ----------  ----------  ----------  ----------  ----------

CONSENSUS         CTGCCCTGCT  GTGCCAGGTC  TGGAGCTCCG  GCGTATTTGA  GCTGAAGCTG  100

MOUSE DELTA DNA   CAGGAGTTCG  TCAACAAGAA  GGGGCTGCTG  GGGAACCGCA  ACTGCTGCCG  150
HUMAN DELTA       ----------  ----------  ----------  ----------  ----------

CONSENSUS         CAGGAGTTCG  TCAACAAGAA  GGGGCTGCTG  GGGAACCGCA  ACTGCTGCCG  150

MOUSE DELTA DNA   CGGGGGCTCT  GGCCCGCCTT  GCGCCTGCAG  GACCTTCTTT  CGCGTATGCC  200
HUMAN DELTA       ----------  ----------  ----------  ----------  ----------

CONSENSUS         CGGGGGCTCT  GGCCCGCCTT  GCGCCTGCAG  GACCTTCTTT  CGCGTATGCC  200

MOUSE DELTA DNA   TCAAGCACTA  CCAGGCCAGC  GTGTCACCGG  AGCCACCCTG  CACCTACGGC  250
HUMAN DELTA       ----------  ----------  ----------  ----------  ----------

CONSENSUS         TCAAGCACTA  CCAGGCCAGC  GTGTCACCGG  AGCCACCCTG  CACCTACGGC  250

MOUSE DELTA DNA   AGTGCTGTCA  CGCCAGTGCT  GGGTGTCGAC  TCCTTCAGCC  TGCCTGATGG  300
HUMAN DELTA       ----------  ----------  ----------  ----------  -----CATTG    5

CONSENSUS         AGTGCTGTCA  CGCCAGTGCT  GGGTGTCGAC  TCCTTCAGCC  TGCCTSATKG  300

MOUSE DELTA DNA   CGCAGCATC   GACCCG---G  CCTTCAGCAA  CCCCA--TCC  GATTTCCCC   343
HUMAN DELTA       GGTACGGCC   CCCCTCGAGG  TTGACGGTAT  CGATAAGCTT  GATATCGAAT   55

CONSENSUS         SGYASGSRYC  SMCCYCGAGG  YCKWCRGYAW  CSMYAAGYYY  GATATCGMMY  350

MOUSE DELTA DNA   TTCGGCTTCA  CCTGGCCAGG  TACCTTCTCT  CTGATCATTG  AAGCCCTCCA  393
HUMAN DELTA       TCCGGCTTCA  CCTGGCCGGG  CACCTTCTCT  CTGATTATTG  AAGCTCTCCA  105

CONSENSUS         TYCGGCTTCA  CCTGGCCRGG  YACCTTCTCT  CTGATYATTG  AAGCYCTCCA  400

MOUSE DELTA DNA   TACAGACTCT  CCGGATGACC  TCGCAACAGA  AAACCCAGAA  AGACTCATCA  443
HUMAN DELTA       CACAGATTCT  CCTGATGACC  TCGCAACAGA  AAACCCAGAA  AGACTCATCA  155

CONSENSUS         YACAGAYTCT  CCYGATGACC  TCGCAACAGA  AAACCCAGAA  AGACTCATCA  450
```

FIG.13A

| | | |
|---|---|---|
| MOUSE DELTA DNA | GCCGCCTGAC CACACAGAGG CACCTCACTG TGGGAGAAGA ATGGTCTCAG | 493 |
| HUMAN DELTA | GCCGCCTGGC CACCCAGAGG CACCTGACGG TGGGCAGGA GTGGTCCCAG | 205 |
| CONSENSUS | GCCGCCTGRC CACMCAGAGG CACCTSACKG TGGGMGARGA RTGGTCYCAG | 500 |
| MOUSE DELTA DNA | GACCTTCACA GTAGCGGCCG CACAGACCTC CGGTACTCTT ACCGCTTTGT | 543 |
| HUMAN DELTA | GACCTGCACA GCAGCGGCCG CACGGACCTC AAGTACTCCT ACCGCTTCGT | 255 |
| CONSENSUS | GACCTKCACA GYAGCGGCCG CACRGACCTC MRGTACTCYT ACCGSTTYGT | 550 |
| MOUSE DELTA DNA | GTGTGACGAG CACTACTACG GAGAAGGTTG CTCTGTCTTC TGCCGACCTC | 593 |
| HUMAN DELTA | GTGTGACGAA CACTACTACG GAGAGGCTG CTCCGTTTTC TGCCGTCCCC | 305 |
| CONSENSUS | GTGTGACGAR CACTACTACG GAGARGGYTG CTCYGTKTTC TGCCGWCCYC | 600 |
| MOUSE DELTA DNA | GGGATGACGC CTTTGGCCAC TTCACCTGCG GGACAGAGG GGAGAAGATG | 643 |
| HUMAN DELTA | GGGACGATGC CTTCGGCCAC TTCACCTGTG GGAGCCGTGG GGAGAAACTG | 355 |
| CONSENSUS | GGGAYGAYGC CTTYGGCCAC TTCACCTGYG GGASMGWGG GGAGAARRTG | 650 |
| MOUSE DELTA DNA | TGCCACCCTG GCTGGAAAGG CCAGTACTGC GCTGACCCAA TCTGTCTGCC | 693 |
| HUMAN DELTA | TGCAACCCTG GCTGGAAAGG GCCCTACTGC ACAGACCCGA TCTGCCTGCC | 405 |
| CONSENSUS | TGCRACCCTG GCTGGAAAGG SCMSTACTGC ACWGASCCRA TCTGYCTGCC | 700 |
| MOUSE DELTA DNA | AGGGTGTGAT GACCAACATG GATACTGTGA CAAACCAGGG GAGTGCAAGT | 743 |
| HUMAN DELTA | TGGATGTGAT GACCAGCATG GATTTTGTGA CAAACCAGGG GAATGCAAGT | 455 |
| CONSENSUS | WGGRTGTGAT GASCARCATG GATWYTGTGA CAAACCAGGG GARTGCAAGT | 750 |
| MOUSE DELTA DNA | GCAGAGTTGG CTGGCAGGGC CGGTACTGCG ATGAGTGCAT CCGATACCCA | 793 |
| HUMAN DELTA | GCAGAGTGGG CTGGCAGGGC CGTTACTGTG ACGAGTGTAT CCGCTATCCA | 505 |
| CONSENSUS | GCAGAGTKGG CTGGCAGGGC CGSTACTGYS AYGAGTGYAT CCGMTAYCCA | 800 |
| MOUSE DELTA DNA | GGTTGTCTCC ATGGCACCTG CCAGCAACCC TGGCAGTGTA ACTGCCAGGA | 843 |
| HUMAN DELTA | GCCTGTCTCC ATGGCACCTG CCAGCAGCCC TGGCAGTGCA ACTGCCAGGA | 555 |
| CONSENSUS | GGYTGTCTCC ATGGCACCTG CCAGCARCCC TGGCAGTGYA ACTGCCAGGA | 850 |
| MOUSE DELTA DNA | AGGCTGGGGG GGCCTTTTCT GCAACCAAGA CCTGAACTAC TGTACTCACC | 893 |
| HUMAN DELTA | AGGNTGGGGG GGCCTTTTCT GCAACCAGGA CCTGAACTAC TGCACACACC | 605 |
| CONSENSUS | AGGNTGGGGG GGCCTTTTCT GCAACCARGA CCTGAACTAC TGYACMCACC | 900 |

FIG.13B

```
MOUSE DELTA DNA  ATAAGCCGTG CAGGAATGGA GCCACCTGCA CCAACACGG GCCAGGGGA   941
HUMAN DELTA      ATAAGCCCTG CAAGAATGGA GCCACCTGCA ACAAACACGG GCCAGGGGCA  655

CONSENSUS        ATAAGCCSTG CARGAATGGA GCCACCTGCA ACMAACACGG GCCAGGGGCA  950

MOUSE DELTA DNA  GCTACACATG TTCCTT-GCC GACCTGGGT ATACA-CGTG CCAACTGTG-   986
HUMAN DELTA      GCTACACTTG GTCTTTGCCC CGNCTGGGT ADANAGGGTG CCACCTGCGA    705

CONSENSUS        GCTACACWTG KTCYTTGCCC CGNCYKGGGT AMANAGGGTG CCAMCTGYGA  1000

MOUSE DELTA DNA  AGCT--GGAA GTAGATGAG- TG-TGCTCCT AGCCCGT-GC AAGAACGGAG   1031
HUMAN DELTA      AGCTTGGCGA TTCGACGAGT TGTTGACCCC AGCCCTTGGT AAGAACGGAG   755

CONSENSUS        AGCTTGGCGRA KTRGAYGAGT TGTTGMYCCY AGCCCYTGCY AAGAACGGAG  1050

MOUSE DELTA DNA  CGAGCTGCAC GGACCTT-G AGGACAGCTT CTCTTGCACC TGCCCTCCCG    1079
HUMAN DELTA      CGAGCTTGAC GGATCTTCGG AGAACAGCTA CTCCTGTACC TGCCCACCCG    805

CONSENSUS        SGAGCTKSAC GGAMCTTCGG AGRACAGCTW CTCYTGYACC TGCCCWCCCG  1100

MOUSE DELTA DNA  GCTTCTATGG CAAGGTCTGT GAGCTGAGCG CCATGACCTG TGCAGATGC    1129
HUMAN DELTA      GCTTCAACGG CAAAATCTGT GAATTGAGTG CCATGACCTG TGCCGACGGC   855

CONSENSUS        GCTTCTAYGG CAARRTCTGT GARYTGAGYG CCATGACCTG TGCRGAYGGC  1150

MOUSE DELTA DNA  CCTTGCTTCA ATGGAGGACG ATGTTCAGAT AACCCTGACG GAGGCTACAC    1179
HUMAN DELTA      CCTTGCTTTA ACGGCGGTCG GTGCTCAGAC AGCCCCGATG GAGGGTACAG    905

CONSENSUS        CCTTGCTTYA AYGGRGGWCG RTGYTCAGAY ARCCCYGAYG GAGGSTACAS  1200

MOUSE DELTA DNA  CTGCCATTGC CCCTTGGGCT TCTCTGGCTT CAACTGTGAG AAGAAGATGG    1229
HUMAN DELTA      CTGCCGCTGC CCCGTGGGCT ACTCCGGCTT CAACTGTGAG AAGAAAATTG     955

CONSENSUS        CTGCCRYTGC CCCKTGGGCT WCTCYGGCTT CAACTGTGAG AAGAARATKG  1250

MOUSE DELTA DNA  ATCTCTGCCG CTCTTCCCCT TGTTCTAACG GTGCCAAGTG TGTGGACCTC   1279
HUMAN DELTA      ACTACTGCCAG CTCTTCACCC TGTTCTAATG GTGCCAAGTG TGTGGACCTC  1005

CONSENSUS        AYYWCTGCRG CTCTTCMCCY TGTTCTAAYG GTGCCAAGTG TGTGGACCTC  1300

MOUSE DELTA DNA  GGCAACTCTT ACCTGTGCCG CTGCCAGGCT GGCTTCTCCG GCAGGTACTG    1329
HUMAN DELTA      GGTGATGCCT ACCTGTGCCG CTGCCAGGCC GGCTTCTCGG GAGGCACTG    1055

CONSENSUS        GGYRAYKCYT ACCTGTGCCG CTGCCAGGCY GGCTTCTGSS GGAGGYACTG  1350

MOUSE DELTA DNA  CGACGACAAT GTGGATGACT GTCCCTCCTC CCCGTGTGCA AATGCGGGCA    1379
HUMAN DELTA      TGACGACAAC GTGGACGACT GCCCCTCCTC CCCGTGCCCC AACGGGGGCA    1105

CONSENSUS        YGASGACAAY GTGGAYGACY GYCCCTCCTC CCCGTGYGCM AAYGGGGGCA  1400
```

FIG. 13C

```
MOUSE DELTA DNA  CCTGCCGGGA CAGTGTGAAC GACTTCTCCT GTACCTGCCC ACCTGGCTAC  1429
HUMAN DELTA      CCTGCCGGGA TGGCGTGAAC GACTTCTCCT GCACCTGCCC GCCTGGCTAC  1155

CONSENSUS        CCTGCCGGGA YRGYGTGAAC GACTTGTCCT GYACCTGCCC RCCYGGCTAC  1450

MOUSE DELTA DNA  ACGGGCAAGA ACTGCAGCGC CCCTGTCAGC AGGTCTGAGC ATGCACCCTG  1479
HUMAN DELTA      ACGGGCAGGA ACTGCAGTGC CCCCGCCAGC AGGTCCGAGC ACGCACCCTG  1205

CONSENSUS        ACGGGCARGA ACTGCAGYGC CCCYGYCAGC AGGTCYGAGC AYGCACCCTG  1500

MOUSE DELTA DNA  CCATAATGGG GCCACCTGCC ACCAGAGGGG CCAGCGCTAC ATGTGTGAGT  1529
HUMAN DELTA      CCACAATGGG GCCACCTGCC ACGAGAGGGG CCACCGCTAT TTGTGCGAGT  1255

CONSENSUS        CCAYAATGGG GCCACCTGCC ACSAGAGGGG CCASCGCTAY WTGTGYGAGT  1550

MOUSE DELTA DNA  GCGCCCAGGG CTATGGCGGC CCCAACTGCC AGTTTCTGCT CCCTGHAGCC  1578
HUMAN DELTA      GTGCCCGAAG CTACGGGGGT CCCAACTGCC ANTTCCTGCT CCCCGAAACT  1305

CONSENSUS        GYGCCCRRRG CTAYGGSGGY CCCAACTGCC ANTTYCTGCT CCCYGHARCY  1600

MOUSE DELTA DNA  -ACCACCAGG GCCCATGGTG GTGGHADCTC AGTGAGACGC ATATHGGAGA  1625
HUMAN DELTA      GCCCCCCCGG CCCCACGGTG GTGGAAACTC CCCTAAAAAA ACCTAAAAGG  1355

CONSENSUS        GMCCMCCMGG SCCCAYGGTG GTGGAAMCTC MSYKARARRM AYMTARRACR  1650

MOUSE DELTA DNA  GCCAGGGCGG GCCCTTCCCC TGGGTGGCCG TGTGTGCCGG GGTGGTGCTT  1675
HUMAN DELTA      GCCGGGGCGG GCCCATCCCC TTGGTGGACG TGTGCGCCGG GGTCATCCTT  1405

CONSENSUS        GCCRGGSGG GCCCWTCCCC TKGGTGGMCG TGTGYGCCGG GGTSRTSCTT  1700

MOUSE DELTA DNA  GTCCTCCTGC TGCTGCTGGG CTGTGCTGCT GTGGTGGTCT GCGTCCGGCT  1725
HUMAN DELTA      GTCCTCATGC TGCTGCTGGG CTGTGCCGCT GTGGTGGTCT GCGTCCGGCT  1455

CONSENSUS        GTCCTCMTGC TGCTGCTGGG CTGTGCYGCT GTGGTGGTCT GCGTCCGGCT  1750

MOUSE DELTA DNA  GAAGCTACAG AAACACCAGC CTCCATCTGA ACCCTGTGGG GGAGAGACAG  1775
HUMAN DELTA      GAGGCTGCAG AAGCACCGGC CCCCATCCGA CCCCTGNCGG GGGGAGACGG  1505

CONSENSUS        GARGCTRCAG AARCACCRGC CYCCASCYGA MCCCTGNSGG GGRGAGACRG  1800

MOUSE DELTA DNA  AAACCATGAA CAACCTAGCC AATTGCCAGC GCGAGAAGGA CGTTTCTGTT  1825
HUMAN DELTA      AGACCATGAA CAACCTGGNC AACTGCCAGC GTGAGAAGGA CATCTCAGTC  1555

CONSENSUS        ARACCATGAA CAACCTRGNC AAYTGCCAGC GYGAGAAGGA CRTYTCWGTY  1850
```

FIG.13D

```
MOUSE DELTA DNA  AGCATCATTG GGGCTACCCA GATCAAGAAC ACCAACAAGA AGGCGGACTT  1875
HUMAN DELTA      AGCATCATCG GGNCACGCA GATCAAGAAC ACCAACAAGA AGGCGGACTT  1605

CONSENSUS        AGCATCATYG GGNYACSCA GATCAAGAAC ACCAACAAGA AGGCGGACTT  1900

MOUSE DELTA DNA  TCACGGGGAC CATGGAGCCA AGAAGAGCAG CTTTAAGGTC CGATACCCCA  1925
HUMAN DELTA      CCACGGGGAC CACAGNGCCG AGAAGAATGG CTTCAAGGCC CGCTACCCAG  1655

CONSENSUS        YCACGGGGAC CAYRGNGCCR ASAAGARYRG CTTYAAGGYC CGMTACCCMR  1950

MOUSE DELTA DNA  CTGTGGACTA TAACCTCGTT CGAGACCTCA AGGGAGATGA AGCCACGGTC  1975
HUMAN DELTA      NGGTGGACTA TAACCTCGTG CAGGACCTCA AGGGTGACGA CACCGCCGTC  1705

CONSENSUS        NKCTGGACTA TAACCTCGTK CRRGACCTCA AGGGNGAYGA MRCCRCSGTC  2000

MOUSE DELTA DNA  AGGGATACAC ACAGCAAACG TGACACCAAG TGCCAGTCAC AGAGCTCTGC  2025
HUMAN DELTA      AGGGACGCGC ACAGCAAGCG TGACACCAAG TGNCAGCCCC AGGGCTCCTC  1755

CONSENSUS        AGGGAYRCRC ACAGCAAFCG TGACACCAAG TGNCAGYCMC AGRGCTCYKC  2050

MOUSE DELTA DNA  AGGAGAAGAG AA--GATCG CC--CCAACA CTTTA-GGGT GG-GG-AGAT  2067
HUMAN DELTA      AGGCGACGAG AAGGCGACCC CCGACCCACA CTCAGGGGGT GGAGGAAGCA  1805

CONSENSUS        AGGRGARGAG AAGGGGAYCS CCGACCMACA CTYAGGGGGT GGAGGAAGMW  2100

MOUSE DELTA DNA  TCCTGACAGA AAAAGGCCAG AGTCT-GTC TACTCTAC-T TCAAAGGAC-  2113
HUMAN DELTA      TCTTGAAAGA AAAAGGCCGG ACTTCGGCCT TGTTCAACTT TCAAAGACA  1855

CONSENSUS        TCYTGAMAGA AAAAGGCCRG ASTYYGGCYY TRYTCWACTT TCAAARGACA  2150

MOUSE DELTA DNA  -ACCAAGTAC CAGTCGGTGT ATGTTCTGTC TGCAGAA--A AGGATGAGTG  2160
HUMAN DELTA      ANCAANGTAC AAGTCGGTGT NCGTCATTTC CGNAGGAGGA AGGNTGACTG  1905

CONSENSUS        ANCMANGTAC MAGTCGGTGT NYGTYMTKTC YGNAGRAGGA AGGNTGASTG  2200

MOUSE DELTA DNA  TGTTATA-GC GACTGAGGT- GTAAGATGGA AGCGATTGTG CAAAATTCCC  2208
HUMAN DELTA      CGTCATAGGA ANTTGAGGTN GTAAANTGGN AG---T-TG- --ANNTT---  1945

CONSENSUS        YGTYATAGGM RNYTGAGCTN GTAARNTGGN AGCGATTGTG CAANNTTCCC  2250

MOUSE DELTA DNA  ATTTCTCTCA AATAAAATTC CAAGGATATA GCCCCGATTGA ATGCTGCTGA  2258
HUMAN DELTA      -------GGA AAGNNN- TC CCCGGAT--- -TCCGNT--- ---TTC----  1972

CONSENSUS        ATTTCTCKSA AAKNNNATTC CMMGGATATA GCYCCGNTGA ATGCTKCTGA  2300
```

FIG.13E

```
MOUSE DELTA DNA  GAGAGGAAGG GAGAGGAAAC CCAGGGACTG CTGCTGAGAA CCAGGTTCAG  2308
HUMAN DELTA      ---------- ------AAA- ---------G TTTTT----- ----------  1981

CONSENSUS        GAGAGGAAGG GAGAGGAAAC CCAGGGACTG YTKYTCAGAA CCAGGTTCAG  2350

MOUSE DELTA DNA  GCGAAGCTGG TTCTCTCAGA GTTAGCAGAG GCGCCCGACA CTGCCAGCCT  2358
HUMAN DELTA      ---------- ---------- ---------- ---------- ----------  1981

CONSENSUS        GCGAAGCTGG TTCTCTCAGA GTTAGCAGAG GCGCCCGACA CTGCCAGCCT  2400

MOUSE DELTA DNA  AGGCTTTGGC TGCCGCTGGA CTGCCTGCTG GTTGTTCCCA TTGCACTATG  2408
HUMAN DELTA      ---------- ---------- ---------- ---------- ----------  1981

CONSENSUS        AGGCTTTGGC TGCCGCTGGA CTGCCTGCTG GTTGTTCCCA TTGCACTATG  2450

MOUSE DELTA DNA  GACAGTTGCT TTGAAGAGTA TATATTTAAA TGGACGAGTG ACTTGATTCA  2458
HUMAN DELTA      ---------- ---------- ---------- ---------- ----------  1981

CONSENSUS        GACAGTTGCT TTGAAGAGTA TATATTTAAA TGGACGAGTG ACTTGATTCA  2500

MOUSE DELTA DNA  TATAGGAAGC ACGCACTGCC CACACGTCTA TCTTGGATTA CTATGAGCCA  2508
HUMAN DELTA      ---------- ---------- ---------- ---------- ----------  1981

CONSENSUS        TATAGGAAGC ACGCACTGCC CACACGTCTA TCTTGGATTA CTATGAGCCA  2550

MOUSE DELTA DNA  GTCTTTCCTT GAACTAGAAA CACAACTGCC TTTATTGTCC TTTTTGATAC  2558
HUMAN DELTA      ---------- ---------- ---------- ---------- ----------  1981

CONSENSUS        GTCTTTCCTT GAACTAGAAA CACAACTGCC TTTATTGTCC TTTTTGATAC  2600

MOUSE DELTA DNA  TGAGATGTGT TTTTTTTTTT CCTAGACGGG AAAAAGAAAA CGTGTGTTAT  2608
HUMAN DELTA      ---------- ---------- ---------- ---------- ----------  1981

CONSENSUS        TGAGATGTGT TTTTTTTTTT CCTAGACGGG AAAAAGAAAA CGTGTGTTAT  2650

MOUSE DELTA DNA  TTTTTTGGGA TTTGTAAAAA TATTTTTCAT GATATCTGTA AAGCTTGAGT  2658
HUMAN DELTA      ---------- ---------- ---------- ---------- ----------  1981

CONSENSUS        TTTTTTGGGA TTTGTAAAAA TATTTTTCAT GATATCTGTA AAGCTTGAGT  2700

MOUSE DELTA DNA  ATTTGTGAC GTTCATTTTT TTATAATTTA AATTTTGGTA AATATGTACA  2708
HUMAN DELTA      ---------- ---------- ---------- ---------- ----------  1981

CONSENSUS        ATTTGTGAC GTTCATTTTT TTATAATTTA AATTTTGGTA AATATGTACA  2750
```

FIG.13F

```
MOUSE DELTA DNA  AAGGCACTTC GGGTCTATGT GACTATATTT TTTTGTATAT AAATGTATTT  2758
HUMAN DELTA      ---------- ---------- ---------- ---------- ----------  1981

CONSENSUS        AAGGCACTTC GGGTCTATGT GACTATATTT TTTTGTATAT AAATGTATTT  2800

MOUSE DELTA DNA  ATGGAATATT GTGCAAATGT TATTTGAGTT TTTTACTGTT TTGTTAATGA  2808
HUMAN DELTA      ---------- ---------- ---------- ---------- ----------  1981

CONSENSUS        ATGGAATATT GTGCAAATGT TATTTGAGTT TTTTACTGTT TTGTTAATGA  2850

MOUSE DELTA DNA  AGAAATTCAT TTTAAAAATA TTTTTCCAAA ATAAATATAA TGAACTACA  2857
HUMAN DELTA      ---------- ---------- ---------- ---------- ---------  1981

CONSENSUS        AGAAATTCAT TTTAAAAATA TTTTTCCAAA ATAAATATAA TGAACTACA  2899
```

NUCLEOTIDE AND PROTEIN SEQUENCES OF VERTEBRATE DELTA GENES AND METHODS BASED THEREON

The present application is a divisional application of application Ser. No. 08/981,392, filed Apr. 8, 1998, now U.S. Pat. No. 6,262,025, national stage of International Application No. PCT/US96/11178 filed Jun. 28, 1996 (published in English), which claims the benefit of U.S. Provisional Application Serial No. 60/000,589 filed Jun. 28, 1995, each of which is incorporated by reference herein in its entirety.

INTRODUCTION

The present invention relates to vertebrate Delta genes and their encoded protein products, as well as derivatives and analogs thereof. Production of vertebrate Delta proteins, derivatives, and antibodies is also provided. The invention further relates to therapeutic compositions and methods of diagnosis and therapy.

BACKGROUND OF THE INVENTION

Genetic analyses in Drosophila have been extremely useful in dissecting the complexity of developmental pathways and identifying interacting loci. However, understanding the precise nature of the processes that underlie genetic interactions requires a knowledge of the protein products of the genes in question.

The vertebrate central nervous system is an intimate mixture of different cell types, almost all generated from the same source—the neurogenic epithelium that forms the neural plate and subsequently the neural tube. What are the mechanisms that control neurogenesis in this sheet of cells, directing some to become neurons while others remain non-neuronal? The answer is virtually unknown for vertebrates, but many of the cellular interactions and genes controlling cell fate decisions during neurogenesis have been well characterized in Drosophila (Campos-Ortega, 1993, J. Neurobiol. 24:1305–1327). Although the gross anatomical context of neurogenesis appears very different in insects and vertebrates, the possibility remains that, at a cellular level, similar events are occurring via conserved molecular mechanisms. Embryological, genetic and molecular evidence indicates that the early steps of ectodermal differentiation in Drosophila depend on cell interactions (Doe and Goodman, 1985, Dev. Biol. 111:206–219; Technau and Campos-Ortega, 1986, Dev. Biol. 195:445–454; Vässin et al., 1985, J. Neurogenet. 2:291–308; de la Concha et al., 1988, Genetics 118:499–508; Xu et al., 1990, Genes Dev. 4:464–475; Artavanis-Tsakonas, 1988, Trends Genet. 4:95–100). Mutational analyses reveal a small group of zygotically-acting genes, the so called neurogenic loci, which affect the choice of ectodermal cells between epidermal and neural pathways (Poulson, 1937, Proc. Natl. Acad. Sci. 23:133–137; Lehmann et al., 1983, Wilhelm Roux's Arch. Dev. Biol. 192:62–74; Jürgens et al., 1984, Wilhelm Roux's Arch. Dev. Biol. 193:283–295; Wieschaus et al., 1984, Wilhelm Roux's Arch. Dev. Biol. 193:296–307; Nüsslein-Volhard et al., 1984, Wilhelm Roux's Arch. Dev. Biol. 193:267–282). Null mutations in any one of the zygotic neurogenic loci—Notch (N), Delta (Dl), mastermind (mam), Enhancer of Split (E(spl)), neuralized (neu), and big brain (bib)—result in hypertrophy of the nervous system at the expense of ventral and lateral epidermal structures. This effect is due to the misrouting of epidermal precursor cells into a neuronal pathway, and implies that neurogenic gene function is necessary to divert cells within the neurogenic region from a neuronal fate to an epithelial fate.

Neural precursors arise in the Drosophila embryo from a neurogenic epithelium during successive waves of neurogenesis (Campos-Ortega & Hartenstein, 1985, The embryonic development of Drosophila melanogaster (Springer-Verlag, Berlin; New York); Doe, 1992, Development 116:855–863). The pattern of production of these cells is largely determined by the activity of the proneural and neurogenic genes. Proneural genes predispose clusters of cells to a neural fate (reviewed in Skeath & Carroll, 1994, Faseb J. 8:714–21), but only a subset of cells in a cluster become neural precursors. This restriction is due to the action of the neurogenic genes, which mediate lateral inhibition—a type of inhibitory cell signaling by which a cell committed to a neural fate forces its neighbors either to remain uncommitted or to enter a non-neural pathway (Artavanis-Tsakonas & Simpson, 1991, Trends Genet. 7:403–408; Doe & Goodman, 1985, Dev. Biol. 111:206–219). Mutations leading to a failure of lateral inhibition cause an overproduction of neurons—the "neurogenic" phenotype (Lehmann et al., 1981, Roux's Arch. Dev. Biol. 190:226–229; Lehmann et al., Roux's Arch. Dev. Biol. 192:62–74). In Drosophila, the inhibitory signal is delivered by a transmembrane protein encoded by the Delta neurogenic gene, which is displayed by the nascent neural cells (Heitzler & Simpson, 1991, Cell 64:1083–1092). Neighboring cells express a transmembrane receptor protein, encoded by the neurogenic gene Notch (Fortini & Artavanis-Tsakonas, 1993, Cell 75:1245–1247). Delta has been identified as a genetic unit capable of interacting with the Notch locus (Xu et al., 1990, Genes Dev. 4:464–475).

Mutational analyses also reveal that the action of the neurogenic genes is pleiotropic and is not limited solely to embryogenesis. For example, ommatidial, bristle and wing formation, which are known also to depend upon cell interactions, are affected by neurogenic mutations (Morgan et al., 1925, Bibliogr. Genet. 2:1–226; Welshons, 1956, Dros. Inf. Serv. 30:157–158; Preiss et al., 1988, EMBO J. 7:3917–3927; Shellenbarger and Mohler, 1978, Dev. Biol. 62:432–446; Technau and Campos-Ortega, 1986, Wilhelm Roux's Dev. Biol. 195:445–454; Tomlison and Ready, 1987, Dev. Biol. 120:366–376; Cagan and Ready, 1989, Genes Dev. 3:1099–1112). Neurogenic genes are also required for normal development of the muscles, gut, excretory and reproductive systems of the fly (Muskavitch, 1994, Dev. Biol. 166:415–430).

Both Notch and Delta are transmembrane proteins that span the membrane a single time (Wharton et al., 1985, Cell 43:567–581; Kidd and Young, 1986, Mol. Cell. Biol. 6:3094–3108; Vässin, et al., 1987, EMBO J. 6:3431–3440; Kopczynski, et al., 1988, Genes Dev. 2:1723–1735) and include multiple tandem EGF-like repeats in their extracellular domains (Muskavitch, 1994, Dev. Biol. 166:415–430). The Notch gene encodes a ~300 kd protein (we use "Notch" to denote this protein) with a large N-terminal extracellular domain that includes 36 epidermal growth factor (EGF)-like tandem repeats followed by three other cysteine-rich repeats, designated Notch/lin-12 repeats (Wharton, et al., 1985, Cell 43:567–581; Kidd and Young, 1986, Mol. Cell. Biol. 6:3094–3108; Yochem, et al., 1988, Nature 335:547–550). Molecular studies have lead to the suggestion that Notch and Delta constitute biochemically interacting elements of a cell communication mechanism involved in early developmental decisions (Fehon et al., 1990, Cell 61:523–534). Homologs are found in *Caenorhabditis elegans*, where the Notch-related gene lin-12 and the Delta-related gene lag-2 are also responsible for lateral inhibition (Sternberg, 1993, Current Biol. 3:763–765; Henderson et al., 1994, Development 120:2913–2924; Greenwald, 1994, Curr. Opin. Genet. Dev. 4:556–562). In vertebrates, several Notch homologs have also been identified (Kopan & Weintraub, 1993, J. Cell Biol. 121:631–641; Lardelli et al., 1994, Mech. Dev. 46:123–136; Lardelli & Lendahl, 1993, Exp. Cell Res. 204:364–372; Weinmaster et al., 1991, Development 113:199–205; Weimnaster et al., 1992, Development 116:931–941; Coffman et al., 1990, Science 249:1438–1441; Bierkamp & Campos-Ortega, 1993, Mech. Dev. 43:87–100), and they are expressed in many tissues and at many stages of development. Loss of Notch-1 leads to somite defects and embryonic death in mice (Swiatek et al., 1994, Genes Dev. 8:707–719; Conlon et al., Rossant, J. Development (J. Dev. 121:1533–1545), while constitutively active mutant forms of Notch-1 appear to inhibit cell differentiation in Xenopus and in cultured mammalian cells (Coffman et al., 1993, Cell 73:659–671; Kopan et al., 1994, Development 120:2385–2396; Nye et al., 1994, Development 120:2421–2430).

The EGF-like motif has been found in a variety of proteins, including those involved in the blood clotting cascade (Furie and Furie, 1988, Cell 53: 505–518). In particular, this motif has been found in extracellular proteins such as the blood clotting factors IX and X (Rees et al., 1988, EMBO J. 7:2053–2061; Furie and Furie, 1988, Cell 53: 505–518), in other Drosophila genes (Knust et al., 1987 EMBO J. 761–766; Rothberg et al., 1988, Cell 55:1047–1059), and in some cell-surface receptor proteins, such as thrombomodulin (Suzuki et al., 1987, EMBO J. 6:1891–1897) and LDL receptor (Sudhof et al., 1985, Science 228:815–822). A protein binding site has been mapped to the EGF repeat domain in thrombomodulin and urokinase (Kurosawa et al., 1988, J. Biol. Chem 263:5993–5996; Appella et al., 1987, J. Biol. Chem. 262:4437–4440).

Citation of references hereinabove shall not be construed as an admission that such references are prior art to the present invention.

SUMMARY OF THE INVENTION

The present invention relates to nucleotide sequences of vertebrate Delta genes (chick and mouse Delta, and related genes of other species), and amino acid sequences of their encoded proteins, as well as derivatives (e.g., fragments) and analogs thereof. Nucleic acids hybridizable to or complementary to the foregoing nucleotide sequences are also provided. In a specific embodiment, the Delta protein is a mammalian protein, preferably a human protein.

The invention relates to vertebrate Delta derivatives and analogs of the invention which are functionally active, i.e., they are capable of displaying one or more known functional activities associated with a full-length (wild-type) Delta protein. Such functional activities include but are not limited to antigenicity [ability to bind (or compete with Delta for binding) to an anti-Delta antibody], immunogenicity (ability to generate antibody which binds to Delta), ability to bind (or compete with Delta for binding) to Notch or other toporythmic proteins or fragments thereof ("adhesiveness"), ability to bind (or compete with Delta for binding) to a receptor for Delta. "Toporythmic proteins" as used herein, refers to the protein products of Notch, Delta, Serrate, Enhancer of split, and Deltex, as well as other members of this interacting set of genes which may be identified, e.g., by virtue of the ability of their gene sequences to hybridize, or their homology to Delta, Serrate, or Notch, or the ability of their genes to display phenotypic interactions or the ability of their protein products to interact biochemically.

The invention further relates to fragments (and derivatives and analogs thereof) of a vertebrate Delta that comprise one or more domains of the Delta protein, including but not limited to the intracellular domain, extracellular domain, transmembrane domain, DSL domain, domain amino-terminal to the DSL domain, or one or more EGF-like (homologous) repeats of a Delta protein, or any combination of the foregoing.

Antibodies to a vertebrate Delta, its derivatives and analogs, are additionally provided.

Methods of production of the vertebrate Delta proteins, derivatives and analogs, e.g., by recombinant means, are also provided.

The present invention also relates to therapeutic and diagnostic methods and compositions based on Delta proteins and nucleic acids. The invention provides for treatment of disorders of cell fate or differentiation by administration of a therapeutic compound of the invention. Such therapeutic compounds (termed herein "Therapeutics") include: Delta proteins and analogs and derivatives (including fragments) thereof; antibodies thereto; nucleic acids encoding the Delta proteins, analogs, or derivatives; and Delta antisense nucleic acids. In a preferred embodiment, a Therapeutic of the invention is administered to treat a cancerous condition, or to prevent progression from a pre-neoplastic or non-malignant state into a neoplastic or a malignant state. In other specific embodiments, a Therapeutic of the invention is administered to treat a nervous system disorder or to promote tissue regeneration and repair.

In one embodiment, Therapeutics which antagonize, or inhibit, Notch and/or Delta function (hereinafter "Antagonist Therapeutics") are administered for therapeutic effect. In another embodiment, Therapeutics which promote Notch and/or Delta function (hereinafter "Agonist Therapeutics") are administered for therapeutic effect.

Disorders of cell fate, in particular hyperproliferative (e.g., cancer) or hypoproliferative disorders, involving aberrant or undesirable levels of expression or activity or localization of Notch and/or Delta protein can be diagnosed by detecting such levels, as described more fully infra.

In a preferred aspect, a Therapeutic of the invention is a protein consisting of at least a fragment (termed herein "adhesive fragment") of Delta which mediates binding to a Notch protein or a fragment thereof.

DEFINITIONS

As used herein, underscoring or italicizing the name of a gene shall indicate the gene, in contrast to its encoded protein product which is indicated by the name of the gene in the absence of any underscoring. For example, "Delta" shall mean the Delta gene, whereas "Delta" shall indicate the protein product of the Delta gene.

DESCRIPTION OF THE FIGURES

FIGS. 1A1–1A3–1B1–1B2. FIGS. 1A1–1A3. The DNA sequence of chick Delta (C-Delta-1) (SEQ ID NO:1). FIGS. 1B1–1B2. The DNA sequence of an alternatively spliced chick Delta (C-Delta-1) (SEQ ID NO:3).

FIG. 2. The predicted amino acid sequence of chick Delta (C-Delta-1) (SEQ ID NO:2).

FIGS. 3A–3B. Predicted amino acid sequence of C-Delta-1 (SEQ ID NO:2), aligned with that of X-Delta-1 (Xenopus Delta; SEQ ID NO:5) and Drosophila Delta (SEQ ID NO:6) and, indicating the conserved domain structures: EGF repeats, DSL domain, and transmembrane domain (TM). Conserved amino acids are boxed, and denote aligned and non-aligned N-terminal cysteine residues, respectively. Although the intracellular domains of C-Delta-1 and X-Delta-1 closely resemble each other, they show no significant homology to the corresponding part of Drosophila Delta.

FIG. 4. Alignment of DSL domains from C-Delta-1 (SEQ ID NO:2), Drosophila Delta (SEQ ID NO:6) (Vässin et al., 1987, EMBO J. 6:3431–3440; Kopczynski et al., 1988, Genes Dev. 2:1723–1735), Drosophila Serrate (SEQ ID NO:7) (Fleming et al., 1990, Genes Dev. 4:2188–2201; Thomas et al., 1991, Development 111:749–761), C-Serrate-1 (SEQ ID NO:8) (Myat, Henrique, Ish-Horowicz and Lewis, in preparation), Apx-1 (SEQ ID NO:9) (Mello et al., 1994, Cell 77:95–106) and Lag-2 (SEQ ID NO:10) (Henderson et al., 1994, Development 120:2913–2924; Tax et al., 1994, Nature 368:150–154), showing the conserved Cysteine spacings, the amino acids that are conserved between presumed ligands for Notch-like proteins in Drosophila and vertebrates, and those that are further conserved in C. elegans ligands (boxes).

FIG. 5a, At stage 7, C-Notch-1 is expressed throughout most of the neural plate and part of the underlying presomitic mesoderm. FIG. 5b, C-Delta-1 at stage 7 is already detectable in the neural plate, in the future posterior hindbrain, just anterior to the first somite (white box). The posterior end of this neural domain is roughly level with the anterior margin of a domain of very strong expression in the underlying presomitic mesoderm (psm). Earlier expression in the neural plate may occur and be masked by expression in the underlying mesoderm (unpublished results). FIG. 5c, Higher magnification view of the area boxed in 5b, showing scattered cells in the neural plate expressing C-Delta-1. FIG. 5d, At stage 8, C-Delta-1 expression in the neural plate extends posteriorly as the neural plate develops. The domain of labelled neural plate cells visible in this photograph (bracketed) continues posteriorly over the presomitic mesoderm. FIG. 5e, Parasagittal section of a stage 8 embryo showing that C-Delta-1 is expressed in scattered cells of the neural plate (dorsal layer of tissue; bracketed), and broadly in the presomitic mesoderm (ventral layer). The plane of section is slightly oblique, missing the posterior part of the neural plate domain (cf. 5d).

FIG. 6a, Diagram showing how phase in the cell cycle is related to apico-basal position of the nucleus for cells in the neuroepithelium; S-phase nuclei lie basally (Fujita, 1963, J. Comp. Neurol. 120:37–42; Biffo et al., 1992, Histochem. Cytochem. 40:535–540). Nuclei are indicated by shading. FIG. 6b, Section through the neural tube of a stage 9 embryo labelled for 2 h with BrdU showing C-Delta-1 expressing cells (dark on blue background) and BrdU-labelled nuclei (pink). Labelled nuclei are predominantly basal, where DNA synthesis occurs, yet basal C-Delta-1-expressing cells are unlabelled. FIG. 6c, Section through a stage 9 embryo incubated for 4 h: many labelled nuclei have exited S-phase and have moved towards the lumen, but C-Delta-1-expressing cells are still basal and not labelled with BrdU.

FIGS. 7A–7B. The DNA sequence of mouse Delta (M-Delta-i) (SEQ ID NO:11).

FIG. 8. The predicted amino acid sequence of the mouse Delta (M-Delta-1) (SEQ ID NO:12).

FIGS. 9A–9B. An alignment of the predicted amino acid sequence of mouse M-Delta-1 (SEQ ID NO:12) with the chick C-Delta-1 (SEQ ID NO:2) which shows their extensive amino acid sequence identity. Identical amino acids are boxed. The consensus sequence between the two genes is at the bottom (SEQ ID NO:13).

FIGS. 10A–10B. The DNA sequence of a PCR amplified fragment of human Delta (H-Delta-1)(SEQ ID NO:14) and the predicted amino acid sequences using the three available open reading frames, 2nd line (SEQ ID NOS:15–17), 3rd line (SEQ ID NO:18), 4th line (SEQ ID NO:19–22).

FIG. 11. An alignment of human H-Delta-1 (top line) and chick C-Delta-1 (bottom line). The predicted amino acid sequence of human Delta (SEQ ID NO:23) is shown in the top line. The sequence of human Delta was determined by "eye", in which the sequence of the appropriate reading frame was determined by maximizing homology with C-Delta-1. No single reading frame shown in FIGS. 10A–10B gave the correct sequence due to errors in the DNA sequence of FIGS. 10A–10B that caused reading frameshifts.

FIGS. 12A1–12A3–12B1–12B6. FIGS. 12A1–12A3 present the contig DNA sequence of human Delta (H-Delta-1) (SEQ ID NO:26) from clone HD118. FIGS. 12B1–12B6 present the nucleotide sequence shown in FIGS. 12A1–12A3 (top line, SEQ ID NO:26) and the deduced amino acid sequences using the three possible open reading frames, second line (SEQ ID NOS:27–42), third line (SEQ ID NOS:43–47), fourth line (SEQ ID NOS:48–64). The amino acid sequence with the greatest homology to the mouse Delta-1 amino acid sequence is boxed. This boxed amino acid sequence is the predicted amino acid sequence of human Delta; where the reading frame shifts indicates where a sequencing error is present in the sequence. No single reading frame shown in FIGS. 12A1–12A3 gave an uninterrupted amino acid sequence due to errors in the DNA sequence that caused shifts in the reading frame. X indicates an undetermined amino acid; N indicates an undetermined nucleotide.

FIGS. 13A–13G. An alignment of mouse M-Delta-1 DNA sequence (top line, SEQ ID NO:4) and human H-Delta-1 DNA sequence (second line, SEQ ID NO:26) and their consensus sequence (third line, SEQ ID NO:24).

FIGS. 14A–14B. The composite human Delta (H-Delta-1) amino acid sequence (SEQ ID NOS:65–80, respectively) is presented, representing the boxed amino sequence from FIGS. 12B1–12B6. ">" indicates that the sequence continues on the line below. "*" indicates a break in the sequence.

DETAILED DESCRIPTION OF THE INVENTION

Figure 3A:
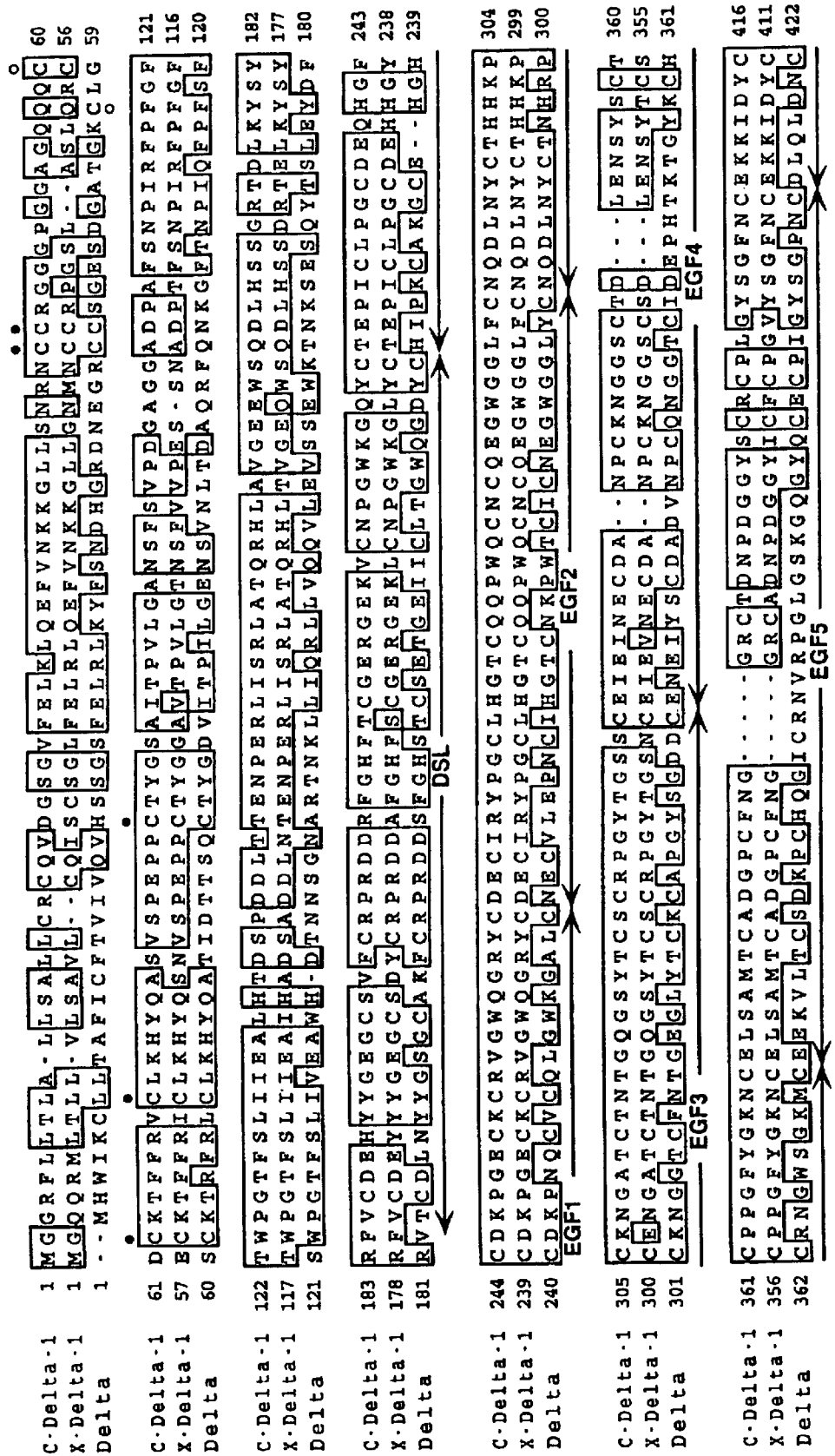

The present invention relates to nucleotide sequences of vertebrate Delta genes, and amino acid sequences of their encoded proteins. The invention further relates to fragments and other derivatives, and analogs, of vertebrate Delta proteins. Nucleic acids encoding such fragments or derivatives are also within the scope of the invention. The invention provides Delta genes and their encoded proteins of many different vertebrate species. The Delta genes of the invention include chick, mouse, and human Delta and related genes (homologs) in other vertebrate species. In specific embodiments, the Delta genes and proteins are from vertebrates, or more particularly, mammals. In a preferred embodiment of the invention, the Delta protein is a human protein. Production of the foregoing proteins and derivatives, e.g., by recombinant methods, is provided.

The invention relates to Delta derivatives and analogs of the invention which are functionally active, i.e., they are capable of displaying one or more known functional activities associated with a full-length (wild-type) Delta protein. Such functional activities include but are not limited to antigenicity [ability to bind (or compete with Delta for binding) to an anti-Delta antibody], immunogenicity (ability to generate antibody which binds to Delta), ability to bind (or compete with Delta for binding) to Notch or other toporythmic proteins or fragments thereof ("adhesiveness"), ability to bind (or compete with Delta for binding) to a receptor for Delta, ability to affect cell fate differentiation, and therapeutic activity. "Toporythmic proteins" as used herein, refers to the protein products of Notch, Delta, Serrate, Enhancer of split, and Deltex, as well as other members of this interacting gene family which may be identified, e.g., by virtue of the ability of their gene sequences to hybridize, or their homology to Delta, Serrate, or Notch, or the ability of their genes to display phenotypic interactions.

The invention further relates to fragments (and derivatives and analogs thereof) of Delta which comprise one or more domains of the Delta protein, including but not limited to the intracellular domain, extracellular domain, DSL domain, region amino-terminal to the DSL domain, transmembrane domain, membrane-associated region, or one or more EGF-like (homologous) repeats of a Delta protein, or any combination of the foregoing.

Antibodies to vertebrate Delta, its derivatives and analogs, are additionally provided.

As demonstrated infra, Delta plays a critical role in development and other physiological processes, in particular, as a ligand to Notch, which is involved in cell fate (differentiation) determination. In particular, Delta is believed to play a major role in determining cell fates in the central nervous system. The nucleic acid and amino acid sequences and antibodies thereto of the invention can be used for the detection and quantitation of Delta mRNA and protein of human and other species, to study expression thereof, to produce Delta and fragments and other derivatives and analogs thereof, in the study and manipulation of differentiation and other physiological processes. The present invention also relates to therapeutic and diagnostic methods and compositions based on Delta proteins and nucleic acids. The invention provides for treatment of disorders of cell fate or differentiation by administration of a therapeutic compound of the invention. Such therapeutic compounds (termed herein "Therapeutics") include: Delta proteins and analogs and derivatives (including fragments) thereof; antibodies thereto; nucleic acids encoding the Delta proteins, analogs, or derivatives; and Delta antisense nucleic acids. In a preferred embodiment, a Therapeutic of the invention is administered to treat a cancerous condition, or to prevent progression from a pre-neoplastic or non-malignant state into a neoplastic or a malignant state. In other specific embodiments, a Therapeutic of the invention is administered to treat a nervous system disorder or to promote tissue regeneration and repair.

In one embodiment, Therapeutics which antagonize, or inhibit, Notch and/or Delta function (hereinafter "Antagonist Therapeutics") are administered for therapeutic effect. In another embodiment, Therapeutics which promote Notch and/or Delta function (hereinafter "Agonist Therapeutics") are administered for therapeutic effect.

Disorders of cell fate, in particular hyperproliferative (e.g., cancer) or hypoproliferative disorders, involving aberrant or undesirable levels of expression or activity or localization of Notch and/or Delta protein can be diagnosed by detecting such levels, as described more fully infra.

In a preferred aspect, a Therapeutic of the invention is a protein consisting of at least a fragment (termed herein "adhesive fragment") of Delta which mediates binding to a Notch protein or a fragment thereof.

The invention is illustrated by way of examples infra which disclose, inter alia, the cloning of a chick Delta homolog (Section 6), the cloning of a mouse Delta homolog (Section 7), and the cloning of a human Delta homolog (Section 8).

For clarity of disclosure, and not by way of limitation, the detailed description of the invention is divided into the subsections which follow.

5.1 Isolation of the Delta Genes

The invention relates to the nucleotide sequences of vertebrate Delta nucleic acids. In specific embodiments, human Delta nucleic acids comprise the cDNA sequences shown in FIGS. 10A–10B (SEQ ID NO:14) or in FIGS. 12A1–12A3 (SEQ ID NO:26), or the coding regions thereof, or nucleic acids encoding a vertebrate Delta protein (e.g., having the sequence of SEQ ID NO:1, 3, 11, 14 or 26). The invention provides nucleic acids consisting of at least 8 nucleotides (i.e., a hybridizable portion) of a vertebrate Delta sequence; in other embodiments, the nucleic acids consist of at least 25 (continuous) nucleotides, 50 nucleotides, 100 nucleotides, 150 nucleotides, or 200 nucleotides of a Delta sequence, or a full-length Delta coding sequence. The invention also relates to nucleic acids hybridizable to or complementary to the foregoing sequences or their complements. In specific aspects, nucleic acids are provided which comprise a sequence complementary to at least 10, 25, 50, 100, or 200 nucleotides or the entire coding region of a vertebrate Delta gene. In a specific embodiment, a nucleic acid which is hybridizable to a vertebrate (e.g., mammalian) Delta nucleic acid (e.g., having sequence SEQ ID NO:14 or SEQ ID NO:26, or an at least 10, 25, 50, 100, or 200 nucleotide portion thereof), or to a nucleic acid encoding a Delta derivative, under conditions of low stringency is provided. By way of example and not limitation, procedures using such conditions of low stringency are as follows (see also Shilo and Weinberg, 1981, Proc. Natl. Acad. Sci. USA 78:6789–6792): Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 $\mu$mg/ml denatured salmon sperm DNA. Hybridizations are carried out in the same solution with the following modifications: 0.02% PVP, 0.02% Ficoll, 0.2% BSA, 100 $\mu$mg/ml salmon sperm DNA, 10% (wt/vol) dextran sulfate, and 5–20×10$^6$ cpm $^{32}$P-labeled probe is used. Filters are incubated in hybridization mixture for 18–20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65–68° C. and reexposed to film. Other conditions of low stringency which may be used are well known in the art (e.g., as employed for cross-species hybridizations).

In another specific embodiment, a nucleic acid which is hybridizable to a vertebrate (e.g., mammalian) Delta nucleic acid under conditions of high stringency is provided. By way of example and not limitation, procedures using such conditions of high stringency are as follows: Prehybridization of filters containing DNA is carried out for 8 h to overnight at 65° C. in buffer composed of 6× SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA and 5–20×10[6] cpm of $^{32}$P-labeled probe. Washing of filters is done at 37° C. for 1 h in a solution containing 2× SSC, 0.01% PVP, 0.01% Ficoll, and 0.01% BSA. This is followed by a wash in 0.1× SSC at 50° C. for 45 min before autoradiography. Other conditions of high stringency which may be used are well known in the art.

Nucleic acids encoding fragments and derivatives of vertebrate Delta proteins (see Section 5.6), and Delta antisense nucleic acids (see Section 5.11) are additionally provided. As is readily apparent, as used herein, a "nucleic acid encoding a fragment or portion of a Delta protein" shall be construed as referring to a nucleic acid encoding only the recited fragment or portion of the Delta protein and not the other contiguous portions of the Delta protein as a continuous sequence.

Figure 3B:
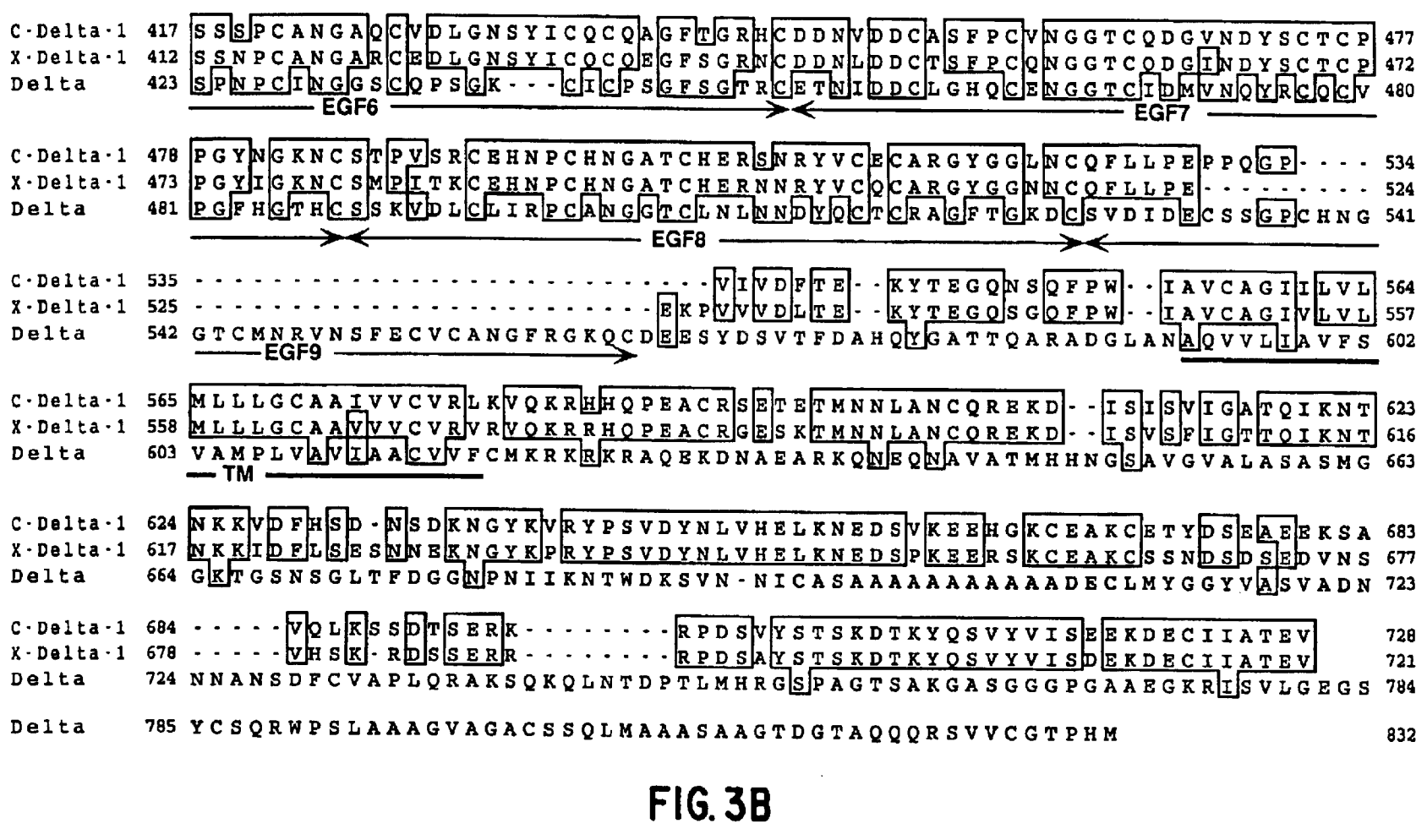

Fragments of vertebrate Delta nucleic acids comprising regions of homology to other toporythmic proteins are also provided. The DSL regions (regions of homology with Drosophila Serrate and Delta) of Delta proteins of other species are also provided. Nucleic acids encoding conserved regions between Delta and Serrate, such as those shown in FIGS. 3A–3B and 8 are also provided.

Specific embodiments for the cloning of a vertebrate Delta gene, presented as a particular example but not by way of limitation, follows:

For expression cloning (a technique commonly known in the art), an expression library is constructed by methods known in the art. For example, mRNA (e.g., human) is isolated, cDNA is made and ligated into an expression vector (e.g., a bacteriophage derivative) such that it is capable of being expressed by the host cell into which it is then introduced. Various screening assays can then be used to select for the expressed Delta product. In one embodiment, anti-Delta antibodies can be used for selection.

In another preferred aspect, PCR is used to amplify the desired sequence in a genomic or cDNA library, prior to selection. Oligonucleotide primers representing known Delta sequences (preferably vertebrate sequences) can be used as primers in PCR. In a preferred aspect, the oligonucleotide primers represent at least part of the Delta conserved segments of strong homology between Serrate and Delta. The synthetic oligonucleotides may be utilized as primers to amplify by PCR sequences from a source (RNA or DNA), preferably a cDNA library, of potential interest. PCR can be carried out, e.g., by use of a Perkin-Elmer Cetus thermal cycler and Taq polymerase (Gene Amp™). The DNA being amplified can include mRNA or cDNA or genomic DNA from any eukaryotic species. One can choose to synthesize several different degenerate primers, for use in the PCR reactions. It is also possible to vary the stringency of hybridization conditions used in priming the PCR reactions, to allow for greater or lesser degrees of nucleotide sequence similarity between the known Delta nucleotide sequence and the nucleic acid homolog being isolated. For cross species hybridization, low stringency conditions are preferred. For same species hybridization, moderately stringent conditions are preferred. After successful amplification of a segment of a Delta homolog, that segment may be molecularly cloned and sequenced, and utilized as a probe to isolate a complete cDNA or genomic clone. This, in turn, will permit the determination of the gene's complete nucleotide sequence, the analysis of its expression, and the production of its protein product for functional analysis, as described infra. In this fashion, additional genes encoding Delta proteins may be identified. Such a procedure is presented by way of example in various examples sections infra.

The above-methods are not meant to limit the following general description of methods by which clones of Delta may be obtained.

Any vertebrate cell potentially can serve as the nucleic acid source for the molecular cloning of the Delta gene. The nucleic acid sequences encoding Delta can be isolated from mammalian, human, porcine, bovine, feline, avian, equine, canine, as well as additional primate sources, etc. For example, we have amplified fragments of the Delta gene in mouse, chicken, and human, by PCR using cDNA libraries with Delta primers. The DNA may be obtained by standard procedures known in the art from cloned DNA (e.g., a DNA "library"), by chemical synthesis, by cDNA cloning, or by the cloning of genomic DNA, or fragments thereof, purified from the desired cell. (See, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II.) Clones derived from genomic DNA may contain regulatory and intron DNA regions in addition to coding regions; clones derived from cDNA will contain only exon sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired gene may be accomplished in a number of ways. For example, if an amount of a portion of a Delta (of any species) gene or its specific RNA, or a fragment thereof, e.g., an extracellular domain (see Section 5.6), is available and can be purified and labeled, the generated DNA fragments may be screened by nucleic acid hybridization to the labeled probe (Benton, W. and Davis, R., 1977, Science 196:180; Grunstein, M. And Hogness, D., 1975, Proc. Natl. Acad. Sci. U.S.A. 72:3961). Those DNA fragments with substantial homology to the probe will hybridize. It is also possible to identify the appropriate fragment by restriction enzyme digestion(s) and comparison of fragment sizes with those expected according to a known restriction map if such is available. Further selection can be carried out on the basis of the properties of the gene. Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isolectric focusing behavior, proteolytic digestion maps, binding activity, in vitro aggregation activity ("adhesiveness") or antigenic properties as known for Delta.

If an antibody to Delta is available, the Delta protein may be identified by binding of labeled antibody to the putatively Delta synthesizing clones, in an ELISA (enzyme-linked immunosorbent assay)-type procedure.

The Delta gene can also be identified by mRNA selection by nucleic acid hybridization followed by in vitro translation. In this procedure, fragments are used to isolate complementary mRNAs by hybridization. Such DNA fragments may represent available, purified Delta DNA of another species (e.g., Drosophila). Immunoprecipitation analysis or functional assays (e.g., aggregation ability in vitro; binding to receptor; see infra) of the in vitro translation products of the isolated products of the isolated mRNAs identifies the mRNA and, therefore, the complementary DNA fragments that contain the desired sequences. In addition, specific mRNAs may be selected by adsorption of polysomes isolated from cells to immobilized antibodies specifically directed against Delta protein. A radiolabelled Delta cDNA can be synthesized using the selected mRNA (from the adsorbed polysomes) as a template. The radiolabelled mRNA or cDNA may then be used as a probe to identify the Delta DNA fragments from among other genomic DNA fragments.

Alternatives to isolating the Delta genomic DNA include, but are not limited to, chemically synthesizing the gene sequence itself from a known sequence or making cDNA to the mRNA which encodes the Delta protein. For example, RNA for cDNA cloning of the Delta gene can be isolated from cells which express Delta. Other methods are possible and within the scope of the invention.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as PBR322 or pUC plasmid derivatives. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and Delta gene may be modified by homopolymeric tailing. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment for the desired gene, for example, by size fractionation, can be done before insertion into the cloning vector.

In specific embodiments, transformation of host cells with recombinant DNA molecules that incorporate the isolated Delta gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

The Delta sequences provided by the instant invention include those nucleotide sequences encoding substantially the same amino acid sequences as found in native vertebrate Delta proteins, and those encoded amino acid sequences with functionally equivalent amino acids, all as described in Section 5.6 infra for Delta derivatives.

5.2. Expression of the Delta Genes

The nucleotide sequence coding for a vertebrate Delta protein or a functionally active fragment or other derivative thereof (see Section 5.6), can be inserted into an appropriate expression vector, i.e., a vector which contains the necessary elements for the transcription and translation of the inserted protein-coding sequence. The necessary transcriptional and translational signals can also be supplied by the native Delta gene and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used. In a specific embodiment, the adhesive portion of the Delta gene is expressed. In other specific embodiments, the human Delta gene is expressed, or a sequence encoding a functionally active portion of human Delta. In yet another embodiment, a fragment of Delta comprising the extracellular domain, or other derivative, or analog of Delta is expressed.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination). Expression of nucleic acid sequence encoding a Delta protein or peptide fragment may be regulated by a second nucleic acid sequence so that the Delta protein or peptide is expressed in a host transformed with the recombinant DNA molecule. For example, expression of a Delta protein may be controlled by any promoter/enhancer element known in the art. Promoters which may be used to control Delta gene expression include, but are not limited to, the SV40 early promoter region (Bernoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the P-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; plant expression vectors comprising the nopaline synthetase promoter region (Herrera-Estrella et al., Nature 303:209–213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al., 1984, Nature 310:115–120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58; alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94; myelin basic protein gene control region which is active in oligodendrocyte cells in the brain (Readhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

Expression vectors containing Delta gene inserts can be identified by three general approaches: (a) nucleic acid hybridization, (b) presence or absence of "marker" gene functions, and (c) expression of inserted sequences. In the first approach, the presence of a foreign gene inserted in an expression vector can be detected by nucleic acid hybridization using probes comprising sequences that are homologous to an inserted toporythmic gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if the Delta gene is inserted within the marker gene sequence of the vector, recombinants containing the Delta insert can be identified by the absence of the marker gene function. In the third approach, recombinant expression vectors can be identified by assaying the foreign gene product expressed by the recombinant. Such assays can be based, for example, on the physical or functional properties of the Delta gene product in vitro assay systems, e.g., aggregation (binding) with Notch, binding to a receptor, binding with antibody.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered Delta protein may be controlled. Furthermore, different host cells have characteristic and specific mechanisms for the translational and post-translational processing and modification (e.g., glycosylation, cleavage [e.g., of signal sequence]) of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of a heterologous mammalian Delta protein. Furthermore, different vector/host expression systems may effect processing reactions such as proteolytic cleavages to different extents.

In other specific embodiments, the Delta protein, fragment, analog, or derivative may be expressed as a fusion, or chimeric protein product (comprising the protein, fragment, analog, or derivative joined via a peptide bond to a heterologous protein sequence (of a different protein)). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer.

Both cDNA and genomic sequences can be cloned and expressed.

5.3. Identification and Purification of the Delta Gene Products

In particular aspects, the invention provides amino acid sequences of a vertebrate Delta, preferably a human Delta, and fragments and derivatives thereof which comprise an antigenic determinant (i.e., can be recognized by an antibody) or which are otherwise functionally active, as well as nucleic acid sequences encoding the foregoing. "Functionally active" material as used herein refers to that material displaying one or more known functional activities associated with a full-length (wild-type) Delta protein, e.g., binding to Notch or a portion thereof, binding to any other Delta ligand, antigenicity (binding to an anti-Delta antibody), etc.

In specific embodiments, the invention provides fragments of a Delta protein consisting of at least 6 amino acids, 10 amino acids, 25 amino acids, 50 amino acids, or of at least 75 amino acids. Molecules comprising such fragments are also provided. In other embodiments, the proteins comprise or consist essentially of an extracellular domain, DSL domain, epidermal growth factor-like repeat (ELR) domain, one or any combination of ELRs, transmembrane domain, or intracellular (cytoplasmic) domain, or a portion which binds to Notch, or any combination of the foregoing, of a vertebrate Delta protein. Fragments, or proteins comprising fragments, lacking some or all of the foregoing regions of a Delta protein are also provided. Nucleic acids encoding the foregoing are provided.

Once a recombinant which expresses the Delta gene sequence is identified, the gene product can be analyzed. This is achieved by assays based on the physical or functional properties of the product, including radioactive labelling of the product followed by analysis by gel electrophoresis, immunoassay, etc.

Once the Delta protein is identified, it may be isolated and purified by standard methods including chromatography (e.g., ion exchange, affinity, and sizing column chromatography), centrifugation, differential solubility, or by any other standard technique for the purification of proteins. The functional properties may be evaluated using any suitable assay (see Section 5.7).

Alternatively, once a Delta protein produced by a recombinant is identified, the amino acid sequence of the protein can be deduced from the nucleotide sequence of the chimeric gene contained in the recombinant. As a result, the protein can be synthesized by standard chemical methods known in the art (e.g., see Hunkapiller, M., et al., 1984, Nature 310:105–111).

In a specific embodiment of the present invention, such Delta proteins, whether produced by recombinant DNA techniques or by chemical synthetic methods, include but are not limited to those containing, as a primary amino acid sequence, all or part of the amino acid sequences substantially as depicted in FIGS. 2, 8, 11 or 14A–14B (SEQ ID NOS:2, 12, 23 and 65–80), as well as fragments and other derivatives, and analogs thereof.

5.4. Structure of the Delta Genes and Proteins

The structure of the vertebrate Delta genes and proteins can be analyzed by various methods known in the art.

5.4.1. Genetic Analysis

The cloned DNA or cDNA corresponding to the Delta gene can be analyzed by methods including but not limited to Southern hybridization (Southern, E. M., 1975, J. Mol. Biol. 98:503–517), Northern hybridization (see e.g., Freeman et al., 1983, Proc. Natl. Acad. Sci. U.S.A. 80:4094–4098), restriction endonuclease mapping (Maniatis, T., 1982, Molecular Cloning, A Laboratory, Cold Spring Harbor, N.Y.), and DNA sequence analysis. Polymerase chain reaction (PCR; U.S. Pat. Nos. 4,683,202, 4,683,195 and 4,889,818; Gyllenstein et al., 1988, Proc. Natl. Acad. Sci. U.S.A. 85:7652–7656; Ochman et al., 1988, Genetics 120:621–623; Loh et al., 1989, Science 243:217–220) followed by Southern hybridization with a Delta-specific probe can allow the detection of the Delta gene in DNA from various cell types. Methods of amplification other than PCR are commonly known and can also be employed. In one embodiment, Southern hybridization can be used to determine the genetic linkage of Delta. Northern hybridization analysis can be used to determine the expression of the Delta gene. Various cell types, at various states of development or activity can be tested for Delta expression. Examples of such techniques and their results are described in Section 6, infra. The stringency of the hybridization conditions for both Southern and Northern hybridization can be manipulated to ensure detection of nucleic acids with the desired degree of relatedness to the specific Delta probe used.

Restriction endonuclease mapping can be used to roughly determine the genetic structure of the Delta gene. Restriction maps derived by restriction endonuclease cleavage can be confirmed by DNA sequence analysis.

DNA sequence analysis can be performed by any techniques known in the art, including but not limited to the method of Maxam and Gilbert (1980, Meth. Enzymol. 65:499–560), the Sanger dideoxy method (Sanger, F., et al., 1977, Proc. Natl. Acad. Sci. U.S.A. 74:5463), the use of T7 DNA polymerase (Tabor and Richardson, U.S. Pat. No. 4,795,699), or use of an automated DNA sequenator (e.g., Applied Biosystems, Foster City, Calif.).

5.4.2. Protein Analysis

The amino acid sequence of the Delta protein can be derived by deduction from the DNA sequence, or alternatively, by direct sequencing of the protein, e.g., with an automated amino acid sequencer. The amino acid sequence of a representative Delta protein comprises the sequence substantially as depicted in FIG. 2, and detailed in Section 6, infra, with the representative mature protein that shown by amino acid numbers 1–728.

The Delta protein sequence can be further characterized by a hydrophilicity analysis (Hopp, T. and Woods, K., 1981, Proc. Natl. Acad. Sci. U.S.A. 78:3824). A hydrophilicity profile can be used to identify the hydrophobic and hydrophilic regions of the Delta protein and the corresponding regions of the gene sequence which encode such regions. Hydrophilic regions are more likely to be immunogenic.

Secondary, structural analysis (Chou, P. and Fasman, G., 1974, Biochemistry 13:222) can also be done, to identify regions of Delta that assume specific secondary structures.

Manipulation, translation, and secondary structure prediction, as well as open reading frame prediction and plotting, can also be accomplished using computer software programs available in the art.

Other methods of structural analysis can also be employed. These include but are not limited to X-ray crystallography (Engstom, A., 1974, Biochem. Exp. Biol. 11:7–13) and computer modeling (Fletterick, R. and Zoller, M. (eds.), 1986, Computer Graphics and Molecular Modeling, in Current Communications in Molecular Biology, Cold Spring Harbor Laboratory, Cold Spring Harbor, N.Y.).

5.5. Generation of Antibodies to Delta Proteins and Derivatives Thereof

According to the invention, a vertebrate Delta protein, its fragments or other derivatives, or analogs thereof, may be used as an immunogen to generate antibodies which recognize such an immunogen. Such antibodies include but are not limited to polyclonal, monoclonal, chimeric, single chain, Fab fragments, and an Fab expression library. In a specific embodiment, antibodies to human Delta are produced. In another embodiment, antibodies to the extracellular domain of Delta are produced. In another embodiment, antibodies to the intracellular domain of Delta are produced.

Various procedures known in the art may be used for the production of polyclonal antibodies to a Delta protein or derivative or analog. In a particular embodiment, rabbit polyclonal antibodies to an epitope of the Delta protein encoded by a sequence depicted in FIGS. 1A1–1A3, 1B1–1B2, 7A–7B or 11, or a subsequence thereof, can be obtained. For the production of antibody, various host animals can be immunized by injection with the native Delta protein, or a synthetic version, or derivative (e.g., fragment) thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum.

For preparation of monoclonal antibodies directed toward a Delta protein sequence or analog thereof, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026–2030) or by transforming human B cells with EBV virus in vitro (Cole et al., 1985, in *Monoclonal Antibodies and Cancer Therapy*, Alan R. Liss, pp. 77–96). In fact, according to the invention, techniques developed for the production of "chimeric antibodies" (Morrison et al., 1984, Proc. Natl. Acad. Sci. U.S.A. 81:6851–6855; Neuberger et al., 1984, Nature 312:604–608; Takeda et al., 1985, Nature 314:452–454) by splicing the genes from a mouse antibody molecule specific for Delta together with genes from a human antibody molecule of appropriate biological activity can be used; such antibodies are within the scope of this invention.

According to the invention, techniques described for the production of single chain antibodies (U.S. Pat. No. 4,946,778) can be adapted to produce Delta-specific single chain antibodies. An additional embodiment of the invention utilizes the techniques described for the construction of Fab expression libraries (Huse et al., 1989, Science 246:1275–1281) to allow rapid and easy identification of monoclonal Fab fragments with the desired specificity for Delta proteins, derivatives, or analogs.

Antibody fragments which contain the idiotype of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g. ELISA (enzyme-linked immunosorbent assay). For example, to select antibodies which recognize a specific domain of a vertebrate Delta protein, one may assay generated hybridomas for a product which binds to a Delta fragment containing such domain. For selection of an antibody immunospecific to human Delta, one can select on the basis of positive binding to human Delta and a lack of binding to Drosophila Delta.

The foregoing antibodies can be used in methods known in the art relating to the localization and activity of the protein sequences of the invention (e.g. see Section 5.7, infra), e.g., for imaging these proteins, measuring levels thereof in appropriate physiological samples, in diagnostic methods, etc.

Antibodies specific to a domain of a Delta protein are also provided. In a specific embodiment, antibodies which bind to a Notch-binding fragment of Delta are provided.

In another embodiment of the invention (see infra), anti-Delta antibodies and fragments thereof containing the binding domain are Therapeutics.

5.6. Delta Proteins, Derivatives and Analogs

The invention further relates to vertebrate (e.g., mammalian) Delta proteins, and derivatives (including but not limited to fragments) and analogs of vertebrate Delta proteins. Nucleic acids encoding Delta protein derivatives and protein analogs are also provided. In one embodiment, the Delta proteins are encoded by the Delta nucleic acids described in Section 5.1 supra. In particular aspects, the proteins, derivatives, or analogs are of mouse, chicken, rat, pig, cow, dog, monkey, or human Delta proteins. In a specific embodiment, a mature, full-length vertebrate Delta protein is provided. In one embodiment, a vertebrate Delta protein lacking only the signal sequence (approximately the first 17 amino-terminal amino acids) is provided.

The production and use of derivatives and analogs related to Delta are within the scope of the present invention. In a specific embodiment, the derivative or analog is functionally active, i.e., capable of exhibiting one or more functional activities associated with a full-length, wild-type Delta protein. As one example, such derivatives or analogs which have the desired immunogenicity or antigenicity can be used, for example, in immunoassays, for immunization, for inhibition of Delta activity, etc. Such molecules which retain, or alternatively inhibit, a desired Delta property, e.g., binding to Notch or other toporythmic proteins, binding to a cell-surface receptor, can be used as inducers, or inhibitors, respectively, of such property and its physiological correlates. A specific embodiment relates to a Delta fragment that can be bound by an anti-Delta antibody but cannot bind to a Notch protein or other toporythmic protein. Derivatives or analogs of Delta can be tested for the desired activity by procedures known in the art, including but not limited to the assays described in Section 5.7.

In particular, Delta derivatives can be made by altering Delta sequences by substitutions, additions or deletions that provide for functionally equivalent molecules. Due to the degeneracy of nucleotide coding sequences, other DNA sequences which encode substantially the same amino acid sequence as a Delta gene may be used in the practice of the present invention. These include but are not limited to nucleotide sequences comprising all or portions of Delta genes which are altered by the substitution of different codons that encode a functionally equivalent amino acid residue within the sequence, thus producing a silent change. Likewise, the Delta derivatives of the invention include, but are not limited to, those containing, as a primary amino acid sequence, all or part of the amino acid sequence of a Delta protein including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

In a specific embodiment of the invention, proteins consisting of or comprising a fragment of a vertebrate Delta protein consisting of at least 10 (continuous) amino acids of the Delta protein is provided. In other embodiments, the fragment consists of at least 20 or 50 amino acids of the Delta protein. In specific embodiments, such fragments are not larger than 35, 100 or 200 amino acids. Derivatives or analogs of Delta include but are not limited to those peptides which are substantially homologous to a vertebrate Delta protein or fragments thereof (e.g., at least 30%, 50%, 70%, or 90% identity over an amino acid sequence of identical size—e.g., comprising a domain) or whose encoding nucleic acid is capable of hybridizing to a coding Delta sequence.

The Delta derivatives and analogs of the invention can be produced by various methods known in the art. The manipulations which result in their production can occur at the gene or protein level. For example, the cloned Delta gene sequence can be modified by any of numerous strategies known in the art (Maniatis, T., 1990, Molecular Cloning, A Laboratory Manual, 2d ed., Cold Spring Harbor Laboratory, Cold Spring Harbor, N.Y.). The sequence can be cleaved at appropriate sites with restriction endonuclease(s), followed by further enzymatic modification if desired, isolated, and ligated in vitro. In the production of the gene encoding a derivative or analog of Delta, care should be taken to ensure that the modified gene remains within the same translational reading frame as Delta, uninterrupted by translational stop signals, in the gene region where the desired Delta activity is encoded.

Additionally, the Delta-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C., et al., 1978, J. Biol. Chem 253:6551), use of TAB® linkers (Pharmacia), etc. PCR primers containing sequence changes can be used in PCR to introduce such changes into the amplified fragments.

Manipulations of the Delta sequence may also be made at the protein level. Included within the scope of the invention are Delta protein fragments or other derivatives or analogs which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

In addition, analogs and derivatives of Delta can be chemically synthesized. For example, a peptide corresponding to a portion of a Delta protein which comprises the desired domain (see Section 5.6.1), or which mediates the desired aggregation activity in vitro, or binding to a receptor, can be synthesized by use of a peptide synthesizer. Furthermore, if desired, nonclassical amino acids or chemical amino acid analogs can be introduced as a substitution or addition into the Delta sequence. Non-classical amino acids include but are not limited to the D-isomers of the common amino acids, α-amino isobutyric acid, 4-aminobutyric acid, hydroxyproline, sarcosine, citrulline, cysteic acid, t-butylglycine, t-butylalanine, phenylglycine, cyclohexylalanine, β-alanine, designer amino acids such as β-methyl amino acids, Cα-methyl amino acids, and Nα-methyl amino acids.

In a specific embodiment, the Delta derivative is a chimeric, or fusion, protein comprising a vertebrate Delta protein or fragment thereof (preferably consisting of at least a domain or motif of the Delta protein, or at least 10 amino acids of the Delta protein) joined at its amino- or carboxy-terminus via a peptide bond to an amino acid sequence of a different protein. In one embodiment, such a chimeric protein is produced by recombinant expression of a nucleic acid encoding the protein (comprising a Delta-coding sequence joined in-frame to a coding sequence for a different protein). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer. In a specific embodiment, a chimeric nucleic acid encoding a mature Delta protein with a heterologous signal sequence is expressed such that the chimeric protein is expressed and processed by the cell to the mature Delta protein. As another example, and not by way of limitation, a recombinant molecule can be constructed according to the invention, comprising coding portions of both Delta and another toporythmic gene, e.g., Serrate. The encoded protein of such a recombinant molecule could exhibit properties associated with both Serrate and Delta and portray a novel profile of biological activities, including agonists as well as antagonists. The primary sequence of Delta and Serrate may also be used to predict tertiary structure of the molecules using computer simulation (Hopp and Woods, 1981, Proc. Natl. Acad. Sci. U.S.A. 78:3824–3828); Delta/Serrate chimeric recombinant genes could be designed in light of correlations between tertiary structure and biological function. Likewise, chimeric genes comprising portions of Delta fused to any heterologous protein-encoding sequences may be constructed. A specific embodiment relates to a chimeric protein comprising a fragment of Delta of at least six amino acids.

In another specific embodiment, the Delta derivative is a fragment of vertebrate Delta comprising a region of homology with another toporythmic protein. As used herein, a region of a first protein shall be considered "homologous" to a second protein when the amino acid sequence of the region is at least 30% identical or at least 75% either identical or involving conservative changes, when compared to any sequence in the second protein of an equal number of amino acids as the number contained in the region. For example, such a Delta fragment can comprise one or more regions homologous to Serrate, including but not limited to the DSL domain or a portion thereof.

Other specific embodiments of derivatives and analogs are described in the subsections below and examples sections infra.

5.6.1. Derivatives of Delta Containing One or More Domains of the Protein

In a specific embodiment, the invention relates to vertebrate Delta derivatives and analogs, in particular Delta fragments and derivatives of such fragments, that comprise, or alternatively consist of, one or more domains of the Delta protein, including but not limited to the extracellular domain, signal sequence, region amino-terminal to the DSL domain, DSL domain, ELR domain, transmembrane domain, intracellular domain, and one or more of the EGF-like repeats (ELR) of the Delta protein (e.g., ELRs 1–9), or any combination of the foregoing. In particular examples relating to the chick and mouse Delta proteins, such domains are identified in Examples Section 6 and 7, respectively, and in FIGS. 3A–3B and 9A–9B. Thus, by way of example is provided, a molecule comprising an extracellular domain (approximately amino acids 1–545), signal sequence (approximately amino acids 1–17), region amino-terminal to the DSL domain (approximately amino acids 1–178), the DSL domain (approximately amino acids 179–223), EGF1 (approximately amino acids 229–260), EGF2 (approximately amino acids 261–292), EGF3 (approximately amino acids 293–332), EGF4 (approximately amino acids 333–370), EGF5 (approximately amino acids 371–409), EGF6 (approximately amino acids 410–447), EGF7 (approximately amino acids 448–485), EGF8 (approximately amino acids 486–523), transmembrane domain, and intracellular (cytoplasmic) domain (approximately amino acids 555–728) of a vertebrate Delta.

In a specific embodiment, the molecules comprising specific fragments of vertebrate Delta are those comprising fragments in the respective Delta protein most homologous to specific fragments of the Drosophila or chick Delta protein. In particular embodiments, such a molecule comprises or consists of the amino acid sequences of SEQ ID NO:2 or 23. Alternatively, a fragment comprising a domain of a Delta homolog can be identified by protein analysis methods as described in Section 5.3.2.

5.6.2. Derivatives of Delta that Mediate Binding to Toporythmic Protein Domains The invention also provides for vertebrate Delta fragments, and analogs or derivatives of such fragments, which mediate binding to toporythmic proteins (and thus are termed herein "adhesive"), and nucleic acid sequences encoding the foregoing.

In a particular embodiment, the adhesive fragment of a Delta protein comprises the DSL domain, or a portion thereof. Subfragments within the DSL domain that mediate binding to Notch can be identified by analysis of constructs expressing deletion mutants.

The ability to bind to a toporythmic protein (preferably Notch) can be demonstrated by in vitro aggregation assays with cells expressing such a toporythmic protein as well as cells expressing Delta or a Delta derivative (See Section 5.7). That is, the ability of a Delta fragment to bind to a Notch protein can be demonstrated by detecting the ability of the Delta fragment, when expressed on the surface of a first cell, to bind to a Notch protein expressed on the surface of a second cell.

The nucleic acid sequences encoding toporythmic proteins or adhesive domains thereof, for use in such assays, can be isolated from human, porcine, bovine, feline, avian, equine, canine, or insect, as well as primate sources and any other species in which homologs of known toporythmic genes can be identified.

5.7. Assays of Delta Proteins, Derivatives and Analogs

The functional activity of vertebrate Delta proteins, derivatives and analogs can be assayed by various methods.

For example, in one embodiment, where one is assaying for the ability to bind or compete with wild-type Delta for binding to anti-Delta antibody, various immunoassays known in the art can be used, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labelled. Many means are known in the art for detecting binding in an immunoassay and are within the scope of the present invention.

In another embodiment, where one is assaying for the ability to mediate binding to a toporythmic protein, e.g., Notch, one can carry out an in vitro aggregation assay (see Fehon et al., 1990, Cell 61:523–534; Rebay et al., 1991, Cell 67:687–699).

In another embodiment, where a receptor for Delta is identified, receptor binding can be assayed, e.g., by means well-known in the art. In another embodiment, physiological correlates of Delta binding to cells expressing a Delta receptor (signal transduction) can be assayed.

In another embodiment, in insect or other model systems, genetic studies can be done to study the phenotypic effect of a Delta mutant that is a derivative or analog of wild-type Delta.

Other methods will be known to the skilled artisan and are within the scope of the invention.

5.8. Therapeutic Uses

The invention provides for treatment of disorders of cell fate or differentiation by administration of a therapeutic compound of the invention. Such therapeutic compounds (termed herein "Therapeutics") include: Delta proteins and analogs and derivatives (including fragments) thereof (e.g., as described hereinabove); antibodies thereto (as described hereinabove); nucleic acids encoding the Delta proteins, analogs, or derivatives (e.g., as described hereinabove); and Delta antisense nucleic acids. As stated supra, the Antagonist Therapeutics of the invention are those Therapeutics which antagonize, or inhibit, a Delta function and/or Notch function (since Delta is a Notch ligand). Such Antagonist Therapeutics are most preferably identified by use of known convenient in vitro assays, e.g., based on their ability to inhibit binding of Delta to another protein (e.g., a Notch protein), or inhibit any known Notch or Delta function as preferably assayed in vitro or in cell culture, although genetic assays (e.g., in Drosophila) may also be employed. In a preferred embodiment, the Antagonist Therapeutic is a protein or derivative thereof comprising a functionally active fragment such as a fragment of Delta which mediates binding to Notch, or an antibody thereto. In other specific embodiments, such an Antagonist Therapeutic is a nucleic acid capable of expressing a molecule comprising a fragment of Delta which binds to Notch, or a Delta antisense nucleic acid (see Section 5.11 herein). It should be noted that preferably, suitable in vitro or in vivo assays, as described infra, should be utilized to determine the effect of a specific Therapeutic and whether its administration is indicated for treatment of the affected tissue, since the developmental history of the tissue may determine whether an Antagonist or Agonist Therapeutic is desired.

In addition, the mode of administration, e.g., whether administered in soluble form or administered via its encoding nucleic acid for intracellular recombinant expression, of the Delta protein or derivative can affect whether it acts as an agonist or antagonist.

In another embodiment of the invention, a nucleic acid containing a portion of a Delta gene is used, as an Antagonist Therapeutic, to promote Delta inactivation by homologous recombination (Koller and Smithies, 1989, Proc. Natl. Acad. Sci. USA 86:8932–8935; Zijlstra et al., 1989, Nature 342:435–438).

The Agonist Therapeutics of the invention, as described supra, promote Delta function. Such Agonist Therapeutics include but are not limited to proteins and derivatives comprising the portions of Notch that mediate binding to Delta, and nucleic acids encoding the foregoing (which can be administered to express their encoded products in vivo).

Further descriptions and sources of Therapeutics of the inventions are found in Sections 5.1 through 5.7 herein.

Molecules which retain, or alternatively inhibit, a desired Delta property, e.g., binding to Notch, binding to an intracellular ligand, can be used therapeutically as inducers, or inhibitors, respectively, of such property and its physiological correlates. In a specific embodiment, a peptide (e.g., in the range of 6–50 or 15–25 amino acids; and particularly of about 10, 15, 20 or 25 amino acids) containing the sequence of a portion of Delta which binds to Notch is used to antagonize Notch function. In a specific embodiment, such an Antagonist Therapeutic is used to treat or prevent human or other malignancies associated with increased Notch expression (e.g., cervical cancer, colon cancer, breast cancer, squamous adenocarcimas (see infra)). Derivatives or analogs of Delta can be tested for the desired activity by procedures known in the art, including but not limited to the assays described in the examples infra. For example, molecules comprising Delta fragments which bind to Notch EGF-repeats (ELR) 11 and 12 and which are smaller than a DSL domain, can be obtained and selected by expressing deletion mutants and assaying for binding of the expressed product to Notch by any of the several methods (e.g., in vitro cell aggregation assays, interaction trap system), some of which are described in the Examples Sections infra. In one specific embodiment, peptide libraries can be screened to select a peptide with the desired activity; such screening can be carried out by assaying, e.g., for binding to Notch or a molecule containing the Notch ELR 11 and 12 repeats.

Other Therapeutics include molecules that bind to a vertebrate Delta protein. Thus, the invention also provides a method for identifying such molecules. Such molecules can be identified by a method comprising contacting a plurality of molecules (e.g., in a peptide library, or combinatorial chemical library) with the Delta protein under conditions conducive to binding, and recovering any molecules that bind to the Delta protein.

The Agonist and Antagonist Therapeutics of the invention have therapeutic utility for disorders of cell fate. The Agonist Therapeutics are administered therapeutically (including prophylactically): (1) in diseases or disorders involving an absence or decreased (relative to normal, or desired) levels of Notch or Delta function, for example, in patients where Notch or Delta protein is lacking, genetically defective, biologically inactive or underactive, or underexpressed; and (2) in diseases or disorders wherein in vitro (or in vivo) assays (see infra) indicate the utility of Delta agonist administration. The absence or decreased levels in Notch or Delta function can be readily detected, e.g., by obtaining a patient tissue sample (e.g., from biopsy tissue) and assaying it in vitro for protein levels, structure and/or activity of the expressed Notch or Delta protein. Many methods standard in the art can be thus employed, including but not limited to immunoassays to detect and/or visualize Notch or Delta protein (e.g., Western blot, immunoprecipitation followed by sodium dodecyl sulfate polyacrylamide gel electrophoresis, immunocytochemistry, etc.) and/or hybridization assays to detect Notch or Delta expression by detecting and/or visualizing respectively Notch or Delta mRNA (e.g., Northern assays, dot blots, in situ hybridization, etc.)

In vitro assays which can be used to determine whether administration of a specific Agonist Therapeutic or Antagonist Therapeutic is indicated, include in vitro cell culture assays in which a patient tissue sample is grown in culture, and exposed to or otherwise administered a Therapeutic, and the effect of such Therapeutic upon the tissue sample is observed. In one embodiment, where the patient has a malignancy, a sample of cells from such malignancy is plated out or grown in culture, and the cells are then exposed to a Therapeutic. A Therapeutic which inhibits survival or growth of the malignant cells (e.g., by promoting terminal differentiation) is selected for therapeutic use in vivo. Many assays standard in the art can be used to assess such survival and/or growth; for example, cell proliferation can be assayed by measuring $^3$H-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in morphology, etc. In a specific aspect, the malignant cell cultures are separately exposed to (1) an Agonist Therapeutic, and (2) an Antagonist Therapeutic; the result of the assay can indicate which type of Therapeutic has therapeutic efficacy.

In another embodiment, a Therapeutic is indicated for use which exhibits the desired effect, inhibition or promotion of cell growth, upon a patient cell sample from tissue having or suspected of having a hyper- or hypoproliferative disorder, respectively. Such hyper- or hypoproliferative disorders include but are not limited to those described in Sections 5.8.1 through 5.8.3 infra.

In another specific embodiment, a Therapeutic is indicated for use in treating nerve injury or a nervous system degenerative disorder (see Section 5.8.2) which exhibits in vitro promotion of nerve regeneration/neurite extension from nerve cells of the affected patient type.

In addition, administration of an Antagonist Therapeutic of the invention is also indicated in diseases or disorders determined or known to involve a Notch or Delta dominant activated phenotype ("gain of function" mutations.) Administration of an Agonist Therapeutic is indicated in diseases or disorders determined or known to involve a Notch or Delta dominant negative phenotype ("loss of function" mutations). The functions of various structural domains of the Notch protein have been investigated in vivo, by ectopically expressing a series of Drosophila Notch deletion mutants under the hsp70 heat-shock promoter, as well as eye-specific promoters (see Rebay et al., 1993, Cell 74:319–329). Two classes of dominant phenotypes were observed, one suggestive of Notch loss-of function mutations and the other of Notch gain-of-function mutations. Dominant "activated" phenotypes resulted from overexpression of a protein lacking most extracellular sequences, while dominant "negative" phenotypes resulted from overexpression of a protein lacking most intracellular sequences. The results indicated that Notch functions as a receptor whose extracellular domain mediates ligand-binding, resulting in the transmission of developmental signals by the cytoplasmic domain.

In various specific embodiments, in vitro assays can be carried out with representative cells of cell types involved in a patient's disorder, to determine if a Therapeutic has a desired effect upon such cell types.

In another embodiment, cells of a patient tissue sample suspected of being pre-neoplastic are similarly plated out or grown in vitro, and exposed to a Therapeutic. The Therapeutic which results in a cell phenotype that is more normal (i.e., less representative of a pre-neoplastic state, neoplastic state, malignant state, or transformed phenotype) is selected for therapeutic use. Many assays standard in the art can be used to assess whether a pre-neoplastic state, neoplastic state, or a transformed or malignant phenotype, is present. For example, characteristics associated with a transformed phenotype (a set of in vitro characteristics associated with a tumorigenic ability in vivo) include a more rounded cell morphology, looser substratum attachment, loss of contact inhibition, loss of anchorage dependence, release of proteases such as plasminogen activator, increased sugar transport, decreased serum requirement, expression of fetal antigens, disappearance of the 250,000 dalton surface protein, etc. (see Luria et al., 1978, *General Virology*, 3d Ed., John Wiley & Sons, New York pp. 436–446).

In other specific embodiments, the in vitro assays described supra can be carried out using a cell line, rather than a cell sample derived from the specific patient to be treated, in which the cell line is derived from or displays characteristic(s) associated with the malignant, neoplastic or pre-neoplastic disorder desired to be treated or prevented, or is derived from the neural or other cell type upon which an effect is desired, according to the present invention.

The Antagonist Therapeutics are administered therapeutically (including prophylactically): (1) in diseases or disorders involving increased (relative to normal, or desired) levels of Notch or Delta function, for example, where the Notch or Delta protein is overexpressed or overactive; and (2) in diseases or disorders wherein in vitro (or in vivo) assays indicate the utility of Delta antagonist administration. The increased levels of Notch or Delta function can be readily detected by methods such as those described above, by quantifying protein and/or RNA. In vitro assays with cells of patient tissue sample or the appropriate cell line or cell type, to determine therapeutic utility, can be carried out as described above.

5.8.1. Malignancies

Malignant and pre-neoplastic conditions which can be tested as described supra for efficacy of intervention with Antagonist or Agonist Therapeutics, and which can be treated upon thus observing an indication of therapeutic utility, include but are not limited to those described below in Sections 5.8.1 and 5.9.1.

Malignancies and related disorders, cells of which type can be tested in vitro (and/or in vivo), and upon observing the appropriate assay result, treated according to the present invention, include but are not limited to those listed in Table 1 (for a review of such disorders, see Fishman et al., 1985, *Medicine*, 2d Ed., J.B. Lippincott Co., Philadelphia):

TABLE 1

MALIGNANCIES AND RELATED DISORDERS

Leukemia
acute leukemia acute lymphocytic leukemia
acute myelocytic leukemia myeloblastic
promyelocytic
myelomonocytic TABLE 1-continued

MALIGNANCIES AND RELATED DISORDERS monocytic
erythroleukemia
chronic leukemia chronic myelocytic (granulocytic) leukemia
chronic lymphocytic leukemia
Polycythemia vera
Lymphoma Hodgkin's disease
non-Hodgkin's disease
Multiple myeloma
Waldenström's macroglobulinemia
Heavy chain disease
Solid tumors
sarcomas and carcinomas fibrosarcoma
myxosarcoma
liposarcoma
chondrosarcoma
osteogenic sarcoma
chordoma
angiosarcoma
endotheliosarcoma
lymphangiosarcoma
lymphangioendotheliosarcoma
synovioma
mesothelioma
Ewing's tumor
leiomyosarcoma
rhabdomyosarcoma
colon carcinoma
pancreatic cancer
breast cancer
ovarian cancer
prostate cancer
squamous cell carcinoma
basal cell carcinoma
adenocarcinoma
sweat gland carcinoma
sebaceous gland carcinoma
papillary carcinoma
papillary adenocarcinomas
cystadenocareinoma
medullary carcinoma
bronchogenic carcinoma
renal cell carcinoma
hepatoma
bile duct carcinoma
choriocarcinoma
seminoma
embryonal carcinoma
Wilms' tumor
cervical cancer
testicular tumor
lung carcinoma
small cell lung carcinoma
bladder carcinoma
epithelial carcinoma
glioma
astrocytoma
medulloblastoma
craniopharyngioma
ependymoma
pinealoma
hemangioblastoma
acoustic neuroma
oligodendroglioma
menangioma
melanoma
neuroblastoma
retinoblastoma In specific embodiments, malignancy or dysproliferative changes (such as metaplasias and dysplasias) are treated or prevented in epithelial tissues such as those in the cervix, esophagus, and lung.

Malignancies of the colon and cervix exhibit increased expression of human Notch relative to such non-malignant tissue (see PCT Publication no. WO 94/07474 published Apr. 14, 1994, incorporated by reference herein in its entirety). Thus, in specific embodiments, malignancies or premalignant changes of the colon or cervix are treated or prevented by administering an effective amount of an Antagonist Therapeutic, e.g., a Delta derivative, that antagonizes Notch function. The presence of increased Notch expression in colon, and cervical cancer suggests that many more cancerous and hyperproliferative conditions exhibit upregulated Notch. Thus, in specific embodiments, various cancers, e.g., breast cancer, squamous adenocarcinoma, seminoma, melanoma, and lung cancer, and premalignant changes therein, as well as other hyperproliferative disorders, can be treated or prevented by administration of an Antagonist Therapeutic that antagonizes Notch function.

5.8.2. Nervous System Disorders

Nervous system disorders, involving cell types which can be tested as described supra for efficacy of intervention with Antagonist or Agonist Therapeutics, and which can be treated upon thus observing an indication of therapeutic utility, include but are not limited to nervous system injuries, and diseases or disorders which result in either a disconnection of axons, a diminution or degeneration of neurons, or demyelination. Nervous system lesions which may be treated in a patient (including human and non-human mammalian patients) according to the invention include but are not limited to the following lesions of either the central (including spinal cord, brain) or peripheral nervous systems:

(i) traumatic lesions, including lesions caused by physical injury or associated with surgery, for example, lesions which sever a portion of the nervous system, or compression injuries;

(ii) ischemic lesions, in which a lack of oxygen in a portion of the nervous system results in neuronal injury or death, including cerebral infarction or ischemia, or spinal cord infarction or ischemia;

(iii) malignant lesions, in which a portion of the nervous system is destroyed or injured by malignant tissue which is either a nervous system associated malignancy or a malignancy derived from non-nervous system tissue;

(iv) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis;

(v) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis;

(vi) lesions associated with nutritional diseases or disorders, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration;

(vii) neurological lesions associated with systemic diseases including but not limited to diabetes (diabetic neuropathy, Bell's palsy), systemic lupus erythematosus, carcinoma, or sarcoidosis;

(viii) lesions caused by toxic substances including alcohol, lead, or particular neurotoxins; and (ix) demyelinated lesions in which a portion of the nervous system is destroyed or injured by a demyelinating disease including but not limited to multiple sclerosis, human immunodeficiency virus-associated myelopathy, transverse myelopathy or various etiologies, progressive multifocal leukoencephalopathy, and central pontine myelinolysis.

Therapeutics which are useful according to the invention for treatment of a nervous system disorder may be selected by testing for biological activity in promoting the survival or differentiation of neurons (see also Section 5.8). For example, and not by way of limitation, Therapeutics which elicit any of the following effects may be useful according to the invention:

(i) increased survival time of neurons in culture;

(ii) increased sprouting of neurons in culture or in vivo;

(iii) increased production of a neuron-associated molecule in culture or in vivo, e.g., choline acetyltransferase or acetylcholinesterase with respect to motor neurons; or (iv) decreased symptoms of neuron dysfunction in vivo.

Such effects may be measured by any method known in the art. In preferred, non-limiting embodiments, increased survival of neurons may be measured by the method set forth in Arakawa et al. (1990, J. Neurosci. 10:3507–3515); increased sprouting of neurons may be detected by methods set forth in Pestronk et al. (1980, Exp. Neurol. 70:65–82) or Brown et al. (1981, Ann. Rev. Neurosci. 4:17–42); increased production of neuron-associated molecules may be measured by bioassay, enzymatic assay, antibody binding, Northern blot assay, etc., depending on the molecule to be measured; and motor neuron dysfunction may be measured by assessing the physical manifestation of motor neuron disorder, e.g., weakness, motor neuron conduction velocity, or functional disability.

In a specific embodiments, motor neuron disorders that may be treated according to the invention include but are not limited to disorders such as infarction, infection, exposure to toxin, trauma, surgical damage, degenerative disease or malignancy that may affect motor neurons as well as other components of the nervous system, as well as disorders that selectively affect neurons such as amyotrophic lateral sclerosis, and including but not limited to progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

5.8.3. Tissue Repair and Regeneration

In another embodiment of the invention, a Therapeutic of the invention is used for promotion of tissue regeneration and repair, including but not limited to treatment of benign dysproliferative disorders. Specific embodiments are directed to treatment of cirrhosis of the liver (a condition in which scarring has overtaken normal liver regeneration processes), treatment of keloid (hypertrophic scar) formation (disfiguring of the skin in which the scarring process interferes with normal renewal), psoriasis (a common skin condition characterized by excessive proliferation of the skin and delay in proper cell fate determination), and baldness (a condition in which terminally differentiated hair follicles (a tissue rich in Notch) fail to function properly). In another embodiment, a Therapeutic of the invention is used to treat degenerative or traumatic disorders of the sensory epithelium of the inner ear.

5.9. Prophylactic Uses

5.9.1. Malignancies

The Therapeutics of the invention can be administered to prevent progression to a neoplastic or malignant state, including but not limited to those disorders listed in Table 1. Such administration is indicated where the Therapeutic is shown in assays, as described supra, to have utility for treatment or prevention of such disorder. Such prophylactic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, *Basic Pathology*, 2d Ed., W.B. Saunders Co., Philadelphia, pp. 68–79.) Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a patient, can indicate the desirability of prophylactic/therapeutic administration of a Therapeutic of the invention. As mentioned supra, such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. (see also id., at pp. 84–90 for characteristics associated with a transformed or malignant phenotype).

In a specific embodiment, leukoplakia, a benign-appearing hyperplastic or dysplastic lesion of the epithelium, or Bowen's disease, a carcinoma in situ, are pre-neoplastic lesions indicative of the desirability of prophylactic intervention.

In another embodiment, fibrocystic disease (cystic hyperplasia, mammary dysplasia, particularly adenosis (benign epithelial hyperplasia)) is indicative of the desirability of prophylactic intervention.

In other embodiments, a patient which exhibits one or more of the following predisposing factors for malignancy is treated by administration of an effective amount of a Therapeutic: a chromosomal translocation associated with a malignancy (e.g., the Philadelphia chromosome for chronic myelogenous leukemia, t(14;18) for follicular lymphoma, etc.), familial polyposis or Gardner's syndrome (possible forerunners of colon cancer), benign monoclonal gammopathy (a possible forerunner of multiple myeloma), and a first degree kinship with persons having a cancer or precancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, 1976, *Basic Pathology*, 2d Ed., W.B. Saunders Co., Philadelphia, pp. 112–113) etc.)

In another specific embodiment, an Antagonist Therapeutic of the invention is administered to a human patient to prevent progression to breast, colon, or cervical cancer.

5.9.2. Other Disorders

In other embodiments, a Therapeutic of the invention can be administered to prevent a nervous system disorder described in Section 5.8.2, or other disorder (e.g., liver cirrhosis, psoriasis, keloids, baldness) described in Section 5.8.3.

5.10. Demonstration of Therapeutic or Prophylactic Utility

The Therapeutics of the invention can be tested in vivo for the desired therapeutic or prophylactic activity. For example, such compounds can be tested in suitable animal model systems prior to testing in humans, including but not limited to rats, mice, chicken, cows, monkeys, rabbits, etc. For in vivo testing, prior to administration to humans, any animal model system known in the art may be used.

5.11. Antisense Regulation of Delta Expression

The present invention provides the therapeutic or prophylactic use of nucleic acids of at least six nucleotides that are antisense to a gene or cDNA encoding Delta or a portion thereof. "Antisense" as used herein refers to a nucleic acid capable of hybridizing to a portion of a Delta RNA (preferably mRNA) by virtue of some sequence complementarity. Such antisense nucleic acids have utility as Antagonist Therapeutics of the invention, and can be used in the treatment or prevention of disorders as described supra in Section 5.8 and its subsections.

The antisense nucleic acids of the invention can be oligonucleotides that are double-stranded or single-stranded, RNA or DNA or a modification or derivative thereof, which can be directly administered to a cell, or which can be produced intracellularly by transcription of exogenous, introduced sequences.

In a specific embodiment, the Delta antisense nucleic acids provided by the instant invention can be used for the treatment of tumors or other disorders, the cells of which tumor type or disorder can be demonstrated (in vitro or in vivo) to express a Delta gene or a Notch gene. Such demonstration can be by detection of RNA or of protein.

The invention further provides pharmaceutical compositions comprising an effective amount of the Delta antisense nucleic acids of the invention in a pharmaceutically acceptable carrier, as described infra in Section 5.12. Methods for treatment and prevention of disorders (such as those described in Sections 5.8 and 5.9) comprising administering the pharmaceutical compositions of the invention are also provided.

In another embodiment, the invention is directed to methods for inhibiting the expression of a Delta nucleic acid sequence in a prokaryotic or eukaryotic cell comprising providing the cell with an effective amount of a composition comprising an antisense Delta nucleic acid of the invention.

Delta antisense nucleic acids and their uses are described in detail below.

5.11.1. Delta Antisense Nucleic Acids

The Delta antisense nucleic acids are of at least six nucleotides and are preferably oligonucleotides (ranging from 6 to about 50 oligonucleotides). In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide may include other appending groups such as peptides, or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO 88/09810, published Dec. 15, 1988) or blood-brain barrier (see, e.g., PCT Publication No. WO 89/10134, published Apr. 25, 1988), hybridization-triggered cleavage agents (see, e.g., Krol et al., 1988, BioTechniques 6:958–976) or intercalating agents (see, e.g., Zon, 1988, Pharm. Res. 5:539–549).

In a preferred aspect of the invention, a Delta antisense oligonucleotide is provided, preferably of single-stranded DNA. In a most preferred aspect, such an oligonucleotide comprises a sequence antisense to the sequence encoding an SH3 binding domain or a Notch-binding domain of Delta, most preferably, of human Delta. The oligonucleotide may be modified at any position on its structure with substituents generally known in the art.

The Delta antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

In another embodiment, the oligonucleotide comprises at least one modified sugar moiety selected from the group including but not limited to arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641).

The oligonucleotide may be conjugated to another molecule, e.g., a peptide, hybridization triggered cross-linking agent, transport agent, hybridization-triggered cleavage agent, etc.

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

In a specific embodiment, the Delta antisense oligonucleotide comprises catalytic RNA, or a ribozyme (see, e.g., PCT International Publication WO 90/11364, published Oct. 4, 1990; Sarver et al., 1990, Science 247:1222–1225). In another embodiment, the oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

In an alternative embodiment, the Delta antisense nucleic acid of the invention is produced intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the Delta antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the Delta antisense RNA can be by any promoter known in the art to act in mammalian, preferably human, cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), etc.

The antisense nucleic acids of the invention comprise a sequence complementary to at least a portion of an RNA transcript of a Delta gene, preferably a human Delta gene. However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded Delta antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a Delta RNA it may contain and still form a stable duplex (or triplex, as the case may be). One skilled in the art can ascertain a tolerable degree of mismatch by use of standard procedures to determine the melting point of the hybridized complex.

5.11.2. Therapeutic Utility of Delta Antisense Nucleic Acids

The Delta antisense nucleic acids can be used to treat (or prevent) malignancies or other disorders, of a cell type which has been shown to express Delta or Notch. In specific embodiments, the malignancy is cervical, breast, or colon cancer, or squamous adenocarcinoma. Malignant, neoplastic, and pre-neoplastic cells which can be tested for such expression include but are not limited to those described supra in Sections 5.8.1 and 5.9.1. In a preferred embodiment, a single-stranded DNA antisense Delta oligonucleotide is used.

Malignant (particularly, tumor) cell types which express Delta or Notch RNA can be identified by various methods known in the art. Such methods include but are not limited to hybridization with a Delta or Notch-specific nucleic acid (e.g. by Northern hybridization, dot blot hybridization, in situ hybridization), observing the ability of RNA from the cell type to be translated in vitro into Notch or Delta, immunoassay, etc. In a preferred aspect, primary tumor tissue from a patient can be assayed for Notch or Delta expression prior to treatment, e.g., by immunocytochemistry or in situ hybridization.

Pharmaceutical compositions of the invention (see Section 5.12), comprising an effective amount of a Delta antisense nucleic acid in a pharmaceutically acceptable carrier, can be administered to a patient having a malignancy which is of a type that expresses Notch or Delta RNA or protein.

The amount of Delta antisense nucleic acid which will be effective in the treatment of a particular disorder or condition will depend on the nature of the disorder or condition, and can be determined by standard clinical techniques. Where possible, it is desirable to determine the antisense cytotoxicity of the tumor type to be treated in vitro, and then in useful animal model systems prior to testing and use in humans.

In a specific embodiment, pharmaceutical compositions comprising Delta antisense nucleic acids are administered via liposomes, microparticles, or microcapsules. In various embodiments of the invention, it may be useful to use such compositions to achieve sustained release of the Delta antisense nucleic acids. In a specific embodiment, it may be desirable to utilize liposomes targeted via antibodies to specific identifiable tumor antigens (Leonetti et al., 1990, Proc. Natl. Acad. Sci. U.S.A. 87:2448–2451; Renneisen et al., 1990, J. Biol. Chem. 265:16337–16342).

5.12. Therapeutic/Prophylactic Administration and Compositions

The invention provides methods of treatment (and prophylaxis) by administration to a subject of an effective amount of a Therapeutic of the invention. In a preferred aspect, the Therapeutic is substantially purified. The subject is preferably an animal, including but not limited to animals such as cows, pigs, chickens, etc., and is preferably a mammal, and most preferably human.

Various delivery systems are known and can be used to administer a Therapeutic of the invention, e.g., encapsulation in liposomes, microparticles, microcapsules, expression by recombinant cells, receptor-mediated endocytosis (see, e.g., Wu and Wu, 1987, J. Biol. Chem. 262:4429–4432), construction of a Therapeutic nucleic acid as part of a retroviral or other vector, etc. Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

In another embodiment, the Therapeutic can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.)

In yet another embodiment, the Therapeutic can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (Science 249:1527–1533 (1990)).

In a specific embodiment where the Therapeutic is a nucleic acid encoding a protein Therapeutic, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864–1868), etc. Alternatively, a nucleic acid Therapeutic can be introduced intracellularly and incorporated within host cell DNA for expression, by homologous recombination.

In specific embodiments directed to treatment or prevention of particular disorders, preferably the following forms of administration are used:

| Disorder | Preferred Forms of Administration |
|---|---|
| Cervical cancer | Topical |
| Gastrointestinal cancer | Oral; intravenous |
| Lung cancer | Inhaled; intravenous |
| Leukemia | Intravenous; extracorporeal |
| Metastatic carcinomas | Intravenous; oral |
| Brain cancer | Targeted; intravenous; intrathecal |
| Liver cirrhosis | Oral; intravenous |
| Psoriasis | Topical |
| Keloids | Topical |
| Baldness | Topical |
| Spinal cord injury | Targeted; intravenous; intrathecal |
| Parkinson's disease | Targeted; intravenous; intrathecal |
| Motor neuron disease | Targeted; intravenous; intrathecal |
| Alzheimer's disease | Targeted; intravenous; intrathecal |

The present invention also provides pharmaceutical compositions. Such compositions comprise a therapeutically effective amount of a Therapeutic, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The Therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the Therapeutic of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20–500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

5.13. Diagnostic Utility

Delta proteins, analogues, derivatives, and subsequences thereof, Delta nucleic acids (and sequences complementary thereto), anti-Delta antibodies, have uses in diagnostics. Such molecules can be used in assays, such as immunoassays, to detect, prognose, diagnose, or monitor various conditions, diseases, and disorders affecting Delta expression, or monitor the treatment thereof. In particular, such an immunoassay is carried out by a method comprising contacting a sample derived from a patient with an anti-Delta antibody under conditions such that immunospecific binding can occur, and detecting or measuring the amount of any immunospecific binding by the antibody. In a specific aspect, such binding of antibody, in tissue sections, preferably in conjunction with binding of anti-Notch antibody can be used to detect aberrant Notch and/or Delta localization or aberrant levels of Notch-Delta colocalization in a disease state. In a specific embodiment, antibody to Delta can be used to assay in a patient tissue or serum sample for the presence of Delta where an aberrant level of Delta is an indication of a diseased condition. Aberrant levels of Delta binding ability in an endogenous Notch protein, or aberrant levels of binding ability to Notch (or other Delta ligand) in an endogenous Delta protein may be indicative of a disorder of cell fate (e.g., cancer, etc.) By "aberrant levels," is meant increased or decreased levels relative to that present, or a standard level representing that present, in an analogous sample from a portion of the body or from a subject not having the disorder.

The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few.

Delta genes and related nucleic acid sequences and subsequences, including complementary sequences, and other toporythmic gene sequences, can also be used in hybridization assays. Delta nucleic acid sequences, or subsequences thereof comprising about at least 8 nucleotides, can be used as hybridization probes. Hybridization assays can be used to detect, prognose, diagnose, or monitor conditions, disorders, or disease states associated with aberrant changes in Delta expression and/or activity as described supra. In particular, such a hybridization assay is carried out by a method comprising contacting a sample containing nucleic acid with a nucleic acid probe capable of hybridizing to Delta DNA or RNA, under conditions such that hybridization can occur, and detecting or measuring any resulting hybridization.

Additionally, since Delta binds to Notch, Delta or a binding portion thereof can be used to assay for the presence and/or amounts of Notch in a sample, e.g., in screening for malignancies which exhibit increased Notch expression such as colon and cervical cancers.

6. A Delta Homolog in the Chick is Expressed in Prospective Neurons

As described herein, we have isolated and characterized a chick Delta homologue, C-Delta-1. We show that C-Delta-1 is expressed in prospective neurons during neurogenesis, as new cells are being born and their fates decided. Our data in the chick, suggest that both the Delta/Notch signalling mechanism and its role in neurogenesis have been conserved in vertebrates.

6.1. Cloning of C-Delta-1

We identified a chick Delta homologue, C-Delta-1, using the polymerase chain reaction (PCR) and degenerate oligonucleotide primers (FIGS. 1A1–1A3, 1B1–1B2 and 2, SEQ ID NOS:1, 2, 3 and 4). C-Delta-1 was cloned by PCR using the degenerate oligonucleotide primers TTCGGITT(C/T)ACITGGCCIGGIAC (SEQ ID NO:81) and TCIATGCAIGTICCICC(A/G)TT (SEQ ID NO:82) which correspond to the fly Delta protein sequences FGFTWPGT (SEQ ID NO:83) and NGGTCID (SEQ ID NO:84), respectively (Vässin et al., 1987, EMBO J. 6:3431–3440; Kopczynski et al., 1988, Genes Dev. 2:1723–1735). The initial reaction used 50 ng of first-strand oligo-d(T)-primed cDNA from stage 4–6 embryos, 1 g of each primer, 0.2 mM dNTPs, 2U. of Taq polymerase, in 50 1 of the supplied buffer (Perkin-Elmer). 40 cycles of amplification were performed at 94° C./30 sec; 50° C./2 min; 72° C./2 min. Amplified DNA fragments were separated on an agarose gel, cloned in Bluescript pKS—(Stratagene) and sequenced. Two Delta homologs were identified, one of which (C-Delta-1) is expressed in the nervous system. Of the homolog that is expressed in the nervous system, two variants were identified that differ at the carboxy-terminal end of the encoded protein due to an alternative splicing event at the 3' end of the C-Delta-1 gene. One encoded protein has 12 extra amino acids at the carboxy-terminal end, relative to the other encoded protein. The sequence of the shorter encoded variant is set forth in SEQ ID NO:2. The longer variant encoded by SEQ ID NO:3 and identified by the amino acid sequence of SEQ ID NO:4, consists of the amino acid sequence of SEQ ID NO:2 plus twelve additional amino acids at the 3' end (SIPPGSRTSLGV) (SEQ ID NO:85). The longer variant was used in the experiments described below. When tested for biological activity by injection of RNA into Xenopus oocytes, each of the variants had the same biological activity.

DNA fragments corresponding to C-Delta-1 were used to screen a stage 17 spinal cord cDNA library and several full-length clones were obtained and sequenced. We amplified DNA fragments from chick C-Notch-1 gene by similar methods (data not shown); partial sequence data and pattern of expression indicate close similarity to the rodent Notch-1 gene (Weinmaster et al., 1991, Development 113:199–205; Weinmaster et al., 1992, Development 116:931–941; Lardelli & Lendahi, 1993, Exp. Cell Res. 204:364–372). Sequences were analyzed using the Wisconsin GCG set of programs. The GenBank Accession number for the Chick Delta-1 mRNA is U26590. The DNA sequence of C-Delia-1 corresponds to a protein of 722 amino acids, structurally homologous to Drosophila Delta (FIGS. 3A–3B, 4) and clearly distinct from vertebrate homologs of the Delta-related Serrate protein, which we have also cloned (data not shown). C-Delta-1 contains a putative transmembrane domain, a signal sequence and 8 EGF-like repeats in its extracellular region (one repeat less than Drosophila Delta). The amino-terminal domain of C-Delta-1 is closely related to a similar domain in the fly Delta protein, described as necessary and sufficient for in vitro binding to Notch (Muskavitch, 1994, Dev. Biol. 166:415–430). This conserved region includes the so-called DSL motif (FIG. 4) (Henderson et al., 1994, Development 120:2913–2924; Tax et al., 1994, Nature 368:150–154), shared by all known members of the family of presumed ligands of Notch-like proteins (Delta and Serrate in Drosophila; Lag-2 and Apx-1 in *Caenorhabditis elegans*) (Henderson et al., 1994, Development 120:2913–2924; Tax et al., 1994, Nature 368:150–154; Fleming et al., 1990, Genes Dev. 4:2188–2201; Thomas et al., 1991, Development 111:749–761; Mello et al., 1994, Cell 77:95–106). A second cysteine-rich N-terminal region is conserved between the fly and chick proteins, but absent from the related *C. elegans* proteins (FIG. 4). The Xenopus Delta-1 homologue, X-Delta-1 which encodes a protein that is 81% identical to C-Delta-1 and shows all the above structural motifs (FIGS. 3A–3B), has also been cloned. The structural conservation between the chick and fly Delta proteins, including domains identified as critical for Notch binding (Muskavitch, 1994, Dev. Biol. 166:415–430), suggests that C-Delta-1 functions as a ligand for a chick Notch protein, and that a Delta/Notch-mediated mechanism of lateral inhibition might operate in the chick.

6.2. C-Delta-1 and C-Notch-1 Expression Correlates with Onset of Neurogenesis During Drosophila neurogenesis, Delta is transiently expressed in neural precursors, inhibiting neighboring Notch-expressing cells from also becoming neural (Haenlin et al., 1990, Development 110:905–914; Kooh et al., 1993, Development 117:493–507). If C-Delta-1 acts similarly during chick neurogenesis, it should also be transiently expressed in neuronal precursor cells, while these are becoming determined. An analysis of C-Delta-1 expression in the developing CNS indicates that this is indeed the case.

In summary, wholemount in situ hybridization was performed. Formaldehyde fixed embryos were treated with protease and refixed with 4% formaldehyde/0.1% glutaraldehyde. Hybridization with DIG-labelled RNA probes was performed under stringent conditions (1.3×SSC, 50% formamide, 65° C., pH5) in a buffer containing 0.2% Tween-20 and 0.5% CHAPS. Washed embryos were treated with Boehringer Blocking Reagent and incubated overnight in alkaline phosphatase-coupled anti-DIG antibody. After extensive washes, embryos were stained from 30 min to overnight. The embryo in FIG. 5e was wax-sectioned after hybridization.

Figure 5A:
FIG. 5A–5E. C-Delta-1 and C-Notch-1 expression correlate with onset of neurogenesis in the one-day (E1) neural plate. Anterior is to the left. Wholemount in situ hybridization specimens are shown in FIGS. 5a–d; 5e is a section.
Figure 5B:
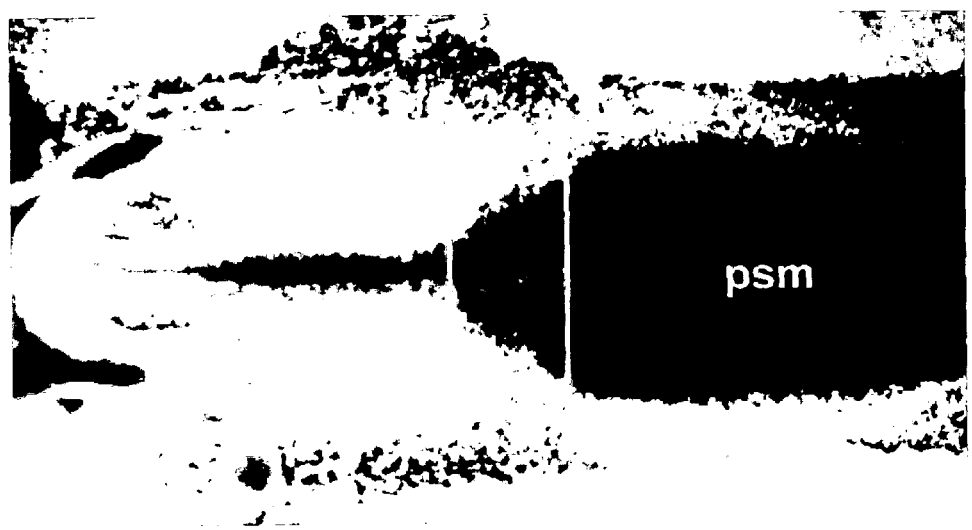
Figure 5C:
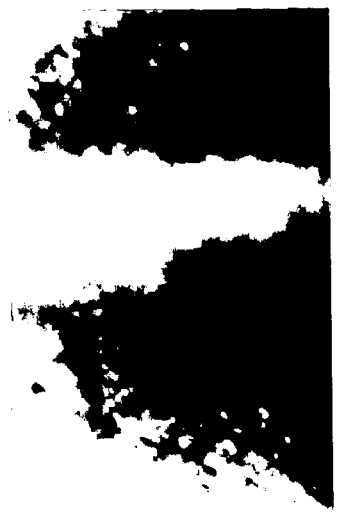

C-Delta-1 expression in the neural plate is first detected at stage 6–7 (31 h, 0/1 somite), in scattered cells just anterior to the presomitic mesoderm (FIGS. 5b, 5c). This region gives rise to the mid/posterior hindbrain, where the earliest differentiated CNS neurons are first detected by a neurofilament antibody at stage 9 (31 h, 7–9 somites) (Sechrist & Bronner-Fraser, 1991, Neuron 7:947–963), 6 h after the initial C-Delta-1 expression (Table 2).

TABLE 2

| Neural tube domains | Hamburger-Hamilton Stage (nominal age in h; somite nos.) | | |
|---|---|---|---|
| | End final S-phase | Initial C-Delta-1 expression | Initial NF expression |
| Mid/posterior Hindbrain | 4 (19 h; 0) | 6 (24 h; 0) | 9 (31 h; 7–9) |
| Spinal cord, somites 5–8 | 6 (24 h; 0) | 8 (28 h; 4–6) | 10 (36 h; 10–12) |
| Forebrain/Midbrain | 7 (25 h; 1–3) | 8 (28 h; 4–6) | 10 (36 h; 10–12) |
| Spinal cord, somites 9–12 | 8 (28 h; 4–6) | 9 (31 h; 7–9) | 11 (43 h; 13–15) |

Figure 5D:
Figure 5E:

As neurogenesis proceeds, expression of C-Delta-1 continues to foreshadow the spatio-temporal pattern of neuronal differentiation (Table 2), spreading posteriorly along the spinal cord and anteriorly into the midbrain and forebrain (FIGS. 5d, 5e). For example, the most posterior expressing cells in the stage 8 spinal cord are at the level of the prospective 6th somite, 6–8 h before the first neurons at that level express neurofilament antigen (Sechrist & Bronner-Fraser, 1991, Neuron 7:947–963) (Table 2). Table 2 shows that the appearance of C-Delta-1 expression closely follows the withdrawal of the first neuronal precursors from the division cycle and precedes the appearance of neurofilament (NF) antigen in the resultant differentiating neurons. Mid-hindbrain comprises rhombomeres 4–6, the level of the otic primordium; posterior hindbrain includes rhombomeres 7 and 8, and somites 1–4. Data for the timing of withdrawal from cell-division and for neurofilament expression are taken from Sechrist et al., 1991, Neuron 7:947–963. In all cases, C-Delta-1 is expressed in scattered cells within domains of uniform C-Notch-1 expression (FIG. 5a).

6.3. Localization and Time-Course Expression of C-Delta-1

Figure 6A:
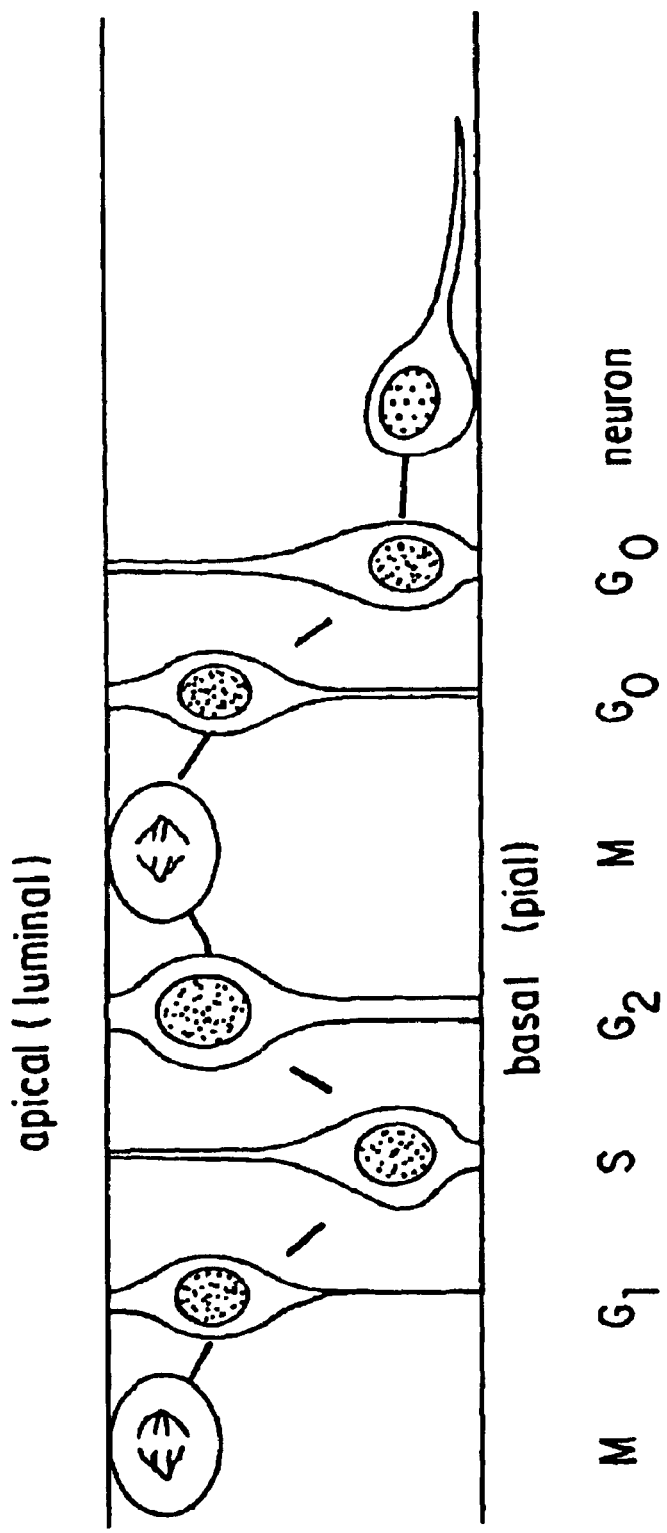
FIGS. 6A–6C. C-Delta-1-expressing cells do not incorporate BrdU. Of 612 C-Delta-b $1^+$ cells, 581 were BrdU⁻ (76 sections; 6 embryos).
Figure 6B:
Figure 6C:
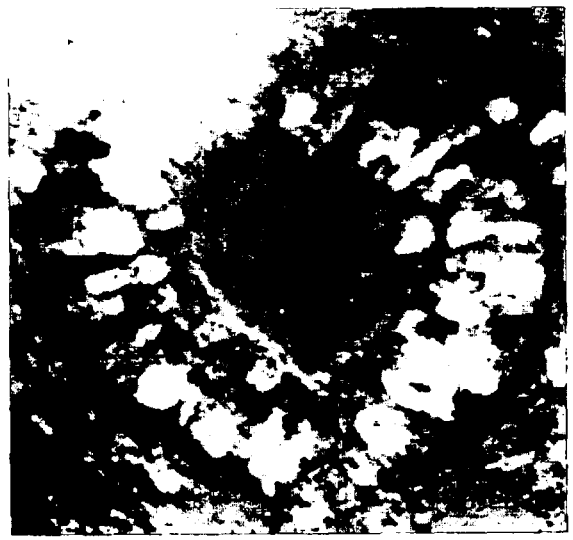

The localization and time-course of C-Delta-1 expression indicate that the gene is switched on at an early step in neurogenesis, and that the cells expressing C-Delta-1 are prospective neurons that have not yet begun to display differentiation markers. To test this hypothesis, we made use of the observations of Sechrist and Bronner-Fraser (Sechrist & Bronner-Fraser, 1991, Neuron 7:947–963) that prospective neurons are the only non-cycling cells in the early neural tube. They finish their final S phase 11–15 h before expressing neurofilament antigen (Table 2) and their nuclei, after completing a last mitosis, adopt a characteristic location near the basal surface of the neuroepithelium, where all the other cell nuclei are in S-phase (Sechrist & Bronner-Fraser, 1991, Neuron 7:947–963; Martin & Langman, 1965, J. Embryol. Exp. Morphol. 14:23–35) (FIG. 6a). We labelled stage 7–9 embryos with bromodeoxyuridine (BrdU), and double-stained for BrdU incorporation and C-Delta-1 expression. 95% of the C-Delta-1-expressing cells were unlabelled, with their nuclei predominantly located near the basal surface, where most other nuclei were BrdU-labelled (FIGS. 6b, 6c). 75 µl 0.1 mM BrdU in PBS was dropped onto stage 7–9 embryos which were incubated at 38° C. for 2–4 h before fixation for in situ hybridization. 15 µm cryostat sections were hybridized with DIG-labelled RNA probes, essentially according to the method of Strähle et al. (Strähle et al., 1994, Trends In Genet. Sci. 10:75–76). After staining, slides were washed in PBS, and processed for BrdU immunodetection (Biffo et al., 1992, Histochem. Cytochem. 40:535–540). Anti-BrdU (1:1000; Sigma) was detected using FITC-coupled goat anti-mouse secondary antibody (Cappel). C-Delta-1 expression was examined by DIC microscopy, and BrdU-labelling by conventional and confocal fluorescence microscopy. These results imply that C-Delta-1 is expressed in cells that have withdrawn from the cell cycle and must indeed be prospective neurons. The few BrdU$^+$/C-Delta-1$^+$ cells have their nuclei outside the basal zone; these may be cells that finished their final S-phase soon after exposure to BrdU, moved apically to complete their final mitosis, and switched on C-Delta-1 expression. C-Delta-1 is also expressed in the later neural tube and peripheral nervous system. Again, the timing of expression and the location of the expressing cells imply that they are neuronal precursors that have not yet begun to differentiate (data not shown). Thus, C-Delta-1 expression appears to be the earliest known marker for prospective neurons.

In addition, the transcription pattern of both C-Delta-1 and C-Serrate-1 overlap that of C-Notch-1 in many regions of the embryo (data not shown) which suggest that C-Notch-1, like Notch in Drosophila, is a receptor for both proteins. In particular, all three genes are expressed in the neurogenic region of the developing central nervous system, and here a striking relationship is seen: the expression of both C-Serrate-1 and C-Delta-1 is confined to the domain of C-Notch-1 expression; but within this domain, the regions of C-Serrate-1 and C-Delta-1 are precisely complementary. The overlapping expression patterns suggest conservation of their functional relationship with Notch and imply that development of the chick and in particular the central nervous system involves the concerted interaction of C-Notch-1 with different ligands at different locations.

6.4. Discussion

The Xenopus homolog of C-Delta-1 has been cloned in a similar manner. In brief, a PCR fragment of X-Delta-1 was isolated and sequenced. This fragment was then used to identify the full length clone of X-Delta-1. The X-Delta-1 expression pattern was studied. It was shown that X-Delta-1 is expressed in scattered cells in the domain of the neural plate where primary neuronal precursors are being generated, suggesting that the cells expressing X-Delta-1 are the prospective primary neurons. In addition, X-Delta-1 is also expressed at other sites and times of neurogenesis, including the anterior neural plate and neurogenic placodes and later stages of neural tube development when secondary neurons are generated. Ectopic X-Delta-1 activity inhibited production of primary neurons; interference with endogenous X-Delta-1 activity resulted in overproduction of primary neurons. These results show that X-Delta-1 mediates lateral inhibition delivered by prospective neurons to adjacent cells. It was shown that ectopic expression of X-Delta-1 in Xenopus eggs suppresses primary neurogenesis, and that ectopic expression of a truncated X-Delta-1 protein which retains only two amino acids of the cytoplasmic domain interferes with endogenous signalling and leads to extra cells developing as neuronal precursors. (Chitnis et al., Nature (in press). Preliminary evidence indicates that C-Delta-1 has a similar inhibitory action when expressed in Xenopus embryos (data not shown). We propose that C-Delta-1, like its Drosophila and Xenopus counterparts, mediates lateral inhibition throughout neurogenesis to restrict the proportion of cells that, at any time, become committed to a neural fate. C-Delta-1 is generally expressed during neurogenesis in many other sites, in both the CNS and PNS, and, for example, the developing ear. It has been shown in the CNS that C-Notch is expressed in the ventricular zone of the E5 chick hindbrain, in dividing cells adjacent to the lumen of the neural tube. C-Delta-1 is expressed in the adjacent layer of cells, which have stopped dividing and are becoming committed as neuronal precursor cells. Thus, Delta/Notch signalling could act here, as in other neural tissues, to maintain a population of uncommitted cycling neuronal stem cells.

7. Isolation and Characterization of a Mouse Delta Homolog

A mouse Delta homolog, termed M-Delta-1, was isolated as follows:
Mouse Delta-1 gene
Tissue Origin: 8.5 and 9.5-day mouse embryonic RNA
Isolation Method:
  a) random primed cDNA against above RNA
  b) PCR of above cDNA using
     PCR primer 1: GGITTCACITGGCCIGGIACNTT (SEQ ID NO:86) [encoding GFTWPGTF (SEQ ID NO:94), a region which is specific for Delta-, not Serrate-like proteins]
     PCR primer 2: GTICCICC(G/A)TT(C/T)TT(G/A)CAIGG(G/A)TT (SEQ ID NO:87) [encoding NPCKNGGT (SEQ ID NO:88), a sequence present in many of the EGF-like repeats]
     Amplification conditions: 50 ng cDNA, 1 µg each primer, 0.2 mM dNTP's, 1.8 U Taq (Perkin-Elmer) in 50 µl of supplied buffer. 40 cycles of: 94° C./30 sec, 45° C./2 min, 72° C./1 min extended by 2 sec each cycle.

The amplified fragment was an approximately 650 base pair fragment which was partially sequenced to determine its relationship to C-Delta-1.

c) a mouse 11.5 day cDNA library (Clontech) was screened. Of several positive clones, one (pMDL2; insert size approximately 4 kb) included the complete protein-coding region whose DNA sequence was completely determined.

FIGS. 7A–7B (SEQ ID NO:11) show the nucleotide sequence of the isolated clone containing M-Delta-1 DNA.

FIG. 8 (SEQ ID NO:12) shows the predicted amino acid sequence of M-Delta-1.

FIGS. 9A–9B show an amino acid alignment of the predicted amino acid sequences for M-Delta-1 and C-Delta-1. Identical amino acids are boxed showing the extensive sequence homology. The consensus sequence is shown below (SEQ ID NO:13).

Expression pattern: The expression pattern was determined to be essentially the same as that observed for C-Delta-1, in particular, in the presomitic mesoderm, central nervous system, peripheral nervous system, and kidney.

8. Isolation and Characterization of a Human Delta Homolog

A human Delta-1 homolog, termed H-Delta-1 (HD1), was isolated as follows:

A human genomic library with inserts ranging in size from 100–150 kb was probed with an EcoRI fragment of the mouse Delta-1 (M-Delta-1) gene. From the library a genomic human PAC clone was isolated which hybridized to the EcoRI fragment. Next, two degenerate oligonucleotides were used to amplify by PCR a fragment of the genomic human PAC clone. The degenerate oligos were:

```
5' ACIATGAA(C/T)AA(C/T)CTIGCIAA(C/T)TG            (SEQ ID NO:89)
[encoding TMNNLANC (SEQ ID NO:90)] and 3' AC(A/G)TAIACIGA(C/T)TG(A/G)TA(C/T)TTIGT        (SEQ ID NO:91)
[encoding TKYQSVYV (SEQ ID NO:92)] or 3' GC(A/G/T)ATIAC(A/G)CA(C/T)TC(A/G)TC(C/T)TT(C/T)TC  (SEQ ID NO:93)
[encoding EKDECVIA (SEQ ID NO:25)].
```

On the basis of the cDNA sequences for chicken and mouse Della-1, it was expected that fragments of approximately 354 and 387 base pairs would be isolated, using the 5' and the two different 3' oligos, respectively. In fact, however, two single isolates of 525 base pairs and another that was 30 base pairs smaller, as expected, were obtained. The larger isolate was sequenced by dideoxy sequencing. The nucleotide sequence is shown in FIGS. 10A–10B (SEQ ID NO:14). Also shown in FIGS. 10A–10B are the predicted amino acid sequences of the amplified DNA fragment (SEQ ID NOS:15–22) for the three different readings frames. Due to sequencing errors, the full uninterrupted sequence between both primers was not identified. As a consequence, one cannot predict the amino acid sequence directly from the DNA sequence obtained. However, FIG. 11 shows the amino acid sequence homology between human Delta-1 (top line) (SEQ ID NO:23 and chick Delta-1 (bottom line) as determined by eye. Because of the sequencing errors, the homology was obtained by switching amongst the three different reading frames to identify the homologous regions.

Using the larger isolate (SEQ ID NO:14) as probe, a human fetal brain plasmid library (Clontech) was screened in an attempt to isolate full-length H-Delta-1 (HD1) genes. This yielded four positive plaques. Two of these positives (HD13 and HD124) survived rescreening and reacted positively with a large human genomic fragment on a Southern Blot. These positive clones were subcloned by digesting with EcoRI and ligating the fragments into a Bluescript KS⁻ vector. The nucleotide sequences of the inserts were obtained by dideoxy sequencing using T3 and T7 primers. The results showed that HD124 was homologous to chicken Delta-1 at both ends; however, one end of HD13 showed no homology. Restriction digestions with a panel of enzymes showed very similar patterns between the two clones, each of which had an insert of about 2 kb, but with differences at the 3' end of HD13.

HD13 and HD124 were cut with BstXI, XbaI, HindIII and XhoI and the restriction fragments were inserted into Bluescript KS⁻, and then sequenced as described above to obtain internal sequence. The sequence that was obtained represents the 3' about 2000 bases of HD1, extending into the 3' non-coding region. HD13 is contained within HD124; however, the added sequence at the 5' end of HD13 is likely due to a cloning artifact.

Since the sequence thus obtained did not contain the 5' end of HD1, HD124 was used as a probe for subsequent hybridizations in a T cell library and in another fetal brain library (Lambda-Zap, Stratagene). A screen of the T cell library resulted in no positives. However, screening the Lambda-Zap library resulted in two positive clones, HD113 and HD118. These clones were inserted into a Bluescript KS—vector using EcoRI as described above. The inserts were digested with a panel of restriction enzymes for comparison with HD13 and HD124, and the 5' and 3' ends were sequenced using T3 and T7 primers. HD113 was determined to be only a small piece of cDNA that when sequenced showed no homology to any known Delta. However, HD118 was 3 kb in length, and included the entire sequence of HD124 with additional 5' sequences. A set of clones were isolated using nested deletions from HD118; these clones were then subjected to dideoxy sequencing using an automated sequencer. FIGS. 12A1–12A3 present the partial nucleotide contig sequence (SEQ ID NO:26) of human Delta obtained from clone HD118. Due to sequencing errors, the full uninterrupted nucleotide sequence of human Delta was not determined. FIGS. 12B1–12B6 show the partial nucleotide contig sequence (SEQ ID NO:26) of human Delta (top line), with the predicted amino acid sequence in three different reading frames presented below, the second line being reading frame 1 (SEQ ID NOS:27–42), the third line being reading frame 2 (SEQ ID NOS:43–47), and the fourth line being reading frame 3 (SEQ ID NOS:48–64).

Figure 14A:
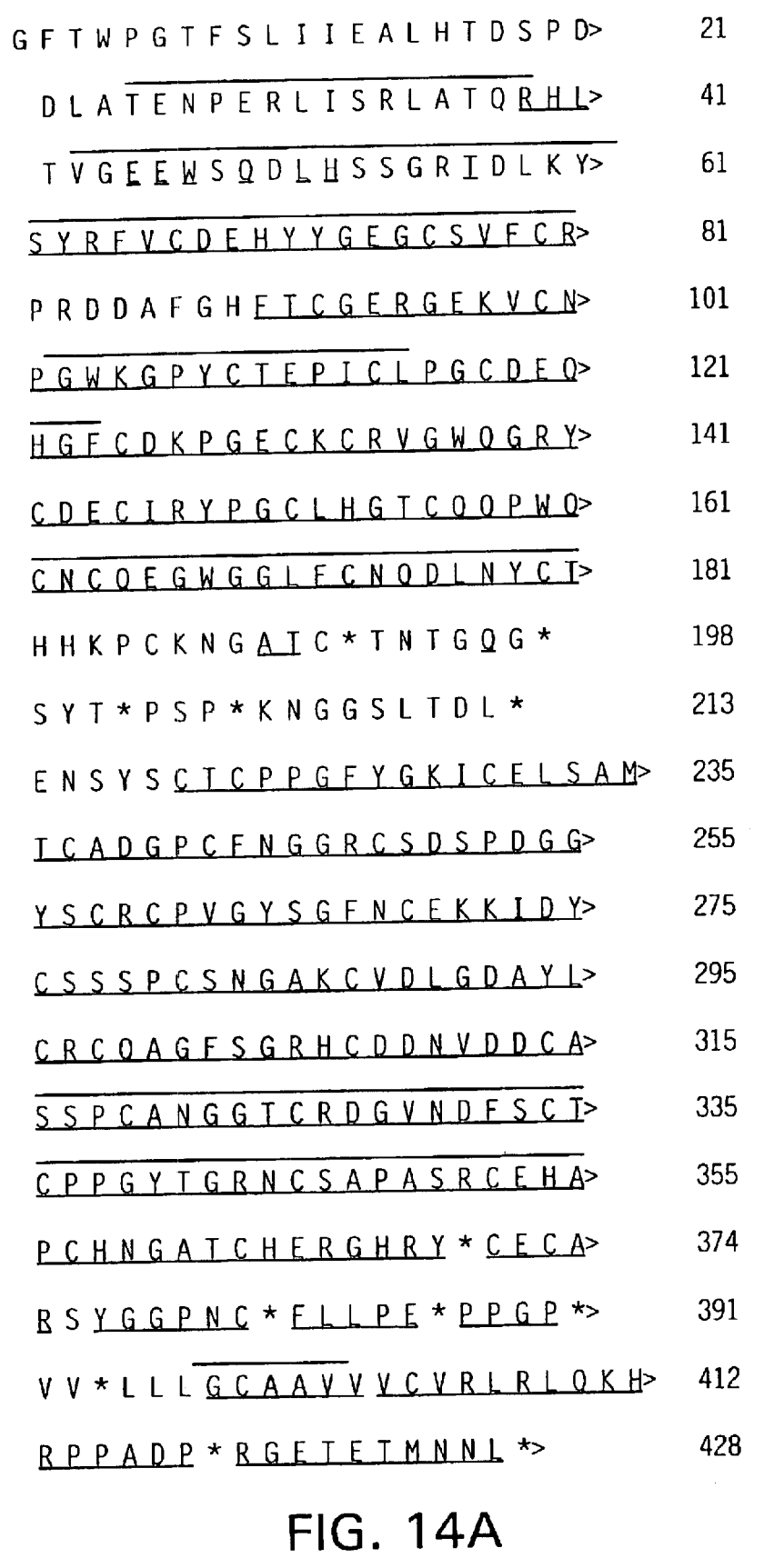
Figure 14B:
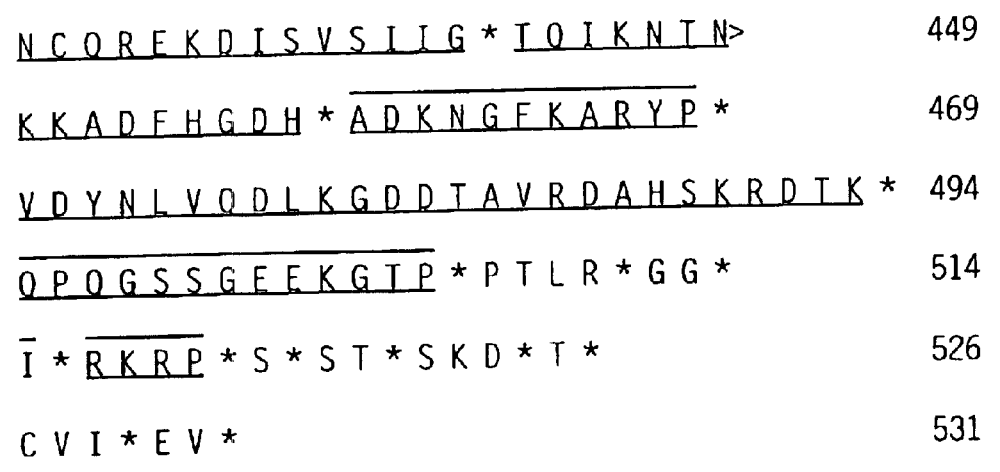

Sequence homology was determined by eye using the mouse Delta-1 amino acid sequence. The sequences with the greatest degree of homology to the mouse amino acid sequence are boxed in FIGS. 12B1–12B6, and represent the predicted amino acid sequence of human Delta-1. The composite resulting amino acid sequence is shown in FIGS. 14A–14B. (In FIGS. 14A–14B, the various uninterrupted portions of the human Delta sequence are assigned respectively, SEQ ID NOS:65–80.) Note that due to sequencing errors, the reading frame with the greatest homology is not the same throughout the sequence and shifts at positions where there are errors in the sequence.

Further, the homology determined by eye to chicken and mouse Delta indicates that the amino acid sequence deduced from the determined human Delta nucleotide sequence contains all but about the N-terminal 100–150 amino acids of human Delta-1.

FIGS. 13A–13G present the nucleotide sequence of mouse Delta-1 (top line) SEQ ID NO:4) and the contig nucleotide sequence of human Delta-1 as depicted in FIGS. 12A1–12A3 and 12B1–12B6 (second line, SEQ ID NO:26) and the nucleotide consensus sequence between mouse and human Delta (third line, SEQ ID NO:24).

Using probes containing the human Delta 5' nucleotide sequences presented in FIGS. 12A1–12A3, cDNA libraries are probed to isolate the 5' end of the human Delta gene. Primary positive clones are obtained and then confirmed as secondary positives. The secondary positives are purified and grown further. The DNA is then isolated and subcloned for sequencing.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various references are cited herein, the disclosures of which are incorporated by reference in their entireties.

What is claimed is:

1. An isolated nucleic acid comprising a nucleotide sequence encoding a vertebrate Delta protein, said vertebrate Delta protein comprising an amino acid sequence selected from the group consisting of the amino acid sequence depicted in SEQ ID NO:2, the amino acid sequence depicted in SEQ ID NO:12, the amino acid sequence depicted in SEQ ID NO:23, the amino acid sequence depicted in SEQ ID NO:65, the amino acid sequence depicted in SEQ ID NO:72 and the amino acid sequence depicted in SEQ ID NO:77.

2. The nucleic acid of claim 1 which is DNA.

3. An isolated nucleic acid comprising a nucleotide sequence complementary to the nucleotide sequence of claim 1.

4. An isolated nucleic acid comprising a nucleotide sequence encoding the amino acid sequence depicted in SEQ ID NO:23, SEQ ID NO:65, SEQ ID NO:72 or SEQ ID NO:77.

5. An isolated nucleic acid comprising a fragment of a vertebrate Delta gene consisting of at least 50 nucleotides, said Delta gene comprising a nucleotide sequence selected from the group consisting of SEQ ID NO:1, SEQ ID NO:3, SEQ ID NO:11, SEQ ID NO:14, SEQ ID NO:24 and SEQ ID NO:26.

6. An isolated nucleic acid comprising a nucleotide sequence encoding a fragment of a human Delta protein which is able to display a functional activity of a Delta protein, said human Delta protein comprising the amino acid sequence depicted in SEQ ID NO:23, SEQ ID NO:65, SEQ ID NO:72 or SEQ ID NO:77, which activity is selected from the group consisting of antigenicity, immunogenicity, binding to a Notch protein and binding to a second Delta protein.

7. An isolated nucleic acid comprising a nucleotide sequence encoding a fragment of a vertebrate Delta protein comprising a domain of the protein selected from the noun consisting of extracellular domain, DSL domain, domain amino terminal to the DSL domain, epidermal growth factor-like repeat domain, transmembrane domain and intracellular domain, said Delta protein comprising an amino acid sequence selected from the group consisting of SEQ ID NO:2, SEQ ID NO:12, SEQ ID NO:23, SEQ ID NO:65, SEQ ID NO:72 and SEQ ID NO:77.

8. An isolated nucleic acid comprising a nucleotide sequence encoding a fragment of a vertebrate Delta protein, which fragment is able to bind a Notch protein, said Delta protein comprising an amino acid sequence selected from the group consisting of SEQ ID NO:2, SEQ ID NO:12, SEQ ID NO:23, SEQ ID NO:65, SEQ ID NO:72 and SEQ ID NO:77.

9. An isolated nucleic acid comprising a nucleotide sequence encoding a protein, said protein comprising amino acid numbers 1–175 of the human Delta sequence depicted in SEQ ID NO:23, or a complement of said nucleotide sequence.

10. An isolated nucleic acid comprising a nucleotide sequence encoding a chimeric protein comprising a fragment of a vertebrate Delta protein consisting of at least 20 amino acids fused via a covalent bond to an amino acid sequence of a second protein, in which the second protein is not a Delta protein, said vertebrate Delta protein comprising an amino acid sequence selected from the group consisting of SEQ ID NO:2, SEQ ID NO:12, SEQ ID NO:23, SEQ ID NO:65, SEQ ID NO:72 and SEQ ID NO:77.

11. A recombinant cell transformed with a recombinant nucleic acid, which nucleic acid encodes a vertebrate Delta protein, said vertebrate Delta protein comprising an amino acid sequence selected from the group consisting of the amino acid sequence depicted in SEQ ID NO:2, the amino acid sequence depicted in SEQ ID NO:12, the amino acid sequence depicted in SEQ ID NO:23, the amino acid sequence depicted in SEQ ID NO:65, the amino acid sequence depicted in SEQ ID NO:72 and the amino acid sequence depicted in SEQ ID NO:77.

12. A recombinant cell transformed with a recombinant nucleic acid encoding a fragment of a vertebrate Delta protein comprising a domain of the protein selected from the group consisting of extracellular domain, DSL domain, domain amino terminal to the DSL domain, epidermal growth factor-like repeat domain, transmembrane domain and intracellular domain, said Delta protein comprising an amino acid sequence selected from the group consisting of SEQ ID NO:2, SEQ ID NO:12, SEQ ID NO:23, SEQ ID NO:65, SEQ ID NO:72 and SEQ ID NO:77.

13. A recombinant cell transformed with a recombinant nucleic acid encoding a protein, said protein comprising amino acid numbers 1–175 of the human Delta sequence depicted in SEQ ID NO:23.

14. A method of producing a vertebrate Delta protein comprising growing a recombinant cell transformed with the nucleic acid of claim 1 such that the encoded vertebrate Delta protein is expressed by the cell, and recovering the expressed Delta protein.

15. A method of producing a vertebrate Delta protein comprising growing a recombinant cell transformed with the nucleic acid of claim 9 such that the encoded Delta protein is expressed by the cell, and recovering the expressed Delta protein.

16. A method of producing a protein comprising a fragment of a vertebrate Delta protein, which method comprises growing a recombinant cell transformed with the nucleic acid of claim 7 such that the encoded protein is expressed by the cell, and recovering the expressed protein.

17. An isolated nucleic acid comprising the nucleotide sequence depicted in SEQ ID NO:26.

18. An isolated nucleic acid comprising a nucleotide sequence complementary to the nucleotide sequence depicted in SEQ ID NO:26.

19. An isolated nucleic acid, which nucleic acid (a) hybridizes under conditions of high stringency to a vertebrate Delta sequence depicted in SEQ ID NO:1, SEQ ID NO:3, SEQ ID NO:11, SEQ ID NO:14, SEQ ID NO:24, SEQ ID NO:26, or a sequence comprising an at least 50 nucleotide portion of said Delta sequence or its complement, said high stringency conditions comprising pretreatment for 8 to 12 hours at 65° C. in a solution containing 6×SSC, 50 mM Tris-HCl (pH 7.5), 1 mM EDTA, 0.02% PVP, 0.02% Ficoll, 0.02% BSA, and 500 µg/ml denatured salmon sperm DNA: hybridization for 48 hours at 65° C. in a solution containing 6×SSC, 50 mM Tris-HCl (pH 7.5), 1 mM EDTA, 0.02% PVP, 0.02% Ficoll, 0.2% BSA, and 100 µg/ml denatured salmon sperm DNA; washing for 1 hour at 37° C. in a solution containing 2×SSC, 0.01% PVP, 0.0 1% Ficoll, and 0.01% SDS and a second washing for 45 minutes at 50° C. in a solution containing 0.1×SSC, and (b) encodes, or is the antisense strand to a nucleic acid which encodes, a protein which is able to be bound by an anti-vertebrate Delta antibody.

20. The nucleic acid of claim 19 which is cDNA.

21. An isolated nucleic acid, which nucleic acid (a) hybridizes under conditions of high stringency to a second nucleic acid consisting of the nucleotide sequence depicted in SEQ ID NO:14, or comprising an at least 50 nucleotide portion of said sequence, said high stringency conditions comprising pretreatment for 8 to 12 hours at 65° C. in a solution containing 6×SSC, 50 mM Tris-HCl (pH 7.5), 1 mM EDTA, 0.02% PVP, 0.02% Ficoll, 0.02% BSA, and 500 µg/ml denatured salmon sperm DNA; hybridization for 48 hours at 65° C. in a solution containing 6×SSC, 50 mM Tris-HCl (pH 7.5), 1 mM EDTA, 0.02% PVP, 0.02% Ficoll, 0.2% BSA, and 100 µg/ml denatured salmon sperm DNA; washing for 1 hour at 37° C. in a solution containing 2×SSC, 0.01% PVP, 0.01% Ficoll, and 0.01% SDS and a second washing for 45 minutes at 50° C. in a solution containing 0.1×SSC, and (b) encodes, or is the antisense strand to a nucleic acid which encodes, a protein which is able to be bound by an anti-vertebrate Delta antibody.

22. An isolated nucleic acid, which nucleic acid hybridizes under conditions of high stringency to a nucleic acid consisting of the consensus nucleotide sequence depicted in SEQ ID NO:24, or comprising an at least 50 nucleotide portion of said sequence, said high stringency conditions comprising pretreatment for 8 to 12 hours at 65° C. in a solution containing 6×SSC, 50 mM Tris-HCl (pH 7.5), 1 mM EDTA, 0.02% PVP, 0.02% Ficoll 0.02% BSA, and 500 µg/ml denatured salmon sperm DNA; hybridization for 48 hours at 65° C. in a solution containing 6×SSC, 50 mM Tris-HCl (pH 7.5), 1 mM EDTA, 0.02% PVP, 0.02% Ficoll, 0.2% BSA, and 100 µg/ml denatured salmon sperm DNA; washing for 1 hour at 37° C. in a solution containing 2×SSC, 0.01% PVP, 0.01% Ficoll, and 0.01% SDS and a second washing for 45 minutes at 50° C. in a solution containing 0.1×SSC, and (b) encodes, or is the antisense strand to a nucleic acid which encodes, a protein which is able to be bound by an anti-vertebrate Delta antibody.

23. An isolated nucleic acid consisting of a vertebrate Delta sequence selected from the group consisting of SEQ ID NO:1, SEQ ID NO:3, SEQ ID NO:11, SEQ ID NO:14, SEQ ID NO:24 and SEQ ID NO:26.

24. The nucleic acid of claim 23, which consists of the nucleotide sequence depicted in SEQ ID NO:24.

25. The nucleic acid of claim 23, which consists of the nucleotide sequence depicted in SEQ ID NO:14.

26. An isolated nucleic acid comprising a vertebrate Delta sequence selected from the group consisting of the mouse Delta sequence of SEQ ID NO:11, the complementary strand to the mouse Delta sequence of SEQ ID NO:11, the chick Delta sequence of SEQ ID NO:1, the complementary strand to the chick Delta sequence of SEQ ID NO:1, the chick Delta sequence of SEQ ID NO:4, the complementary strand to the chick Delta sequence of SEQ ID NO:4, the human Delta sequence of SEQ ID NO:14, the complementary strand to the human Delta sequence of SEQ ID NO:14, the human Delta sequence of SEQ ID NO:26, the complementary strand to the human Delta sequence of SEQ ID NO:26, the human-mouse Delta consensus sequence of SEQ ID NO:24, and the complementary strand to the human-mouse Delta consensus sequence of SEQ ID NO:24.

27. The nucleic acid of claim 26 in which the vertebrate Delta sequence is the human Delta sequence of SEQ ID NO:14.

28. The nucleic acid of claim 26 in which the vertebrate Delta sequence is the complementary strand to the human Delta sequence of SEQ ID NO:14.

29. The nucleic acid of claim 26 in which the vertebrate Delta sequence is the human Delta sequence of SEQ ID NO:26.

30. The nucleic acid of claim 26 in which the vertebrate Delta sequence is the complementary strand to the human Delta sequence of SEQ ID NO:26.

31. The nucleic acid of claim 26 which is an expression vector comprising said Delta sequence operably linked to a non-native promoter.

32. A recombinant cell transformed with a recombinant nucleic acid, which nucleic acid (a) hybridizes under conditions of high stringency to a vertebrate Delta sequence depicted in SEQ ID NO:1, SEQ ID NO:3, SEQ ID NO:11, SEQ ID NO:14, SEQ ID NO:24, SEQ ID NO:26, or a sequence comprising an at least 50 nucleotide portion of said Delta sequence, said high stringency conditions comprising pretreatment for 8 to 12 hours at 65° C. in a solution containing 6×SSC, 50 mM Tris-HCl (pH 7.5), 1 mM EDTA, 0.02% PVP, 0.02% Ficoll, 0.02% BSA, and 500 µg/ml denatured salmon sperm DNA; hybridization for 48 hours at 65° C. in a solution containing 6×SSC, 50 mM Tris-HCl (pH 7.5), 1 mM EDTA, 0.02% PVP, 0.02% Ficoll, 0.2% BSA, and 100 µg/ml denatured salmon sperm DNA; washing for 1 hour at 37° C. in a solution containing 2×SSC, 0.01% PVP, 0.01% Ficoll, and 0.01% SDS and a second washing for 45 minutes at 50° C. in a solution containing 0.1×SSC, and (b) encodes, or is the antisense strand to a nucleic acid which encodes, a protein which is able to be bound by an anti-vertebrate Delta antibody.

33. A method of producing a protein comprising growing the recombinant cell of claim 32 such that the encoded protein is expressed by the cell, and recovering the expressed protein.

34. The recombinant cell of claim 32 in which the recombinant cell encodes a human Delta protein.

35. The recombinant cell of claim 32 in which the anti-vertebrate Delta antibody does not bind to Drosophila Delta protein.

36. The nucleic acid of claim 19 which encodes a human protein.

37. The nucleic acid of claim 19 in which the anti-vertebrate Delta antibody does not bind to Drosophila Delta protein.

38. The nucleic acid of claim 19 in which the high stringency conditions consist of pretreatment for 8 to 12 hours at 65° C. in a solution containing 6×SSC, 50 mM Tris-HCl (pH 7.5), 1 mM EDTA, 0.02% PVP, 0.02% Ficoll, 0.02% BSA, and 500 µg/ml denatured salmon sperm DNA; hybridization for 48 hours at 65° C. in a solution containing 6×SSC, 50 mM Tris-HCl (pH 7.5), 1 mM EDTA, 0.02% PVP, 0.02% Ficoll, 0.2% BSA, and 100 µg/ml denatured salmon sperm DNA; washing for 1 hour at 37° C. in a solution containing 2×SSC, 0.01% PVP, 0.01% Ficoll, and 0.01% SDS and a second washing for 45 minutes at 50° C. in a solution containing 0.1×SSC.

39. An isolated nucleic acid, which nucleic acid (a) hybridizes under conditions of low stringency to a vertebrate Delta sequence depicted in SEQ ID NO:1, SEQ ID NO:3, SEQ ID NO:11, SEQ ID NO:14, SEQ ID NO:24, SEQ ID NO:26, or a sequence comprising an at least 50 nucleotide portion of said Delta sequence, said low stringency conditions comprising pretreatment for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA; hybridization for 18–20 hours at 40° C. in a solution containing 35% formamide, 5×SSC, 50 mM Tris-HCl (pH 7.5), 5 mM EDTA, 0.02% PVP, 0.02% Ficoll, 0.2% BSA, 100 µg/ml denatured salmon sperm DNA, and 10% (wt./vol.) dextran sulfate; washing for 1.5 hours at 55° C. in a solution containing 2×SSC, 25 mM Tris-HCl (pH 7.4), 5 mM EDTA and 0.1% SDS; and a second washing for 1.5 hours at 60° C. in a solution containing 2×SSC, 25 mM Tris-HCl (pH 7.4), 5 mM EDTA and 0.1% SDS, and (b) encodes, or is the antisense strand to a nucleic acid which encodes, a protein which is able to be bound by an anti-vertebrate Delta antibody.

40. The nucleic acid of claim 39 in which the low stringency conditions consist of pretreatment for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA; hybridization for 18–20 hours at 40° C. in a solution containing 35% formamide, 5×SSC, 50 mM Tris-HCl (pH 7.5), 5 mM EDTA, 0.02% PVP, 0.02% Ficoll, 0.2% BSA, 100 µg/ml denatured salmon sperm DNA, and 10% (wt/vol.) dextran sulfate; washing for 1.5 hours at 55° C. in a solution containing 2×SSC, 25 mM Tris-HCl (pH 7.4), 5 mM EDTA and 0.1% SDS; and a second washing for 1.5 hours at 60° C. in a solution containing 2×SSC, 25 mM Tris-HCl (pH 7.4), 5 mM EDTA and 0.1% SDS.

41. The nucleic acid of claim 39 which encodes a human protein.

42. A recombinant cell transformed with a recombinant nucleic acid, which nucleic acid (a) hybridizes under conditions of low stringency to a vertebrate Delta sequence depicted in SEQ ID NO:1, SEQ ID NO:3, SEQ ID NO:11, SEQ ID NO:14, SEQ ID NO:24, SEQ ID NO:26, or a sequence comprising an at least 50 nucleotide portion of said Delta sequence, said low stringency conditions comprising pretreatment for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA; hybridization for 18–20 hours at 40° C. in a solution containing 35% formamide, 5×SSC, 50 mM Tris-HCL (pH 7.5), 5 mM EDTA, 0.02% PVP, 0.02% Ficoll, 0.2% BSA, 100 µg/ml denatured salmon sperm DNA, and 10% (wt/vol.) dextran sulfate; washing for 1.5 hours at 55° C. in a solution containing 2×SSC, 25 mM Tris-HCl (pH 7.4), 5 mM EDTA and 0.1% SDS; and a second washing for 1.5 hours at 60° C. in a solution containing 2×SSC, 25 mM Tris-HCl (pH 7.4), 5 mM EDTA and 0.1% SDS, and (b) encodes, or is the antisense strand to a nucleic acid which encodes, a protein which is able to be bound by an anti-vertebrate Delta antibody.

43. A method of producing a protein comprising growing the recombinant cell of claim 42 such that the encoded protein is expressed by the cell, and recovering the expressed protein.

44. The recombinant cell of claim 42 which encodes a human protein.

45. An isolated nucleic acid comprising a nucleotide sequence encoding a fragment of at least 20 amino acids of a vertebrate Delta protein, said fragment being able to display one or more functional activities of a Delta protein, said vertebrate Delta protein comprising an amino acid sequence selected from the group consisting of the amino acid sequence depicted in SEQ ID NO:2, SEQ ID NO:12, SEQ ID NO:23, SEQ ID NO:65, SEQ ID NO:72 and SEQ ID NO:77.

46. An isolated nucleic acid comprising a fragment of a vertebrate Delta gene consisting of at least 25 nucleotides of a vertebrate Delta nucleotide sequence depicted in SEQ ID NO:1, SEQ ID NO:3, SEQ ID NO:11, SEQ ID NO:14, SEQ ID NO:24, SEQ ID NO:26, or a complement of said nucleotide sequence.

47. The nucleic acid of claim 46 in which the fragment is of the human Delta sequence depicted in SEQ ID NO:14.

48. A recombinant cell transformed with a recombinant nucleic acid comprising at least 25 nucleotides of a vertebrate Delta nucleotide sequence depicted in SEQ ID NO:1, SEQ ID NO:3, SEQ ID NO:11, SEQ ID NO:14, SEQ ID NO:24, SEQ ID NO:26, or a complement of said nucleotide sequence.

49. A method for producing a protein comprising growing the recombinant cell of claim 48 such that the encoded protein is expressed by the cell, and recovering the expressed protein.

50. An isolated nucleic acid comprising a nucleotide sequence encoding a fragment of at least 20 amino acids of a vertebrate Delta protein, said protein comprising a sequence selected from the group consisting of the chick Delta sequence depicted in SEQ ID NO:2, the mouse Delta sequence depicted in SEQ ID NO:12, the human Delta sequence depicted in SEQ ID NO:23, the human Delta sequence depicted in SEQ ID NO:65, the human Delta sequence depicted in SEQ ID NO:72 and the human Delta sequence depicted in SEQ ID NO:77, which fragment (a) is capable of being bound by an anti-vertebrate Delta antibody; and (b) lacks the transmembrane and intracellular domains of the protein.

51. The nucleic acid in which the vertebrate Delta protein has the amino acid sequence depicted in SEQ ID NO:23.

52. The nucleic acid of claim 50 in which the vertebrate Delta protein has the amino acid sequence depicted in SEQ ID NO:65.

53. An isolated nucleic acid comprising a nucleotide sequence encoding a fragment of at least 10 amino acids of a vertebrate Delta protein, said protein comprising a sequence selected from the group consisting of the chick Delta sequence depicted in SEQ ID NO:2, the mouse Delta sequence depicted in SEQ ID NO:12, the human Delta sequence depicted in SEQ ID NO:23, the human Delta sequence depicted in SEQ ID NO:65, the human Delta sequence depicted in SEQ ID NO:72 and the human Delta sequence depicted in SEQ ID NO:77, which fragment (a) is capable of being bound by an anti-vertebrate Delta antibody; and (b) lacks the extracellular domain of the protein.

54. The nucleic acid of claim 53 in which the fragment is of the human Delta sequence depicted in SEQ ID NO:23.

55. The nucleic acid of claim 53 in which the fragment is of the human Delta sequence depicted in SEQ ID NO:65.

56. An isolated nucleic acid comprising a nucleotide sequence encoding a protein comprising a fragment of at least 20 amino acids of a vertebrate Delta protein, said vertebrate Delta protein comprising a sequence selected from the group consisting of the chick Delta sequence depicted in SEQ ID NO:2, the mouse Delta sequence depicted in SEQ ID NO:12, the human Delta sequence depicted in SEQ ID NO:23, the human Delta sequence depicted in SEQ ID NO:65, the human Delta sequence depicted in SEQ ID NO:72 and the human Delta sequence depicted in SEQ ID NO:77, which fragment is able to bind to a Notch protein.

57. An isolated nucleic acid comprising a nucleotide sequence encoding a protein comprising a fragment of at least 20 amino acids of the chick Delta sequence depicted in SEQ ID NO:2, said fragment comprising a domain of the protein selected from the group consisting of the extracellular domain, DSL domain, epidermal growth factor-like repeat domain, cysteine-rich domain, transmembrane domain, and intracellular domain.

58. An isolated nucleic acid comprising a nucleotide sequence encoding a protein comprising a fragment of at least 20 amino acids of the mouse Delta sequence depicted in SEQ ID NO:12, said fragment comprising a domain of the protein selected from the group consisting of the extracellular domain, DSL domain, epidermal growth factor-like repeat domain, cysteine-rich domain, transmembrane domain, and intracellular domain.

59. An isolated nucleic acid which encodes a fragment of a vertebrate Delta protein, which fragment consists of a domain of the protein selected from the group consisting of the extracellular domain, the DSL domain, epidermal growth factor-like repeat domain, transmembrane domain, and intracellular domain, which nucleic acid hybridizes under high stringency conditions to the consensus nucleotide sequence depicted in SEQ ID NO:24 or its complement, which fragment is able to be bound by an anti-vertebrate Delta antibody, said high stringency conditions comprising pretreatment for 8 to 12 hours at 65° C. in a solution containing 6×SSC, 50 mM Tris-HCl (pH 7.5), 1 mM EDTA, 0.02% PVP, 0.02% Ficoll, 0.02% BSA, and 500 µg/ml denatured salmon sperm DNA; hybridization for 48 hours at 65° C. in a solution containing 6×SSC, 50 mM Tris-HCl (pH 7.5), 1 mM EDTA, 0.02% PVP, 0.02% Ficoll, 0.2% BSA, and 100 µg/ml denatured salmon sperm DNA; washing for 1 hour at 37° C. in a solution containing 2×SSC, 0.01% PVP, 0.01% Ficoll, and 0.01% SDS and a second washing for 45 minutes at 50° C. in a solution containing 0.1×SSC.

60. An isolated nucleic acid which encodes a fragment of a vertebrate Delta protein, which fragment consists of a domain of the protein selected from the group consisting of the extracellular domain, the DSL domain, epidermal growth factor-like repeat domain, transmembrane domain, and intracellular domain, which nucleic acid hybridizes under low stringency conditions to the consensus nucleotide sequence depicted in SEQ ID NO:24 or its complement, which fragment is able to be bound by an anti-vertebrate Delta antibody, said low stringency conditions comprising pretreatment for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA; hybridization for 18–20 hours at 40° C. in a solution containing 35% formamide, 5×SSC, 50 mM Tris-HCl (pH 7.5), 5 mM EDTA, 0.02% PVP, 0.02% Ficoll, 0.2% BSA, 100 µg/ml denatured salmon sperm DNA, and 10% (wt./vol.) dextran sulfate; washing for 1.5 hours at 55° C. in a solution containing 2×SSC, 25 mM Tris-HCl (pH 7.4), 5 mM EDTA and 0.1% SDS; and a second washing for 1.5 hours at 60° C. in a solution containing 2×SSC, 25 mM Tris-HCl (pH 7.4), 5 mM EDTA and 0.1% SDS.

61. The nucleic acid of claim 1 which hybridizes under high stringency conditions to a vertebrate Delta nucleotide sequence depicted in SEQ ID NO:1, SEQ ID NO:3, SEQ ID NO:11, SEQ ID NO:14, SEQ ID NO:24 or SEQ ID NO:26, or a complement thereof, said high stringency conditions consisting of pretreatment for 8 to 12 hours at 65° C. in a solution containing 6×SSC, 50 mM Tris-HCL (pH 7.5), 1 mM EDTA, 0.02% PVP, 0.02% Ficoll, 0.02% BSA, and 500 µg/ml denatured salmon sperm DNA; hybridization for 48 hours at 65° C. in a solution containing 6×SSC, 50 mM Tris-HCl (pH 7.5), 1 mM EDTA, 0.02% PVP, 0.02% Ficoll, 0.2% BSA, and 100 µg/ml denatured salmon sperm DNA; washing for 1 hour at 37° C. in a solution containing 2×SSC, 0.01% PVP, 0.01% Ficoll, and 0.01% SDS and a second washing for 45 minutes at 50° C. in a solution containing 0.1×SSC.

62. The nucleic acid of claim which hybridizes under low stringency conditions to a vertebrate Delta nucleotide sequence depicted in SEQ ID NO:1, SEQ ID NO:3, SEQ ID NO:11, SEQ ID NO:14, SEQ ID NO:24 or SEQ ID NO:26, or a complement thereof, said low stringency conditions consisting of pretreatment for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA; hybridization for 18–20 hours at 40° C. in a solution containing 35% formamide, 5×SSC, 50 mM Tris-HCl (pH 7.5), 5 mM EDTA, 0.02% PVP, 0.02% Ficoll, 0.2% BSA, 100 µg/ml denatured salmon sperm DNA, and 10% (wt./vol.) dextran sulfate; washing for 1.5 hours at 55° C. in a solution containing 2×SSC, 25 mM Tris-HCl (pH 7.4), 5 mM EDTA and 0.1% SDS; and a second washing for 1.5 hours at 60° C. in a solution containing 2×SSC, 25 mM Tris-HCl (pH 7.4), 5 mM EDTA and 0.1% SDS.

63. An isolated nucleic acid comprising a nucleotide sequence encoding a protein, said protein comprising amino acid numbers 1–192 of the human Delta sequence depicted in SEQ ID NO:65, or the complement of said nucleotide sequence.

64. A recombinant cell transformed with a recombinant nucleic acid encoding a protein, said protein comprising amino acid numbers 1–192 of the human Delta sequence depicted in SEQ ID NO:65.

65. A method of producing a vertebrate Delta protein comprising growing the recombinant cell of claim 64 such that the encoded protein is expressed by the cell, and recovering the expressed protein.

66. The nucleic acid of claim 1 which is an expression vector comprising said nucleotide sequence operably linked to a non-native promoter.

67. The nucleic acid of claim 63 which is an expression vector comprising said nucleotide sequence operably linked to a non-native promoter.

* * * * *

UNITED STATES PATENT AND TRADEMARK OFFICE
CERTIFICATE OF CORRECTION

PATENT NO.   : 6,783,956 B2
DATED        : August 31, 2004
INVENTOR(S)  : Ish-Horowicz et al.

It is certified that error appears in the above-identified patent and that said Letters Patent is hereby corrected as shown below:

<u>Column 138,</u>
Line 57, after "claim" and before "which", insert -- 1 --.

Signed and Sealed this

Twenty-second Day of February, 2005

JON W. DUDAS
*Director of the United States Patent and Trademark Office*

SEQUENCE LISTING (1) GENERAL INFORMATION:

(iii) NUMBER OF SEQUENCES: 94

(2) INFORMATION FOR SEQ ID NO: 1:

(i) SEQUENCE CHARACTERISTICS:
      (A) LENGTH: 2508 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: Coding Sequence
      (B) LOCATION: 277...2460
      (D) OTHER INFORMATION:

(xi) SEQUENCE DESCRIPTION: SEQ ID NO: 1:

```
GAATTCGGCA CGAGGTTTTT TTTTTTTTTT TTCCCCTCTT TTCTTTCTTT TCCTTTTGCC      60

ATCCGAAAGA GCTGTCAGCC GCCGCCGGGC TGCACCTAAA GGCGTCGGTA GGGGGATAAC     120

AGTCAGAGAC CCTCCTGAAA GCAGGAGACG GGACGGTACC CCTCCGGCTC TGCGGGGCGG    180

CTGCGGCCCC TCCGTTCTTT CCCCCTCCCC GAGAGACACT CTTCCTTTCC CCCCACGAAG    240

ACACAGGGGC AGGAACGCGA GCGCTGCCCC TCCGCC ATG GGA GGC CGC TTC CTG      294
                                         Met Gly Gly Arg Phe Leu
                                           1               5
```

| | | | | | | | | | | | | | | | |
|---|---|---|---|---|---|---|---|---|---|---|---|---|---|---|---|
| CTG | ACG | CTC | GCC | CTC | CTC | TCG | GCG | CTG | CTG | TGC | CGC | TGC | CAG | GTT | GAC | 342 |
| Leu | Thr | Leu | Ala | Leu | Leu | Ser | Ala | Leu | Leu | Cys | Arg | Cys | Gln | Val | Asp |
| | | 10 | | | | 15 | | | | 20 | | | | | |

```
GGC TCC GGG GTG TTC GAG CTG AAG CTG CAG GAG TTT GTC AAC AAG AAG      390
Gly Ser Gly Val Phe Glu Leu Lys Leu Gln Glu Phe Val Asn Lys Lys
        25                  30                  35

GGG CTG CTC AGC AAC CGC AAC TGC TGC CGG GGG GGC GGC CCC GGA GGC      438
Gly Leu Leu Ser Asn Arg Asn Cys Cys Arg Gly Gly Gly Pro Gly Gly
    40                  45                  50

GCC GGG CAG CAG CAG TGC GAC TGC AAG ACC TTC TTC CGC GTC TGC CTG      486
Ala Gly Gln Gln Gln Cys Asp Cys Lys Thr Phe Phe Arg Val Cys Leu
55                  60                  65                  70

AAG CAC TAC CAG GCC AGC GTC TCC CCC GAG CCG CCC TGC ACC TAC GGC      534
Lys His Tyr Gln Ala Ser Val Ser Pro Glu Pro Pro Cys Thr Tyr Gly
                75                  80                  85

AGC GCC ATC ACC CCC GTC CTC GGC GCC AAC TCC TTC AGC GTC CCC GAC      582
Ser Ala Ile Thr Pro Val Leu Gly Ala Asn Ser Phe Ser Val Pro Asp
            90                  95                 100

GGC GCG GGC GGC GCC GAC CCC GCC TTC AGC AAC CCC ATC CGC TTC CCC      630
Gly Ala Gly Gly Ala Asp Pro Ala Phe Ser Asn Pro Ile Arg Phe Pro
        105                 110                 115

TTC GGC TTC ACC TGG CCC GGC ACC TTC TCG CTC ATC ATC GAG GCT CTG      678
Phe Gly Phe Thr Trp Pro Gly Thr Phe Ser Leu Ile Ile Glu Ala Leu
    120                 125                 130

CAC ACC GAC TCC CCC GAC GAC CTC ACC ACA GAA AAC CCC GAG CGC CTC      726
His Thr Asp Ser Pro Asp Asp Leu Thr Thr Glu Asn Pro Glu Arg Leu
135                 140                 145                 150

ATC AGC CGC CTG GCC ACC CAG AGG CAC CTG GCG GTG GGC GAG GAG TGG      774
Ile Ser Arg Leu Ala Thr Gln Arg His Leu Ala Val Gly Glu Glu Trp
                155                 160                 165

TCC CAG GAC CTG CAC AGC AGC GGC CGC ACC GAC CTC AAG TAC TCC TAT      822
Ser Gln Asp Leu His Ser Ser Gly Arg Thr Asp Leu Lys Tyr Ser Tyr
            170                 175                 180

CGC TTT GTG TGT GAT GAG CAC TAC TAC GGG GAA GGC TGC TCT GTC TTC      870
Arg Phe Val Cys Asp Glu His Tyr Tyr Gly Glu Gly Cys Ser Val Phe
        185                 190                 195

TGC CGG CCC CGT GAC GAC CGC TTC GGT CAC TTC ACC TGT GGA GAG CGT      918
Cys Arg Pro Arg Asp Asp Arg Phe Gly His Phe Thr Cys Gly Glu Arg
    200                 205                 210

GGC GAG AAG GTC TGC AAC CCA GGC TGG AAG GGC CAG TAC TGC ACT GAG      966
Gly Glu Lys Val Cys Asn Pro Gly Trp Lys Gly Gln Tyr Cys Thr Glu
215                 220                 225                 230

CCG ATT TGC TTG CCT GGG TGT GAC GAG CAG CAC GGC TTC TGC GAC AA      1014
Pro Ile Cys Leu Pro Gly Cys Asp Glu Gln His Gly Phe Cys Asp Lys
                235                 240                 245

CCT GGG GAA TGC AAG TGC AGA GTG GGT TGG CAG GGG CGG TAC TGT GA      1062
Pro Gly Glu Cys Lys Cys Arg Val Gly Trp Gln Gly Arg Tyr Cys Asp
            250                 255                 260

GAG TGC ATC CGA TAC CCA GGC TGC CTG CAC GGT ACC TGT CAG CAG CC      1110
```

-continued

| | | |
|---|---|---|
| Glu Cys Ile Arg Tyr Pro Gly Cys Leu His Gly Thr Cys Gln Gln Pro<br>265 270 275 | | |
| TGG CAG TGC AAC TGC CAG GAA GGC TGG GGC GGC CTT TTC TGC AAC CA<br>Trp Gln Cys Asn Cys Gln Glu Gly Trp Gly Gly Leu Phe Cys Asn Gln<br>280 285 290 | 1158 | |
| GAC CTG AAC TAC TGC ACT CAC CAC AAG CCA TGC AAG AAT GGT GCC AC<br>Asp Leu Asn Tyr Cys Thr His His Lys Pro Cys Lys Asn Gly Ala Thr<br>295 300 305 310 | 1206 | |
| TGC ACC AAC ACC GGT CAG GGG AGC TAC ACT TGT TCT TGC CGA CCT GG<br>Cys Thr Asn Thr Gly Gln Gly Ser Tyr Thr Cys Ser Cys Arg Pro Gly<br>315 320 325 | 1254 | |
| TAC ACA GGC TCC AGC TGC GAG ATT GAA ATC AAC GAA TGT GAT GCC AA<br>Tyr Thr Gly Ser Ser Cys Glu Ile Glu Ile Asn Glu Cys Asp Ala Asn<br>330 335 340 | 1302 | |
| CCT TGC AAG AAT GGT GGA AGC TGC ACG GAT CTC GAG AAC AGC TAT TC<br>Pro Cys Lys Asn Gly Gly Ser Cys Thr Asp Leu Glu Asn Ser Tyr Ser<br>345 350 355 | 1350 | |
| TGT ACC TGC CCC CCA GGC TTC TAT GGT AAA AAC TGT GAG CTG AGT GC<br>Cys Thr Cys Pro Pro Gly Phe Tyr Gly Lys Asn Cys Glu Leu Ser Ala<br>360 365 370 | 1398 | |
| ATG ACT TGT GCT GAT GGA CCG TGC TTC AAT GGA GGG CGA TGC ACT GA<br>Met Thr Cys Ala Asp Gly Pro Cys Phe Asn Gly Gly Arg Cys Thr Asp<br>375 380 385 390 | 1446 | |
| AAC CCT GAT GGT GGA TAC AGC TGC CGC TGC CCA CTG GGT TAT TCT GG<br>Asn Pro Asp Gly Gly Tyr Ser Cys Arg Cys Pro Leu Gly Tyr Ser Gly<br>395 400 405 | 1494 | |
| TTC AAC TGT GAA AAG AAA ATC GAT TAC TGC AGT TCC AGC CCT TGT GC<br>Phe Asn Cys Glu Lys Lys Ile Asp Tyr Cys Ser Ser Ser Pro Cys Ala<br>410 415 420 | 1542 | |
| AAT GGA GCC CAG TGC GTT GAC CTG GGG AAC TCC TAC ATA TGC CAG TG<br>Asn Gly Ala Gln Cys Val Asp Leu Gly Asn Ser Tyr Ile Cys Gln Cys<br>425 430 435 | 1590 | |
| CAG GCT GGC TTC ACT GGC AGG CAC TGT GAC GAC AAC GTG GAC GAT TG<br>Gln Ala Gly Phe Thr Gly Arg His Cys Asp Asp Asn Val Asp Asp Cys<br>440 445 450 | 1638 | |
| GCC TCC TTC CCC TGC GTC AAT GGA GGG ACC TGT CAG GAT GGG GTC AA<br>Ala Ser Phe Pro Cys Val Asn Gly Gly Thr Cys Gln Asp Gly Val Asn<br>455 460 465 470 | 1686 | |
| GAC TAC TCC TGC ACC TGC CCC CCG GGA TAC AAC GGG AAG AAC TGC AG<br>Asp Tyr Ser Cys Thr Cys Pro Pro Gly Tyr Asn Gly Lys Asn Cys Ser<br>475 480 485 | 1734 | |
| ACG CCG GTG AGC AGA TGC GAG CAC AAC CCC TGC CAC AAT GGG GCC AC<br>Thr Pro Val Ser Arg Cys Glu His Asn Pro Cys His Asn Gly Ala Thr<br>490 495 500 | 1782 | |
| TGC CAC GAG AGA AGC AAC CGC TAC GTG TGC GAG TGC GCT CGG GGC TA<br>Cys His Glu Arg Ser Asn Arg Tyr Val Cys Glu Cys Ala Arg Gly Tyr<br>505 510 515 | 1830 | |
| GGC GGC CTC AAC TGC CAG TTC CTG CTC CCC GAG CCA CCT CAG GGG CC<br>Gly Gly Leu Asn Cys Gln Phe Leu Leu Pro Glu Pro Pro Gln Gly Pro<br>520 525 530 | 1878 | |
| GTC ATC GTT GAC TTC ACC GAG AAG TAC ACA GAG GGC CAG AAC AGC CA<br>Val Ile Val Asp Phe Thr Glu Lys Tyr Thr Glu Gly Gln Asn Ser Gln<br>535 540 545 550 | 1926 | |
| TTT CCC TGG ATC GCA GTG TGC GCC GGG ATT ATT CTG GTC CTC ATG CT<br>Phe Pro Trp Ile Ala Val Cys Ala Gly Ile Ile Leu Val Leu Met Leu<br>555 560 565 | 1974 | |
| CTG CTG GGT TGC GCC GCC ATC GTC GTC TGC GTC AGG CTG AAG GTG CA<br>Leu Leu Gly Cys Ala Ala Ile Val Val Cys Val Arg Leu Lys Val Gln<br>570 575 580 | 2022 | |

-continued

```
AAG AGG CAC CAC CAG CCC GAG GCC TGC AGG AGT GAA ACG GAG ACC AT            2070
Lys Arg His His Gln Pro Glu Ala Cys Arg Ser Glu Thr Glu Thr Met
            585                 590                 595

AAC AAC CTG GCG AAC TGC CAG CGC GAG AAG GAC ATC TCC ATC AGC GT            2118
Asn Asn Leu Ala Asn Cys Gln Arg Glu Lys Asp Ile Ser Ile Ser Val
600                 605                 610

ATC GGT GCC ACT CAG ATT AAA AAC ACA AAT AAG AAA GTA GAC TTT CA            2166
Ile Gly Ala Thr Gln Ile Lys Asn Thr Asn Lys Lys Val Asp Phe His
615                 620                 625                 630

AGC GAT AAC TCC GAT AAA AAC GGC TAC AAA GTT AGA TAC CCA TCA GT            2214
Ser Asp Asn Ser Asp Lys Asn Gly Tyr Lys Val Arg Tyr Pro Ser Val
            635                 640                 645

GAT TAC AAT TTG GTG CAT GAA CTC AAG AAT GAG GAC TCT GTG AAA GA            2262
Asp Tyr Asn Leu Val His Glu Leu Lys Asn Glu Asp Ser Val Lys Glu
            650                 655                 660

GAG CAT GGC AAA TGC GAA GCC AAG TGT GAA ACG TAT GAT TCA GAG GC            2310
Glu His Gly Lys Cys Glu Ala Lys Cys Glu Thr Tyr Asp Ser Glu Ala
            665                 670                 675

GAA GAG AAA AGC GCA GTA CAG CTA AAA AGT AGT GAC ACT TCT GAA AG            2358
Glu Glu Lys Ser Ala Val Gln Leu Lys Ser Ser Asp Thr Ser Glu Arg
680                 685                 690

AAA CGG CCA GAT TCA GTA TAT TCC ACT TCA AAG GAC ACA AAG TAC CA            2406
Lys Arg Pro Asp Ser Val Tyr Ser Thr Ser Lys Asp Thr Lys Tyr Gln
695                 700                 705                 710

TCG GTG TAC GTC ATA TCA GAA GAG AAA GAT GAG TGC ATC ATA GCA AC            2454
Ser Val Tyr Val Ile Ser Glu Glu Lys Asp Glu Cys Ile Ile Ala Thr
            715                 720                 725

GAG GTG TAAAACAGAC GTGACGTGGC AAAGCTTATC GATACCGTCA TCAAGCTT              2508
Glu Val (2) INFORMATION FOR SEQ ID NO: 2:

(i) SEQUENCE CHARACTERISTICS:
        (A) LENGTH: 728 amino acids
        (B) TYPE: amino acid
        (C) STRANDEDNESS: <Unknown>
        (D) TOPOLOGY: unknown (ii) MOLECULE TYPE: protein (xi) SEQUENCE DESCRIPTION: SEQ ID NO: 2:

Met Gly Gly Arg Phe Leu Leu Thr Leu Ala Leu Leu Ser Ala Leu Leu
 1               5                  10                  15

Cys Arg Cys Gln Val Asp Gly Ser Gly Val Phe Glu Leu Lys Leu Gln
            20                  25                  30

Glu Phe Val Asn Lys Lys Gly Leu Leu Ser Asn Arg Asn Cys Cys Arg
        35                  40                  45

Gly Gly Gly Pro Gly Gly Ala Gly Gln Gln Gln Cys Asp Cys Lys Thr
    50                  55                  60

Phe Phe Arg Val Cys Leu Lys His Tyr Gln Ala Ser Val Ser Pro Glu
65                  70                  75                  80

Pro Pro Cys Thr Tyr Gly Ser Ala Ile Thr Pro Val Leu Gly Ala Asn
            85                  90                  95

Ser Phe Ser Val Pro Asp Gly Ala Gly Gly Ala Asp Pro Ala Phe Ser
            100                 105                 110

Asn Pro Ile Arg Phe Pro Phe Gly Phe Thr Trp Pro Gly Thr Phe Ser
            115                 120                 125

Leu Ile Ile Glu Ala Leu His Thr Asp Ser Pro Asp Asp Leu Thr Thr
    130                 135                 140
```

-continued

```
Glu Asn Pro Glu Arg Leu Ile Ser Arg Leu Ala Thr Gln Arg His Leu
145                 150                 155                 160

Ala Val Gly Glu Glu Trp Ser Gln Asp Leu His Ser Ser Gly Arg Thr
            165                 170                 175

Asp Leu Lys Tyr Ser Tyr Arg Phe Val Cys Asp Glu His Tyr Tyr Gly
        180                 185                 190

Glu Gly Cys Ser Val Phe Cys Arg Pro Arg Asp Asp Arg Phe Gly His
            195                 200                 205

Phe Thr Cys Gly Glu Arg Gly Glu Lys Val Cys Asn Pro Gly Trp Lys
    210                 215                 220

Gly Gln Tyr Cys Thr Glu Pro Ile Cys Leu Pro Gly Cys Asp Glu Gln
225                 230                 235                 240

His Gly Phe Cys Asp Lys Pro Gly Glu Cys Lys Cys Arg Val Gly Trp
            245                 250                 255

Gln Gly Arg Tyr Cys Asp Glu Cys Ile Arg Tyr Pro Gly Cys Leu His
        260                 265                 270

Gly Thr Cys Gln Gln Pro Trp Gln Cys Asn Cys Gln Glu Gly Trp Gly
            275                 280                 285

Gly Leu Phe Cys Asn Gln Asp Leu Asn Tyr Cys Thr His His Lys Pro
290                 295                 300

Cys Lys Asn Gly Ala Thr Cys Thr Asn Thr Gly Gln Gly Ser Tyr Thr
305                 310                 315                 320

Cys Ser Cys Arg Pro Gly Tyr Thr Gly Ser Ser Cys Glu Ile Glu Ile
            325                 330                 335

Asn Glu Cys Asp Ala Asn Pro Cys Lys Asn Gly Gly Ser Cys Thr Asp
        340                 345                 350

Leu Glu Asn Ser Tyr Ser Cys Thr Cys Pro Pro Gly Phe Tyr Gly Lys
            355                 360                 365

Asn Cys Glu Leu Ser Ala Met Thr Cys Ala Asp Gly Pro Cys Phe Asn
    370                 375                 380

Gly Gly Arg Cys Thr Asp Asn Pro Asp Gly Gly Tyr Ser Cys Arg Cys
385                 390                 395                 400

Pro Leu Gly Tyr Ser Gly Phe Asn Cys Glu Lys Lys Ile Asp Tyr Cys
            405                 410                 415

Ser Ser Ser Pro Cys Ala Asn Gly Ala Gln Cys Val Asp Leu Gly Asn
        420                 425                 430

Ser Tyr Ile Cys Gln Cys Gln Ala Gly Phe Thr Gly Arg His Cys Asp
        435                 440                 445

Asp Asn Val Asp Asp Cys Ala Ser Phe Pro Cys Val Asn Gly Gly Thr
450                 455                 460

Cys Gln Asp Gly Val Asn Asp Tyr Ser Cys Thr Cys Pro Pro Gly Tyr
465                 470                 475                 480

Asn Gly Lys Asn Cys Ser Thr Pro Val Ser Arg Cys Glu His Asn Pro
            485                 490                 495

Cys His Asn Gly Ala Thr Cys His Glu Arg Ser Asn Arg Tyr Val Cys
        500                 505                 510

Glu Cys Ala Arg Gly Tyr Gly Gly Leu Asn Cys Gln Phe Leu Leu Pro
    515                 520                 525

Glu Pro Pro Gln Gly Pro Val Ile Val Asp Phe Thr Glu Lys Tyr Thr
530                 535                 540

Glu Gly Gln Asn Ser Gln Phe Pro Trp Ile Ala Val Cys Ala Gly Ile
545                 550                 555                 560

Ile Leu Val Leu Met Leu Leu Leu Gly Cys Ala Ala Ile Val Val Cys
```

-continued

```
                565                 570                 575
Val Arg Leu Lys Val Gln Lys Arg His His Gln Pro Glu Ala Cys Arg
            580                 585                 590

Ser Glu Thr Glu Thr Met Asn Asn Leu Ala Asn Cys Gln Arg Glu Lys
        595                 600                 605

Asp Ile Ser Ile Ser Val Ile Gly Ala Thr Gln Ile Lys Asn Thr Asn
    610                 615                 620

Lys Lys Val Asp Phe His Ser Asp Asn Ser Asp Lys Asn Gly Tyr Lys
625                 630                 635                 640

Val Arg Tyr Pro Ser Val Asp Tyr Asn Leu Val His Glu Leu Lys Asn
                645                 650                 655

Glu Asp Ser Val Lys Glu His Gly Lys Cys Glu Ala Lys Cys Glu
            660                 665                 670

Thr Tyr Asp Ser Glu Ala Glu Lys Ser Ala Val Gln Leu Lys Ser
        675                 680                 685

Ser Asp Thr Ser Glu Arg Lys Arg Pro Asp Ser Val Tyr Ser Thr Ser
    690                 695                 700

Lys Asp Thr Lys Tyr Gln Ser Val Tyr Val Ile Ser Glu Glu Lys Asp
705                 710                 715                 720

Glu Cys Ile Ile Ala Thr Glu Val
                725
```

(2) INFORMATION FOR SEQ ID NO: 3:

(i) SEQUENCE CHARACTERISTICS:
      (A) LENGTH: 2883 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 3:

```
GAATTCGGCA CGAGGTTTTT TTTTTTTTTT TTCCCCTCTT TTCTTTCTTT TCCTTTTGCC    60
ATCCGAAAGA GCTGTCAGCC GCCGCCGGGC TGCACCTAAA GGCGTCGGTA GGGGGATAAC   120
AGTCAGAGAC CCTCCTGAAA GCAGGAGACG GGACGGTACC CCTCCGGCTC TGCGGGGCGG   180
CTGCGGCCCC TCCGTTCTTT CCCCCTCCCC GAGAGACACT CTTCCTTTCC CCCCACGAAG   240
ACACAGGGGC AGGAACGCGA GCGCTGCCCC TCCGCCATGG GAGGCCGCTT CCTGCTGACG   300
CTCGCCCTCC TCTCGGCGCT GCTGTGCCGC TGCCAGGTTG ACGGCTCCGG GGTGTTCGAG   360
CTGAAGCTGC AGGAGTTTGT CAACAAGAAG GGGCTGCTCA GCAACCGCAA CTGCTGCCGG   420
GGGGGCGGCC CCGGAGGCGC CGGGCAGCAG CAGTGCGACT GCAAGACCTT CTTCCGCGTC   480
TGCCTGAAGC ACTACCAGGC CAGCGTCTCC CCCGAGCCGC CCTGCACCTA CGGCAGCGCC   540
ATCACCCCCG TCCTCGGCGC CAACTCCTTC AGCGTCCCCG ACGGCGCGGG CGGCGCCGAC   600
CCCGCCTTCA GCAACCCCAT CCGCTTCCCC TTCGGCTTCA CCTGGCCCGG CACCTTCTAC   660
CTCATCATCG AGGCTCTGCA CACCGACTCC CCCGACGACC TCACCACAGA AAACCCCGAG   720
CGCCTCATCA GCCGCCTGGC CACCCAGAGG CACCTGGCGG TGGGCGAGGA GTGGTCCCAG   780
GACCTGCACA GCAGCGGCCG CACCGACCTC AAGTACTCCT ATCGCTTTGT GTGTGATGAG   840
CACTACTACG GGGAAGGCTG CTCTGTCTTC TGCCGGCCCC GTGACGACCG CTTCGGTCAC   900
TTCACCTGTG GAGAGCGTGG CGAGAAGGTC TGCAACCCAG GCTGGAAGGG CCAGTACTGC   960
ACTGAGCCGA TTTGCTTGCC TGGGTGTGAC GAGCAGCACG GCTTCTGCGA CAAACCTGGG  1020
```

-continued

```
GAATGCAAGT GCAGAGTGGG TTGGCAGGGG CGGTACTGTG ACGAGTGCAT CCGATACCCA    1080

GGCTGCCTGC ACGGTACCTG TCAGCAGCCA TGGCAGTGCA ACTGCCAGGA AGGCTGGGGC    1140

GGCCTTTTCT GCAACCAGGA CCTGAACTAC TGCACTCACC ACAAGCCATG CAAGAATGGT    1200

GCCACATGCA CCAACACCGG TCAGGGGAGC TACACTTGTT CTTGCCGACC TGGGTACACA    1260

GGCTCCAGCT GCGAGATTGA AATCAACGAA TGTGATGCCA ACCCTTGCAA GAATGGTGGA    1320

AGCTGCACGG ATCTCGAGAA CAGCTATTCC TGTACCTGCC CCCCAGGCTT CTATGGTAAA    1380

AACTGTGAGC TGAGTGCAAT GACTTGTGCT GATGGACCGT GCTTCAATGG AGGGCGATGC    1440

ACTGACAACC CTGATGGTGG ATACAGCTGC CGCTGCCCAC TGGGTTATTC TGGGTTCAAC    1500

TGTGAAAAGA AAATCGATTA CTGCAGTTCC AGCCCTTGTG CTAATGGAGC CCAGTGCGTT    1560

GACCTGGGGA ACTCCTACAT ATGCCAGTGC CAGGCTGGCT TCACTGGCAG GCACTGTGAC    1620

GACAACGTGG ACGATTGCGC CTCCTTCCCC TGCGTCAATG GAGGGACCTG TCAGGATGGG    1680

GTCAACGACT ACTCCTGCAC CTGCCCCCCG GGATACAACG GAAGAACTG CAGCACGCCG    1740

GTGAGCAGAT GCGAGCACAA CCCCTGCCAC AATGGGGCCA CCTGCCACGA GAGAAGCAAC    1800

CGCTACGTGT GCGAGTGCGC TCGGGGCTAC GGCGGCCTCA ACTGCCAGTT CCTGCTCCCC    1860

GAGCCACCTC AGGGGCCGGT CATCGTTGAC TTCACCGAGA AGTACACAGA GGGCCAGAAC    1920

AGCCAGTTTC CCTGGATCGC AGTGTGCGCC GGGATTATTC TGGTCCTCAT GCTGCTGCTG    1980

GGTTGCGCCG CCATCGTCGT CTGCGTCAGG CTGAAGGTGC AGAAGAGGCA CCACCAGCCC    2040

GAGGCCTGCA GGAGTGAAAC GGAGACCATG AACAACCTGG CGAACTGCCA GCGCGAGAAG    2100

GACATCTCCA TCAGCGTCAT CGGTGCCACT CAGATTAAAA ACACAAATAA GAAAGTAGAC    2160

TTTCACAGCG ATAACTCCGA TAAAAACGGC TACAAAGTTA GATACCCATC AGTGGATTAC    2220

AATTTGGTGC ATGAACTCAA GAATGAGGAC TCTGTGAAAG AGGAGCATGG CAAATGCGAA    2280

GCCAAGTGTG AAACGTATGA TTCAGAGGCA GAAGAGAAAA GCGCAGTACA GCTAAAAAGT    2340

AGTGACACTT CTGAAAGAAA ACGGCCAGAT TCAGTATATT CCACTTCAAA GGACACAAAG    2400

TACCAGTCGG TGTACGTCAT ATCAGAAGAG AAAGATGAGT GCATCATAGC AACTGAGGTT    2460

AGTATCCCAC CTGGCAGTCG GACAAGTCTT GGTGTGTGAT TCCCATCCAG CGCAGGTCAG    2520

GGCGGCCAAA CCATTCTACC TGCTGCCACA GTCATCTGTA CCCAATGAAA ACTGGCCACC    2580

TTCAGTCTGT GGCACTGCAG ACGTTGAAAA AACTTGTTGT GGATTAACAT AAGCTCCAGT    2640

GGGGGTTACA GGGACAGCAA TTTTTGCAGG CAAGGGTATA ACTGTAGTGC AGTTGTAGCT    2700

TACTAACCCT ACTGACTCAT TCTTTCGTGT GCTTCCTGCA GAGCCTGTTT TTGCTTGGCA    2760

TTGAGGTGAA GTCCTGACCC TCTGCATCCT CATAGTCCTC TGCTTTCTTT TTATTAACCT    2820

CTTCTGGTCT CTGCTTGTCT TTTCTCTCAA CAGGTGTAAA ACAGACGTGA CGTGGCAAAG    2880

CTT                                                                 2883
```

(2) INFORMATION FOR SEQ ID NO: 4:
    (i) SEQUENCE CHARACTERISTICS:
        (A) LENGTH: 2857 base pairs
        (B) TYPE: nucleic acid
        (C) STRANDEDNESS: single
        (D) TOPOLOGY: linear
    (ii) MOLECULE TYPE: cDNA
    (xi) SEQUENCE DESCRIPTION: SEQ ID NO: 4:

```
GTCCAGCGGT ACCATGGGCC GTCGGAGCGC GCTACCCCTT GCCGTGGTCT CTGCCCTGCT      60
GTGCCAGGTC TGGAGCTCCG GCGTATTTGA GCTGAAGCTG CAGGAGTTCG TCAACAAGAA     120

GGGGCTGCTG GGAACCGCA ACTGCTGCCG CGGGGGCTCT GGCCCGCCTT GCGCCTGCAG      180

GACCTTCTTT CGCGTATGCC TCAACCACTA CCAGGCCAGC GTGTCACCGG AGCCACCCTG     240
```

-continued

| | |
|---|---|
| CACCTACGGC AGTGCTGTCA CGCCAGTGCT GGGTCTCGAC TCCTTCAGCC TGCCTGATGG | 300 |
| CGCAGGCATC GACCCCGCCT TCAGCAACCC ATCCGATTCC CCTTCCGGCT TCACCTGGCC | 360 |
| AGGTACCTTC TCTCTGATCA TTGAAGCCCT CCATACAGAC TCTCCCGATG ACCTCGCAAC | 420 |
| AGAAAACCCA GAAAGACTCA TCAGCCGCCT GACCACACAG AGGCACCTCA CTGTGGGACG | 480 |
| AATGGTCTCA GGACCTTCAC AGTAGCGGCC GCACAGACCT CCGGTACTCT TACCGGTTTG | 540 |
| TGTGTGACGA GCACTACTAC GGAGAAGGTT GCTCTGTGTT CTGCCGACCT CGGGATGACG | 600 |
| CCTTTGGCCA CTTCACCTGC GGGGACAGAG GGGAGAAGAT GTGCGACCCT GGCTGGAAAG | 660 |
| GCCAGTACTG CACTGACCCA ATCTGTCTGC AGGGTGTGA TGACCAACAT GGATACTGTG | 720 |
| ACAAACCAGG GGAGTGCAAG TGCAGAGTTG GCTGGCAGGG CCGCTACTGC GATGAGTGCA | 780 |
| TCCGATACCC AGGTTGTCTC CATGGCACCT GCCAGCAACC CTGGCAGTGT AACTGCCAGG | 840 |
| AAGGCTGGGG GGGCCTTTTC TGCAACCAAG ACCTGAACTA CTGTACTCAC CATAAGCCGT | 900 |
| GCAGGAATGG AGCCACCTGC ACCAACACGG GCCAGGGGAG CTACACATGT TCCTGCCGAC | 960 |
| TGGGGTATAC AGGTGCCAAC TGTGAGCTGG AAGTAGATGA GTGTGCTCCT AGCCCCTGCA | 1020 |
| AGAACGGAGC GAGCTGCACG GACCTTGAGG ACAGCTTCTC TTGCACCTGC CCTCCCGGCT | 1080 |
| TCTATGGCAA GGTCTGTGAG CTTGAGCGCC ATGACCTGTG CAGATGGCCC TTGCTTCAAT | 1140 |
| GGAGGACGAT GTTCAGATAA CCCTGACGGA GGCTACACCT GCCATTGCCC CTTGGGCAAT | 1200 |
| TCTGGCTTCA ACTGTGAGAA GAAGATGGAT CTCTGCGGCT CTTCCCCCTT GTTCTAACGG | 1260 |
| TGCCAAGTGT GTGGACCTCG GCAACTCTTA CCTGTGCCGG TGCCAGGCTG GCTTCTCCGG | 1320 |
| GACCTACTGC GAGGACAATG TGGATGACTG TGCCTCCTCC CCGTGTGCAA ATGGGGGCAC | 1380 |
| CTGCCGGGAC AGTGTGAACG ACTTCTCCTC TACCTGCCCA CCTGGCTACA CGGGCAAGAA | 1440 |
| CTGCAGCGCC CCTGTCAGCA GGTGTGAGCA TGCACCCTGC CATAATGGGG CCACCTGCCA | 1500 |
| CCAGAGGGGC CAGCGCTACA TGTGTGAGTG CGCCCAGGGC TATGGCGGCC CCAACTGCCA | 1560 |
| GTTTCTGCTC CCTGAGCCAC CACCAGGGCC CATGGTGGTG GACCTCAGTG AGAGGCATAT | 1620 |
| GGAGAGCCAG GGCGGGCCCT TCCCCTCGGT GGCGGTGTGT GCCGGGGTGG TGCTTGTCCT | 1680 |
| CCTGCTGCTG CTGGGCTGTG CTGCTGTGGT GGTCTGCGTC CGGCTGAAGC TACAGAAACA | 1740 |
| CCAGCCTCCA CCTGAACCCT GTGGGGGAGA GACAGAAACC ATGAACAACC TAGCCAATTG | 1800 |
| CCAGCGCGAG AAGGACGTTT CTGTTAGCAT CATTGGGGCT ACCCAGATCA AGAACACCAA | 1860 |
| CAAGAAGGCG GACTTTCACG GGGACCATGG AGCCAAGAAG AGCAGCTTTA AGGTCCGATA | 1920 |
| CCCCACTGTG GACTATAACC TCGTTCGAGA CCTCAAGGGA GATGAAGCCA CGGTCAGGGA | 1980 |
| TACACACAGC AAACGTGACA CCAAGTGCCA GTCACAGAGC TCTGCAGGAG AAGAGAAGAT | 2040 |
| CGCCCCAACA CTTAGGGGTG GGGAGATTCC TGACAGAAAA AGGCCAGAGT CTGTCTACTC | 2100 |
| TACTTCAAAG GACACCAAGT ACCAGTCGGT GTATGTTCTG TCTGCAGAAA AGGATGAGTG | 2160 |
| TGTTATAGCG ACTGAGCTGT AAGATGGAAG CGATGTGGCA AAATTCCCAT TTCTCTCAAA | 2220 |
| TAAAATTCCA AGGATATAGC CCCGATGAAT GCTGCTGAGA GAGGAAGGGA GAGGAAACCC | 2280 |
| AGGGACTGCT GCTGAGAACC AGGTTCAGGC GAAGCTGGTT CTCTCAGAGT TAGCAGAGGC | 2340 |
| GCCCGACACT GCCAGCCTAG GCTTTGGCTG CCGCTGGACT GCCTGCTGGT TGTTCCCATT | 2400 |
| GCACTATGGA CAGTTGCTTT GAAGAGTATA TATTTAAATG GACGAGTGAC TTGATTCATA | 2460 |
| TACGAAGCAC GCACTGCCCA CACGTCTATC TTGGATTACT ATGAGCCAGT CTTTCCTTGA | 2520 |
| ACTAGAAACA CAACTGCCTT TATTGTCCTT TTTGATACTG AGATGTGTTT TTTTTTTTCC | 2580 |
| TAGACGGGAA AAAGAAAACG TGTGTTATTT TTTTGGGATT TGTAAAAATA TTTTTCATGA | 2640 |

-continued

```
TATCTGTAAA GCTTGAGTAT TTTGTGACGT TCATTTTTTT ATAATTTAAA TTTTGGTAAA      2700

TATGTACAAA GGCACTTCGG GTCTATGTGA CTATATTTTT TTGTATATAA ATGTATTTAT      2760

GGAATATTGT GCAAATGTTA TTTGAGTTTT TTACTGTTTT GTTAATGAAG AAATTCATTT      2820

TAAAAATATT TTTCCAAAAT AAATATAATG AACTACA                              2857
```

(2) INFORMATION FOR SEQ ID NO: 5:

(i) SEQUENCE CHARACTERISTICS:
        (A) LENGTH: 721 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 5:

```
Met Gly Gln Gln Arg Met Leu Thr Leu Leu Val Leu Ser Ala Val Leu
 1               5                  10                  15

Cys Gln Ile Ser Cys Ser Gly Leu Phe Glu Leu Arg Leu Gln Glu Phe
             20                  25                  30

Val Asn Lys Lys Gly Leu Leu Gly Asn Met Asn Cys Cys Arg Pro Gly
         35                  40                  45

Ser Leu Ala Ser Leu Gln Arg Cys Glu Cys Lys Thr Phe Phe Arg Ile
 50                  55                  60

Cys Leu Lys His Tyr Gln Ser Asn Val Ser Pro Glu Pro Pro Cys Thr
65                  70                  75                  80

Tyr Gly Gly Ala Val Thr Pro Val Leu Gly Thr Asn Ser Phe Val Val
                 85                  90                  95

Pro Glu Ser Ser Asn Ala Asp Pro Thr Phe Ser Asn Pro Ile Arg Phe
            100                 105                 110

Pro Phe Gly Phe Thr Trp Pro Gly Thr Phe Ser Leu Ile Ile Glu Ala
        115                 120                 125

Ile His Ala Asp Ser Ala Asp Asp Leu Asn Thr Glu Asn Pro Glu Arg
130                 135                 140

Leu Ile Ser Arg Leu Ala Thr Gln Arg His Leu Thr Val Gly Glu Gln
145                 150                 155                 160

Trp Ser Gln Asp Leu His Ser Ser Asp Arg Thr Glu Leu Lys Tyr Ser
                165                 170                 175

Tyr Arg Phe Val Cys Asp Glu Tyr Tyr Tyr Gly Glu Gly Cys Ser Asp
            180                 185                 190

Tyr Cys Arg Pro Arg Asp Asp Ala Phe Gly His Phe Ser Cys Gly Glu
        195                 200                 205

Lys Gly Glu Lys Leu Cys Asn Pro Gly Trp Lys Gly Leu Tyr Cys Thr
    210                 215                 220

Glu Pro Ile Cys Leu Pro Gly Cys Asp Glu His His Gly Tyr Cys Asp
225                 230                 235                 240

Lys Pro Gly Glu Cys Lys Cys Arg Val Gly Trp Gln Gly Arg Tyr Cys
                245                 250                 255

Asp Glu Cys Ile Arg Tyr Pro Gly Cys Leu His Gly Thr Cys Gln Gln
            260                 265                 270

Pro Trp Gln Cys Asn Cys Gln Glu Gly Trp Gly Gly Leu Phe Cys Asn
        275                 280                 285

Gln Asp Leu Asn Tyr Cys Thr His His Lys Pro Cys Glu Asn Gly Ala
    290                 295                 300
```

-continued

```
Thr Cys Thr Asn Thr Gly Gln Gly Ser Tyr Thr Cys Ser Cys Arg Pro
305                 310                 315                 320

Gly Tyr Thr Gly Ser Asn Cys Glu Ile Glu Val Asn Glu Cys Asp Ala
                325                 330                 335

Asn Pro Cys Lys Asn Gly Gly Cys Ser Asp Leu Glu Asn Ser Tyr
            340                 345                 350

Thr Cys Ser Cys Pro Pro Gly Phe Tyr Gly Lys Asn Cys Glu Leu Ser
        355                 360                 365

Ala Met Thr Cys Ala Asp Gly Pro Cys Phe Asn Gly Gly Arg Cys Ala
    370                 375                 380

Asp Asn Pro Asp Gly Gly Tyr Ile Cys Phe Cys Pro Val Gly Tyr Ser
385                 390                 395                 400

Gly Phe Asn Cys Glu Lys Lys Ile Asp Tyr Cys Ser Ser Asn Pro Cys
                405                 410                 415

Ala Asn Gly Ala Arg Cys Glu Asp Leu Gly Asn Ser Tyr Ile Cys Gln
            420                 425                 430

Cys Gln Glu Gly Phe Ser Gly Arg Asn Cys Asp Asp Asn Leu Asp Asp
        435                 440                 445

Cys Thr Ser Phe Pro Cys Gln Asn Gly Gly Thr Cys Gln Asp Gly Ile
    450                 455                 460

Asn Asp Tyr Ser Cys Thr Cys Pro Pro Gly Tyr Ile Gly Lys Asn Cys
465                 470                 475                 480

Ser Met Pro Ile Thr Lys Cys Glu His Asn Pro Cys His Asn Gly Ala
                485                 490                 495

Thr Cys His Glu Arg Asn Asn Arg Tyr Val Cys Gln Cys Ala Arg Gly
            500                 505                 510

Tyr Gly Gly Asn Asn Cys Gln Phe Leu Leu Pro Glu Glu Lys Pro Val
        515                 520                 525

Val Val Asp Leu Thr Glu Lys Tyr Thr Glu Gly Gln Ser Gly Gln Phe
    530                 535                 540

Pro Trp Ile Ala Val Cys Ala Gly Ile Val Leu Val Leu Met Leu Leu
545                 550                 555                 560

Leu Gly Cys Ala Ala Val Val Cys Val Arg Val Arg Val Gln Lys
                565                 570                 575

Arg Arg His Gln Pro Glu Ala Cys Arg Gly Glu Ser Lys Thr Met Asn
            580                 585                 590

Asn Leu Ala Asn Cys Gln Arg Glu Lys Asp Ile Ser Val Ser Phe Ile
        595                 600                 605

Gly Thr Thr Gln Ile Lys Asn Thr Asn Lys Lys Ile Asp Phe Leu Ser
    610                 615                 620

Glu Ser Asn Asn Glu Lys Asn Gly Tyr Lys Pro Arg Tyr Pro Ser Val
625                 630                 635                 640

Asp Tyr Asn Leu Val His Glu Leu Lys Asn Glu Asp Ser Pro Lys Glu
                645                 650                 655

Glu Arg Ser Lys Cys Glu Ala Lys Cys Ser Ser Asn Asp Ser Asp Ser
            660                 665                 670

Glu Asp Val Asn Ser Val His Ser Lys Arg Asp Ser Ser Glu Arg Arg
        675                 680                 685

Arg Pro Asp Ser Ala Tyr Ser Thr Ser Lys Asp Thr Lys Tyr Gln Ser
    690                 695                 700

Val Tyr Val Ile Ser Asp Glu Lys Asp Glu Cys Ile Ile Ala Thr Glu
705                 710                 715                 720

Val
```

(2) INFORMATION FOR SEQ ID NO: 6:

(i) SEQUENCE CHARACTERISTICS:
        (A) LENGTH: 832 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 6:

```
Met His Trp Ile Lys Cys Leu Leu Thr Ala Phe Ile Cys Phe Thr Val
 1               5                  10                  15

Ile Val Gln Val His Ser Ser Gly Ser Phe Glu Leu Arg Leu Lys Tyr
             20                  25                  30

Phe Ser Asn Asp His Gly Arg Asp Asn Glu Gly Arg Cys Cys Ser Gly
             35                  40                  45

Glu Ser Asp Gly Ala Thr Gly Lys Cys Leu Gly Ser Cys Lys Thr Arg
 50                  55                  60

Phe Arg Leu Cys Leu Lys His Tyr Gln Ala Thr Ile Asp Thr Thr Ser
65                   70                  75                  80

Gln Cys Thr Tyr Gly Asp Val Ile Thr Pro Ile Leu Gly Glu Asn Ser
                 85                  90                  95

Val Asn Leu Thr Asp Ala Gln Arg Phe Gln Asn Lys Gly Phe Thr Asn
             100                 105                 110

Pro Ile Gln Phe Pro Phe Ser Phe Ser Trp Pro Gly Thr Phe Ser Leu
             115                 120                 125

Ile Val Glu Ala Trp His Asp Thr Asn Asn Ser Gly Asn Ala Arg Thr
130                 135                 140

Asn Lys Leu Leu Ile Gln Arg Leu Leu Val Gln Gln Val Leu Glu Val
145                 150                 155                 160

Ser Ser Glu Trp Lys Thr Asn Lys Ser Glu Ser Gln Tyr Thr Ser Leu
                 165                 170                 175

Glu Tyr Asp Phe Arg Val Thr Cys Asp Leu Asn Tyr Tyr Gly Ser Gly
             180                 185                 190

Cys Ala Lys Phe Cys Arg Pro Arg Asp Asp Ser Phe Gly His Ser Thr
             195                 200                 205

Cys Ser Glu Thr Gly Glu Ile Ile Cys Leu Thr Gly Trp Gln Gly Asp
210                 215                 220

Tyr Cys His Ile Pro Lys Cys Ala Lys Gly Cys Glu His Gly His Cys
225                 230                 235                 240

Asp Lys Pro Asn Gln Cys Val Cys Gln Leu Gly Trp Lys Gly Ala Leu
                 245                 250                 255

Cys Asn Glu Cys Val Leu Glu Pro Asn Cys Ile His Gly Thr Cys Asn
             260                 265                 270

Lys Pro Trp Thr Cys Ile Cys Asn Glu Gly Trp Gly Gly Leu Tyr Cys
             275                 280                 285

Asn Gln Asp Leu Asn Tyr Cys Thr Asn His Arg Pro Cys Lys Asn Gly
290                 295                 300

Gly Thr Cys Phe Asn Thr Gly Glu Gly Leu Tyr Thr Cys Lys Cys Ala
305                 310                 315                 320

Pro Gly Tyr Ser Gly Asp Asp Cys Glu Asn Glu Ile Tyr Ser Cys Asp
                 325                 330                 335

Ala Asp Val Asn Pro Cys Gln Asn Gly Gly Thr Cys Ile Asp Glu Pro
             340                 345                 350
```

```
His Thr Lys Thr Gly Tyr Lys Cys His Cys Arg Asn Gly Trp Ser Gly
        355                 360                 365
Lys Met Cys Glu Glu Lys Val Leu Thr Cys Ser Asp Lys Pro Cys His
    370                 375                 380
Gln Gly Ile Cys Arg Asn Val Arg Pro Gly Leu Gly Ser Lys Gly Gln
385                 390                 395                 400
Gly Tyr Gln Cys Glu Cys Pro Ile Gly Tyr Ser Gly Pro Asn Cys Asp
                405                 410                 415
Leu Gln Leu Asp Asn Cys Ser Pro Asn Pro Cys Ile Asn Gly Gly Ser
            420                 425                 430
Cys Gln Pro Ser Gly Lys Cys Ile Cys Pro Ser Gly Phe Ser Gly Thr
            435                 440                 445
Arg Cys Glu Thr Asn Ile Asp Asp Cys Leu Gly His Gln Cys Glu Asn
    450                 455                 460
Gly Gly Thr Cys Ile Asp Met Val Asn Gln Tyr Arg Cys Gln Cys Val
465                 470                 475                 480
Pro Gly Phe His Gly Thr His Cys Ser Ser Lys Val Asp Leu Cys Leu
                485                 490                 495
Ile Arg Pro Cys Ala Asn Gly Gly Thr Cys Leu Asn Leu Asn Asn Asp
            500                 505                 510
Tyr Gln Cys Thr Cys Arg Ala Gly Phe Thr Gly Lys Asp Cys Ser Val
            515                 520                 525
Asp Ile Asp Glu Cys Ser Ser Gly Pro Cys His Asn Gly Gly Thr Cys
    530                 535                 540
Met Asn Arg Val Asn Ser Phe Glu Cys Val Cys Ala Asn Gly Phe Arg
545                 550                 555                 560
Gly Lys Gln Cys Asp Glu Glu Ser Tyr Asp Ser Val Thr Phe Asp Ala
                565                 570                 575
His Gln Tyr Gly Ala Thr Thr Gln Ala Arg Ala Asp Gly Leu Ala Asn
            580                 585                 590
Ala Gln Val Val Leu Ile Ala Val Phe Ser Val Ala Met Pro Leu Val
    595                 600                 605
Ala Val Ile Ala Ala Cys Val Val Phe Cys Met Lys Arg Lys Arg Lys
    610                 615                 620
Arg Ala Gln Glu Lys Asp Asn Ala Glu Ala Arg Lys Gln Asn Glu Gln
625                 630                 635                 640
Asn Ala Val Ala Thr Met His His Asn Gly Ser Ala Val Gly Val Ala
                645                 650                 655
Leu Ala Ser Ala Ser Met Gly Gly Lys Thr Gly Ser Asn Ser Gly Leu
            660                 665                 670
Thr Phe Asp Gly Gly Asn Pro Asn Ile Ile Lys Asn Thr Trp Asp Lys
    675                 680                 685
Ser Val Asn Asn Ile Cys Ala Ser Ala Ala Ala Ala Ala Ala Ala Ala
    690                 695                 700
Ala Ala Ala Asp Glu Cys Leu Met Tyr Gly Gly Tyr Val Ala Ser Val
705                 710                 715                 720
Ala Asp Asn Asn Asn Ala Asn Ser Asp Phe Cys Val Ala Pro Leu Gln
                725                 730                 735
Arg Ala Lys Ser Gln Lys Gln Leu Asn Thr Asp Pro Thr Leu Met His
            740                 745                 750
Arg Gly Ser Pro Ala Gly Thr Ser Ala Lys Gly Ala Ser Gly Gly Gly
            755                 760                 765
```

```
Pro Gly Ala Ala Glu Gly Lys Arg Ile Ser Val Leu Gly Glu Gly Ser
    770                 775                 780
Tyr Cys Ser Gln Arg Trp Pro Ser Leu Ala Ala Gly Val Ala Gly
785                 790                 795                 800
Asp Leu Phe Ile Gln Leu Met Ala Ala Ala Ser Val Ala Gly Thr Asp
                805                 810                 815
Gly Thr Ala Gln Gln Gln Arg Ser Val Val Cys Gly Thr Pro His Met
            820                 825                 830

(2) INFORMATION FOR SEQ ID NO: 7:

(i) SEQUENCE CHARACTERISTICS:
        (A) LENGTH: 46 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 7:

Val Gln Cys Ala Val Thr Tyr Tyr Asn Thr Thr Phe Cys Thr Thr Phe
1               5                   10                  15
Cys Arg Pro Arg Asp Asp Gln Phe Gly His Tyr Ala Cys Gly Ser Glu
                20                  25                  30
Gly Gln Lys Leu Cys Leu Asn Gly Trp Gln Gly Val Asn Cys
            35                  40                  45

(2) INFORMATION FOR SEQ ID NO: 8:

(i) SEQUENCE CHARACTERISTICS:
        (A) LENGTH: 45 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 8:

Val Thr Cys Ala Glu His Tyr Tyr Gly Phe Gly Cys Asn Lys Phe Cys
1               5                   10                  15
Arg Pro Arg Asp Asp Phe Phe Thr His His Thr Cys Asp Gln Asn Gly
                20                  25                  30
Asn Lys Thr Cys Leu Glu Gly Trp Thr Gly Pro Glu Cys
            35                  40                  45

(2) INFORMATION FOR SEQ ID NO: 9:

(i) SEQUENCE CHARACTERISTICS:
        (A) LENGTH: 43 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 9:

Asn Leu Cys Ser Ser Asn Tyr His Gly Lys Arg Cys Asn Arg Tyr Cys
1               5                   10                  15
Ile Ala Asn Ala Lys Leu His Trp Glu Cys Ser Thr His Gly Val Arg
                20                  25                  30
Arg Cys Ser Ala Gly Trp Ser Gly Glu Asp Cys
            35                  40
```

(2) INFORMATION FOR SEQ ID NO: 10:

(i) SEQUENCE CHARACTERISTICS:
        (A) LENGTH: 45 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 10:

```
Val Thr Cys Ala Arg Asn Tyr Phe Gly Asn Arg Cys Glu Asn Phe Cys
 1               5                  10                  15

Asp Ala His Leu Ala Lys Ala Ala Arg Lys Arg Cys Asp Ala Met Gly
            20                  25                  30

Arg Leu Arg Cys Asp Ile Gly Trp Met Gly Pro His Cys
        35                  40                  45
```

(2) INFORMATION FOR SEQ ID NO: 11:

(i) SEQUENCE CHARACTERISTICS:
        (A) LENGTH: 2692 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 34...2199
        (D) OTHER INFORMATION:

(xi) SEQUENCE DESCRIPTION: SEQ ID NO: 11:

```
CTGCAGGAAT TCSMYCGCAT GCTCCCGGCC GCC ATG GGC CGT CGG AGC GCG CTA       54
                                    Met Gly Arg Arg Ser Ala Leu
                                     1               5

GCC CTT GCC GTG GTC TCT GCC CTG CTG TGC CAG GTC TGG AGC TCC GGC       102
Ala Leu Ala Val Val Ser Ala Leu Leu Cys Gln Val Trp Ser Ser Gly
         10                  15                  20

GTA TTT GAG CTG AAG CTG CAG GAG TTC GTC AAC AAG AAG GGG CTG CTG       150
Val Phe Glu Leu Lys Leu Gln Glu Phe Val Asn Lys Lys Gly Leu Leu
 25                  30                  35

GGG AAC CGC AAC TGC TGC CGC GGG GGC TCT GGC CCG CCT TGC GCC TGC       198
Gly Asn Arg Asn Cys Cys Arg Gly Gly Ser Gly Pro Pro Cys Ala Cys
 40                  45                  50                  55

AGG ACC TTC TTT CGC GTA TGC CTC AAG CAC TAC CAG GCC AGC GTG TCA       246
Arg Thr Phe Phe Arg Val Cys Leu Lys His Tyr Gln Ala Ser Val Ser
             60                  65                  70

CCG GAG CCA CCC TGC ACC TAC GGC AGT GCC GTC ACG CCA GTG CTG GGT       294
Pro Glu Pro Pro Cys Thr Tyr Gly Ser Ala Val Thr Pro Val Leu Gly
             75                  80                  85

GTC GAC TCC TTC AGC CTG CCT GAT GGC GCA GGC ATC GAC CCC GCC TTC       342
Val Asp Ser Phe Ser Leu Pro Asp Gly Ala Gly Ile Asp Pro Ala Phe
             90                  95                 100

AGC AAC CCC ATC CGA TTC CCC TTC GGC TTC ACC TGG CCA GGT ACC TTC       390
Ser Asn Pro Ile Arg Phe Pro Phe Gly Phe Thr Trp Pro Gly Thr Phe
            105                 110                 115

TCT CTG ATC ATT GAA GCC CTC CAT ACA GAC TCT CCC GAT GAC CTC GCA       438
Ser Leu Ile Ile Glu Ala Leu His Thr Asp Ser Pro Asp Asp Leu Ala
120                 125                 130                 135

ACA GAA AAC CCA GAA AGA CTC ATC AGC CGC CTG ACC ACA CAG AGG CAC       486
Thr Glu Asn Pro Glu Arg Leu Ile Ser Arg Leu Thr Thr Gln Arg His
            140                 145                 150
```

|     |     |
| --- | --- |
| CTC ACT GTG GGA GAA GAA TGG TCT CAG GAC CTT CAC AGT AGC GGC CGC<br>Leu Thr Val Gly Glu Glu Trp Ser Gln Asp Leu His Ser Ser Gly Arg<br>155                       160                     165 | 534 |
| ACA GAC CTC CGG TAC TCT TAC CGG TTT GTG TGT GAC GAG CAC TAC TAC<br>Thr Asp Leu Arg Tyr Ser Tyr Arg Phe Val Cys Asp Glu His Tyr Tyr<br>    170                   175                   180 | 582 |
| GGA GAA GGT TGC TCT GTG TTC TGC CGA CCT CGG GAT GAC GCC TTT GGC<br>Gly Glu Gly Cys Ser Val Phe Cys Arg Pro Arg Asp Asp Ala Phe Gly<br>185                       190                   195 | 630 |
| CAC TTC ACC TGC GGG GAC AGA GGG GAG AAG ATG TGC GAC CCT GGC TGG<br>His Phe Thr Cys Gly Asp Arg Gly Glu Lys Met Cys Asp Pro Gly Trp<br>200                   205                   210                   215 | 678 |
| AAA GGC CAG TAC TGC ACT GAC CCA ATC TGT CTG CCA GGG TGT GAT GAC<br>Lys Gly Gln Tyr Cys Thr Asp Pro Ile Cys Leu Pro Gly Cys Asp Asp<br>         220                   225                   230 | 726 |
| CAA CAT GGA TAC TGT GAC AAA CCA GGG GAG TGC AAG TGC AGA GTT GGC<br>Gln His Gly Tyr Cys Asp Lys Pro Gly Glu Cys Lys Cys Arg Val Gly<br>               235                   240                   245 | 774 |
| TGG CAG GGC CGC TAC TGC GAT GAG TGC ATC CGA TAC CCA GGT TGT GTC<br>Trp Gln Gly Arg Tyr Cys Asp Glu Cys Ile Arg Tyr Pro Gly Cys Val<br>       250                   255                   260 | 822 |
| CAT GGC ACC TGC CAG CAA CCC TGG CAG TGT AAC TGC CAG GAA GGC TGG<br>His Gly Thr Cys Gln Gln Pro Trp Gln Cys Asn Cys Gln Glu Gly Trp<br>265                       270                   275 | 870 |
| GGG GGC CTT TTC TGC AAC CAA GAC CTG AAC TAC TGT ACT CAC CAT AAG<br>Gly Gly Leu Phe Cys Asn Gln Asp Leu Asn Tyr Cys Thr His His Lys<br>280                       285                   290                   295 | 918 |
| CCG TGC AGG AAT GGA GCC ACC TGC ACC AAC ACG GGC CAG GGG AGC TAC<br>Pro Cys Arg Asn Gly Ala Thr Cys Thr Asn Thr Gly Gln Gly Ser Tyr<br>               300                   305                   310 | 966 |
| ACA TGT TCC TGC CGA CCT GGG TAT ACA GGT GCC AAC TGT GAG CTG GAA<br>Thr Cys Ser Cys Arg Pro Gly Tyr Thr Gly Ala Asn Cys Glu Leu Glu<br>                   315                   320                   325 | 1014 |
| GTA GAT GAG TGT GCT CCT AGC CCC TGC AAG AAC GGA GCG AGC TGC ACG<br>Val Asp Glu Cys Ala Pro Ser Pro Cys Lys Asn Gly Ala Ser Cys Thr<br>         330                   335                   340 | 1062 |
| GAC CTT GAG GAC AGC TTC TCT TGC ACC TGC CCT CCC GGC TTC TAT GGC<br>Asp Leu Glu Asp Ser Phe Ser Cys Thr Cys Pro Pro Gly Phe Tyr Gly<br>345                       350                   355 | 1110 |
| AAG GTC TGT GAG CTG AGC GCC ATG ACC TGT GCA GAT GGC CCT TGC TTC<br>Lys Val Cys Glu Leu Ser Ala Met Thr Cys Ala Asp Gly Pro Cys Phe<br>360                       365                   370                   375 | 1158 |
| AAT GGA GGA CGA TGT TCA GAT AAC CCT GAC GGA GGC TAC ACC TGC CAT<br>Asn Gly Gly Arg Cys Ser Asp Asn Pro Asp Gly Gly Tyr Thr Cys His<br>               380                   385                   390 | 1206 |
| TGC CCC TTG GGC TTC TCT GGC TTC AAC TGT GAG AAG AAG ATG GAT CTC<br>Cys Pro Leu Gly Phe Ser Gly Phe Asn Cys Glu Lys Lys Met Asp Leu<br>                   395                   400                   405 | 1254 |
| TGC GGC TCT TCC CCT TGT TCT AAC GGT GCC AAG TGT GTG GAC CTC GGC<br>Cys Gly Ser Ser Pro Cys Ser Asn Gly Ala Lys Cys Val Asp Leu Gly<br>               410                   415                   420 | 1302 |
| AAC TCT TAC CTG TGC CGG TGC CAG GCT GGC TTC TCC GGG AGG TAC TGC<br>Asn Ser Tyr Leu Cys Arg Cys Gln Ala Gly Phe Ser Gly Arg Tyr Cys<br>         425                   430                   435 | 1350 |
| GAG GAC AAT GTG GAT GAC TGT GCC TCC TCC CCG TGT GCA AAT GGG GGC<br>Glu Asp Asn Val Asp Asp Cys Ala Ser Ser Pro Cys Ala Asn Gly Gly<br>440                       445                   450                   455 | 1398 |
| ACC TGC CGG GAC AGT GTG AAC GAC TTC TCC TGT ACC TGC CCA CCT GGC<br>Thr Cys Arg Asp Ser Val Asn Asp Phe Ser Cys Thr Cys Pro Pro Gly<br>               460                   465                   470 | 1446 |

```
TAC ACG GGC AAG AAC TGC AGC GCC CCT GTC AGC AGG TGT GAG CAT GCA      1494
Tyr Thr Gly Lys Asn Cys Ser Ala Pro Val Ser Arg Cys Glu His Ala
            475                 480                 485

CCC TGC CAT AAT GGG GCC ACC TGC CAC CAG AGG GGC CAG CGC TAC ATG      1542
Pro Cys His Asn Gly Ala Thr Cys His Gln Arg Gly Gln Arg Tyr Met
            490                 495                 500

TGT GAG TGC GCC CAG GGC TAT GGC GGC CCC AAC TGC CAG TTT CTG CTC      1590
Cys Glu Cys Ala Gln Gly Tyr Gly Gly Pro Asn Cys Gln Phe Leu Leu
            505                 510                 515

CCT GAG CCA CCA CCA GGG CCC ATG GTG GTG GAC CTC AGT GAG AGG CAT      1638
Pro Glu Pro Pro Pro Gly Pro Met Val Val Asp Leu Ser Glu Arg His
520                 525                 530                 535

ATG GAG AGC CAG GGC GGG CCC TTC CCC TGG GTG GCC GTG TGT GCC GGG      1686
Met Glu Ser Gln Gly Gly Pro Phe Pro Trp Val Ala Val Cys Ala Gly
            540                 545                 550

GTG GTG CTT GTC CTC CTG CTG CTG GGC TGT GCT GCT GTG GTG GTC          1734
Val Val Leu Val Leu Leu Leu Leu Gly Cys Ala Ala Val Val Val
            555                 560                 565

TGC GTC CGG CTG AAG CTA CAG AAA CAC CAG CCT CCA CCT GAA CCC TGT      1782
Cys Val Arg Leu Lys Leu Gln Lys His Gln Pro Pro Pro Glu Pro Cys
            570                 575                 580

GGG GGA GAG ACA GAA ACC ATG AAC AAC CTA GCC AAT TGC CAG CGC GAG      1830
Gly Gly Glu Thr Glu Thr Met Asn Asn Leu Ala Asn Cys Gln Arg Glu
585                 590                 595

AAG GAC GTT TCT GTT AGC ATC ATT GGG GCT ACC CAG ATC AAG AAC ACC      1878
Lys Asp Val Ser Val Ser Ile Ile Gly Ala Thr Gln Ile Lys Asn Thr
600                 605                 610                 615

AAC AAG AAG GCG GAC TTT CAC GGG GAC CAT GGA GCC GAG AAG AGC AGC      1926
Asn Lys Lys Ala Asp Phe His Gly Asp His Gly Ala Glu Lys Ser Ser
            620                 625                 630

TTT AAG GTC CGA TAC CCC ACT GTG GAC TAT AAC CTC GTT CGA GAC CTC      1974
Phe Lys Val Arg Tyr Pro Thr Val Asp Tyr Asn Leu Val Arg Asp Leu
            635                 640                 645

AAG GGA GAT GAA GCC ACG GTC AGG GAT ACA CAC AGC AAA CGT GAC ACC      2022
Lys Gly Asp Glu Ala Thr Val Arg Asp Thr His Ser Lys Arg Asp Thr
            650                 655                 660

AAG TGC CAG TCA CAG AGT CTG CAG GAG AAG AGA AGA TCG CCC CAA CAC      2070
Lys Cys Gln Ser Gln Ser Leu Gln Glu Lys Arg Arg Ser Pro Gln His
665                 670                 675

TTA GGG GTG GGG AGA TTC CTG ACA GAA AAC AGG CCA GAG TCT GTC TAC      2118
Leu Gly Val Gly Arg Phe Leu Thr Glu Asn Arg Pro Glu Ser Val Tyr
680                 685                 690                 695

TCT ACT TCA AAG GAC ACC AAG TAC CAG TCG GTG TAT GTT CTG TCT GCA      2166
Ser Thr Ser Lys Asp Thr Lys Tyr Gln Ser Val Tyr Val Leu Ser Ala
            700                 705                 710

GAA AAG GAT GAG TGT GTT ATA GCG ACT GAG GTG TAAGATGGAA GCGATGT       2219
Glu Lys Asp Glu Cys Val Ile Ala Thr Glu Val
            715                 720

AAAATTCCCA TTTCTCTTAA ATAAAATTCC AAGGATATAG CCCCGATGAA TGCTGCTGAG    2279

AGAGGAAGGG AGAGGAAACC CAGGGACTGC TGCTGAGAAC CAGGTTCAGG CGAACGTGGT    2339

TCTCTCAGAG TTAGCAGAGG CGCCCGACAC TGCCAGCCTA GGCTTTGGCT GCCGCTGGAC    2399

TGCCTGCTGG TTGTTCCCAT TGCACTATGG ACAGTTGCTT TGAAGAGTAT ATATTTAAAT    2459

GGACGAGTGA CTTGATTCAT ATAGGAAGCA CGCACTGCCC ACACGTCTAT CTTGGATTAC    2519

TATGAGCCAG TCTTTCCTTG AACTAGAAAC ACAACTGCCT TTATTGTCCT TTTTGATACT    2579

GAGATGTGTT TTTTTTTTTT CCTAGACGGG AAAAAGAAAA CGTGTGTTAT TTTTTTTGGG    2639
```

```
ATTTGTAAAA ATATTTTTCA TGATTATGGG AGAGCTCCCA ACGCGTTGGA GGT         2692
```

(2) INFORMATION FOR SEQ ID NO: 12:

(i) SEQUENCE CHARACTERISTICS:
        (A) LENGTH: 722 amino acids
        (B) TYPE: amino acid
        (C) STRANDEDNESS: <Unknown>
        (D) TOPOLOGY: unknown (ii) MOLECULE TYPE: protein (xi) SEQUENCE DESCRIPTION: SEQ ID NO: 12:

```
Met Gly Arg Arg Ser Ala Leu Ala Leu Ala Val Val Ser Ala Leu Leu
 1               5                  10                  15

Cys Gln Val Trp Ser Ser Gly Val Phe Glu Leu Lys Leu Gln Glu Phe
            20                  25                  30

Val Asn Lys Lys Gly Leu Leu Gly Asn Arg Asn Cys Cys Arg Gly Gly
        35                  40                  45

Ser Gly Pro Pro Cys Ala Cys Arg Thr Phe Phe Arg Val Cys Leu Lys
 50                  55                  60

His Tyr Gln Ala Ser Val Ser Pro Glu Pro Pro Cys Thr Tyr Gly Ser
65                  70                  75                  80

Ala Val Thr Pro Val Leu Gly Val Asp Ser Phe Ser Leu Pro Asp Gly
                85                  90                  95

Ala Gly Ile Asp Pro Ala Phe Ser Asn Pro Ile Arg Phe Pro Phe Gly
            100                 105                 110

Phe Thr Trp Pro Gly Thr Phe Ser Leu Ile Ile Glu Ala Leu His Thr
        115                 120                 125

Asp Ser Pro Asp Asp Leu Ala Thr Glu Asn Pro Glu Arg Leu Ile Ser
130                 135                 140

Arg Leu Thr Thr Gln Arg His Leu Thr Val Gly Glu Glu Trp Ser Gln
145                 150                 155                 160

Asp Leu His Ser Ser Gly Arg Thr Asp Leu Arg Tyr Ser Tyr Arg Phe
                165                 170                 175

Val Cys Asp Glu His Tyr Tyr Gly Glu Gly Cys Ser Val Phe Cys Arg
            180                 185                 190

Pro Arg Asp Asp Ala Phe Gly His Phe Thr Cys Gly Asp Arg Gly Glu
        195                 200                 205

Lys Met Cys Asp Pro Gly Trp Lys Gly Gln Tyr Cys Thr Asp Pro Ile
210                 215                 220

Cys Leu Pro Gly Cys Asp Asp Gln His Gly Tyr Cys Asp Lys Pro Gly
225                 230                 235                 240

Glu Cys Lys Cys Arg Val Gly Trp Gln Gly Arg Tyr Cys Asp Glu Cys
                245                 250                 255

Ile Arg Tyr Pro Gly Cys Val His Gly Thr Cys Gln Gln Pro Trp Gln
            260                 265                 270

Cys Asn Cys Gln Glu Gly Trp Gly Gly Leu Phe Cys Asn Gln Asp Leu
        275                 280                 285

Asn Tyr Cys Thr His His Lys Pro Cys Arg Asn Gly Ala Thr Cys Thr
290                 295                 300

Asn Thr Gly Gln Gly Ser Tyr Thr Cys Ser Cys Arg Pro Gly Tyr Thr
305                 310                 315                 320

Gly Ala Asn Cys Glu Leu Glu Val Asp Glu Cys Ala Pro Ser Pro Cys
                325                 330                 335

Lys Asn Gly Ala Ser Cys Thr Asp Leu Glu Asp Ser Phe Ser Cys Thr
```

```
                    340                 345                 350
Cys Pro Pro Gly Phe Tyr Gly Lys Val Cys Glu Leu Ser Ala Met Thr
                355                 360                 365
Cys Ala Asp Gly Pro Cys Phe Asn Gly Gly Arg Cys Ser Asp Asn Pro
            370                 375                 380
Asp Gly Gly Tyr Thr Cys His Cys Pro Leu Gly Phe Ser Gly Phe Asn
385                 390                 395                 400
Cys Glu Lys Lys Met Asp Leu Cys Gly Ser Ser Pro Cys Ser Asn Gly
                405                 410                 415
Ala Lys Cys Val Asp Leu Gly Asn Ser Tyr Leu Cys Arg Cys Gln Ala
            420                 425                 430
Gly Phe Ser Gly Arg Tyr Cys Glu Asp Asn Val Asp Asp Cys Ala Ser
435                 440                 445
Ser Pro Cys Ala Asn Gly Gly Thr Cys Arg Asp Ser Val Asn Asp Phe
    450                 455                 460
Ser Cys Thr Cys Pro Pro Gly Tyr Thr Gly Lys Asn Cys Ser Ala Pro
465                 470                 475                 480
Val Ser Arg Cys Glu His Ala Pro Cys His Asn Gly Ala Thr Cys His
                485                 490                 495
Gln Arg Gly Gln Arg Tyr Met Cys Glu Cys Ala Gln Gly Tyr Gly Gly
            500                 505                 510
Pro Asn Cys Gln Phe Leu Leu Pro Glu Pro Pro Gly Pro Met Val
            515                 520                 525
Val Asp Leu Ser Glu Arg His Met Glu Ser Gln Gly Gly Pro Phe Pro
530                 535                 540
Trp Val Ala Val Cys Ala Gly Val Val Leu Val Leu Leu Leu Leu Leu
545                 550                 555                 560
Gly Cys Ala Ala Val Val Cys Val Arg Leu Lys Leu Gln Lys His
            565                 570                 575
Gln Pro Pro Pro Glu Pro Cys Gly Gly Glu Thr Glu Thr Met Asn Asn
            580                 585                 590
Leu Ala Asn Cys Gln Arg Glu Lys Asp Val Ser Val Ser Ile Ile Gly
        595                 600                 605
Ala Thr Gln Ile Lys Asn Thr Asn Lys Lys Ala Asp Phe His Gly Asp
    610                 615                 620
His Gly Ala Glu Lys Ser Ser Phe Lys Val Arg Tyr Pro Thr Val Asp
625                 630                 635                 640
Tyr Asn Leu Val Arg Asp Leu Lys Gly Asp Glu Ala Thr Val Arg Asp
                645                 650                 655
Thr His Ser Lys Arg Asp Thr Lys Cys Gln Ser Gln Ser Leu Gln Glu
            660                 665                 670
Lys Arg Arg Ser Pro Gln His Leu Gly Val Gly Arg Phe Leu Thr Glu
        675                 680                 685
Asn Arg Pro Glu Ser Val Tyr Ser Thr Ser Lys Asp Thr Lys Tyr Gln
    690                 695                 700
Ser Val Tyr Val Leu Ser Ala Glu Lys Asp Glu Cys Val Ile Ala Thr
705                 710                 715                 720
Glu Val (2) INFORMATION FOR SEQ ID NO: 13:

(i) SEQUENCE CHARACTERISTICS:
        (A) LENGTH: 578 amino acids
        (B) TYPE: amino acid
```

(C) STRANDEDNESS: <Unknown>
(D) TOPOLOGY: unknown (ii) MOLECULE TYPE: peptide (xi) SEQUENCE DESCRIPTION: SEQ ID NO: 13:

```
Met Gly Arg Leu Leu Ala Ser Ala Leu Leu Cys Val Ser Gly Val Phe
 1               5                  10                  15

Glu Leu Lys Leu Gln Glu Phe Val Asn Lys Lys Gly Leu Leu Asn Arg
            20                  25                  30

Asn Cys Cys Arg Gly Gly Cys Cys Thr Phe Phe Arg Val Cys Leu
        35                  40                  45

Lys His Tyr Gln Ala Ser Val Ser Pro Glu Pro Cys Thr Tyr Gly
    50                  55                  60

Ser Ala Thr Pro Val Leu Gly Ser Phe Ser Asp Gly Ala Gly Asp
65                  70                  75                  80

Pro Ala Phe Ser Asn Pro Ile Arg Phe Pro Phe Gly Phe Thr Trp Pro
                85                  90                  95

Gly Thr Phe Ser Leu Ile Ile Glu Ala Leu His Thr Asp Ser Pro Asp
                100                 105                 110

Asp Leu Thr Glu Asn Pro Glu Arg Leu Ile Ser Arg Leu Thr Gln Arg
            115                 120                 125

His Leu Val Gly Glu Glu Trp Ser Gln Asp Leu His Ser Ser Gly Arg
    130                 135                 140

Thr Asp Leu Tyr Ser Tyr Arg Phe Val Cys Asp Glu His Tyr Tyr Gly
145                 150                 155                 160

Glu Gly Cys Ser Val Phe Cys Arg Pro Arg Asp Asp Phe Gly His Phe
                165                 170                 175

Thr Cys Gly Arg Gly Glu Lys Cys Pro Gly Trp Lys Gly Gln Tyr Cys
                180                 185                 190

Thr Pro Ile Cys Leu Pro Gly Cys Asp Gln His Gly Cys Asp Lys Pro
            195                 200                 205

Gly Glu Cys Lys Cys Arg Val Gly Trp Gln Gly Arg Tyr Cys Asp Glu
    210                 215                 220

Cys Ile Arg Tyr Pro Gly Cys Val His Gly Thr Cys Gln Gln Pro Trp
225                 230                 235                 240

Gln Cys Asn Cys Gln Glu Gly Trp Gly Gly Leu Phe Cys Asn Gln Asp
                245                 250                 255

Leu Asn Tyr Cys Thr His His Lys Pro Cys Asn Gly Ala Thr Cys Thr
            260                 265                 270

Asn Thr Gly Gln Gly Ser Tyr Thr Cys Ser Cys Arg Pro Gly Tyr Thr
    275                 280                 285

Gly Cys Glu Glu Glu Cys Pro Cys Lys Asn Gly Ser Cys Thr Asp Leu
290                 295                 300

Glu Ser Ser Cys Thr Cys Pro Pro Gly Phe Tyr Gly Lys Cys Glu Leu
305                 310                 315                 320

Ser Ala Met Thr Cys Ala Asp Gly Pro Cys Phe Asn Gly Gly Arg Cys
                325                 330                 335

Asp Asn Pro Asp Gly Gly Tyr Cys Cys Pro Leu Gly Ser Gly Phe Asn
            340                 345                 350

Cys Glu Lys Lys Asp Cys Ser Ser Pro Cys Asn Gly Ala Cys Val Asp
    355                 360                 365

Leu Gly Asn Ser Tyr Cys Cys Gln Ala Gly Phe Gly Arg Cys Asp Asn
370                 375                 380
```

```
Val Asp Asp Cys Ala Ser Pro Cys Asn Gly Gly Thr Cys Asp Val Asn
385                 390                 395                 400

Asp Ser Cys Thr Cys Pro Pro Gly Tyr Gly Lys Asn Cys Ser Pro Val
            405                 410                 415

Ser Arg Cys Glu His Pro Cys His Asn Gly Ala Thr Cys His Arg Arg
        420                 425                 430

Tyr Cys Glu Cys Ala Gly Tyr Gly Gly Asn Cys Gln Phe Leu Leu Pro
        435                 440                 445

Glu Pro Pro Gly Pro Val Asp Glu Glu Gln Phe Pro Trp Ala Val Cys
450                 455                 460

Ala Gly Leu Val Leu Leu Leu Gly Cys Ala Ala Val Val Cys Val
465                 470                 475                 480

Arg Leu Lys Gln Lys Pro Glu Cys Glu Thr Glu Thr Met Asn Asn Leu
            485                 490                 495

Ala Asn Cys Gln Arg Glu Lys Asp Ser Ser Ile Gly Ala Thr Gln Ile
        500                 505                 510

Lys Asn Thr Asn Lys Lys Asp Phe His Asp Lys Lys Val Arg Tyr Pro
        515                 520                 525

Val Asp Tyr Asn Leu Val Leu Lys Val His Lys Lys Cys Ser Glu Glu
530                 535                 540

Lys Ala Leu Arg Lys Arg Pro Ser Val Tyr Ser Thr Ser Lys Asp Thr
545                 550                 555                 560

Lys Tyr Gln Ser Val Tyr Val Ser Glu Lys Asp Glu Cys Ile Ala Thr
                565                 570                 575

Glu Val (2) INFORMATION FOR SEQ ID NO: 14:

(i) SEQUENCE CHARACTERISTICS:
        (A) LENGTH: 525 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 14:

TACGATGAAY AACCTGGCGA ACTGCCAGCG TGAGAAGGAC ATCTCAGTCA GCATCATCGG      60

GGCYACGTCA GATCARGAAC ACCAACAAGA AGGCGGACTT YMCASCGGGG GACCASAGCG    120

TCCGACAAGA ATGGMTTTCA AGGCCCGCTA CCCCAGCGTG GACTATAACT CGTGCAGGAC    180

CTCAAGGGTG ACGACACCGC CGTCAGGACG TCGCACAGCA AGCGTGACAC CAAGTGCCAG    240

TCCCCAGGCT CCTCAGGGAG GAGAAGGGGA CCCCGACCAC ACTCAGGGGK TGCGTGCTGC    300

GGGCCGGGCT CAGGAGGGGG TACCTGGGGG GTGTCTTCCT GGAACCACTG CTCCGTTTCT    360

CTTCCCAAAT GTTCTCATGC ATTCATTGTG GATTTTCTCT ATTTTCCTTT TAGTGGAGAA    420

GCATCTGAAA GAAAAAGGCC GGACTCGGGC TGTTCAACTT CAAAAGACAC CAAGTACCAG    480

TCGGTGTACG TCATATCCGA GGAGAAGGAC GAGTGCGTCA TCGCA                    525

(2) INFORMATION FOR SEQ ID NO: 15:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: unknown (ii) MOLECULE TYPE: peptide
```

(xi) SEQUENCE DESCRIPTION: SEQ ID NO: 15:

Tyr Asp Glu Xaa Pro Gly Glu Leu Pro Ala
 1               5                  10

(2) INFORMATION FOR SEQ ID NO: 16:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 16:

Glu Gly His Leu Ser Gln His His Arg Gly Xaa Val Arg Ser Xaa Thr
 1               5                  10                  15

Pro Thr Arg Arg Arg Thr Xaa Xaa Arg Gly Thr Xaa Ala Ser Asp Lys
                20                  25                  30

Asn Gly Phe Gln Gly Pro Leu Pro Gln Arg Gly Leu
         35                  40

(2) INFORMATION FOR SEQ ID NO: 17:

(i) SEQUENCE CHARACTERISTICS:
        (A) LENGTH: 118 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 17:

Leu Val Gln Asp Leu Lys Gly Asp Asp Thr Ala Val Arg Thr Ser His
 1               5                  10                  15

Ser Lys Arg Asp Thr Lys Cys Gln Ser Pro Gly Ser Ser Gly Arg Arg
                20                  25                  30

Arg Gly Pro Arg Pro His Ser Gly Xaa Ala Cys Cys Gly Pro Gly Ser
                35                  40                  45

Gly Gly Gly Thr Trp Gly Val Ser Ser Trp His Cys Ser Val Ser Leu
        50                  55                  60

Pro Lys Cys Ser His Ala Phe Ile Val Asp Phe Leu Tyr Phe Pro Phe
65                  70                  75                  80

Ser Gly Glu Ala Ser Glu Arg Lys Arg Pro Asp Ser Gly Cys Ser Thr
                85                  90                  95

Ser Lys Asp Thr Lys Tyr Gln Ser Val Tyr Val Ile Ser Glu Glu Lys
            100                 105                 110

Asp Glu Cys Val Ile Ala
            115

(2) INFORMATION FOR SEQ ID NO: 18:

(i) SEQUENCE CHARACTERISTICS:
        (A) LENGTH: 173 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 18:

Thr Met Asn Asn Leu Ala Asn Cys Gln Arg Glu Lys Asp Ile Ser Val

-continued

```
1               5                   10                  15
Ser Ile Ile Gly Ala Thr Ser Asp Gln Glu His Gln Gln Glu Gly Gly
                20                  25                  30

Leu Xaa Xaa Gly Gly Pro Xaa Pro Thr Arg Met Xaa Phe Lys Ala Arg
            35                  40                  45

Tyr Pro Ser Val Asp Tyr Asn Ser Cys Arg Thr Ser Arg Val Thr Thr
        50                  55                  60

Pro Pro Ser Gly Arg Arg Thr Ala Ser Val Thr Pro Ser Ala Ser Pro
 65                 70                  75                  80

Gln Ala Pro Gln Gly Gly Glu Gly Asp Pro Asp His Thr Gln Gly Xaa
                85                  90                  95

Arg Ala Ala Gly Arg Ala Gln Glu Gly Val Pro Gly Gly Cys Leu Pro
            100                 105                 110

Gly Thr Thr Ala Pro Phe Leu Phe Pro Asn Val Leu Met His Ser Leu
            115                 120                 125

Trp Ile Phe Ser Ile Phe Leu Leu Val Glu Lys His Leu Lys Glu Lys
        130                 135                 140

Gly Arg Thr Arg Ala Val Gln Leu Gln Lys Thr Pro Ser Thr Ser Arg
145                 150                 155                 160

Cys Thr Ser Tyr Pro Arg Arg Thr Ser Ala Ser Ser
                165                 170
```

(2) INFORMATION FOR SEQ ID NO: 19:

(i) SEQUENCE CHARACTERISTICS:
        (A) LENGTH: 60 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 19:

```
Xaa Thr Trp Arg Thr Ala Ser Val Arg Arg Thr Ser Gln Ser Ala Ser
 1               5                  10                  15

Ser Gly Xaa Arg Gln Ile Xaa Asn Thr Asn Lys Lys Ala Asp Phe Xaa
            20                  25                  30

Xaa Gly Asp Xaa Ser Val Arg Gln Glu Trp Xaa Ser Arg Pro Ala Thr
        35                  40                  45

Pro Ala Trp Thr Ile Thr Arg Ala Gly Pro Gln Gly
 50                 55                  60
```

(2) INFORMATION FOR SEQ ID NO: 20:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 20:

```
Arg His Arg Arg Gln Asp Val Ala Gln Gln Ala
 1               5                  10
```

(2) INFORMATION FOR SEQ ID NO: 21:

(i) SEQUENCE CHARACTERISTICS:
        (A) LENGTH: 61 amino acids
        (B) TYPE: amino acid

```
        (C) STRANDEDNESS: <Unknown>
        (D) TOPOLOGY: unknown (ii) MOLECULE TYPE: peptide (xi) SEQUENCE DESCRIPTION: SEQ ID NO: 21:

His Gln Val Pro Val Pro Arg Leu Leu Arg Glu Glu Lys Gly Thr Pro
 1               5                  10                  15

Thr Thr Leu Arg Gly Cys Val Leu Arg Ala Gly Leu Arg Arg Gly Tyr
            20                  25                  30

Leu Gly Gly Val Phe Leu Glu Pro Leu Leu Arg Phe Ser Ser Gln Met
        35                  40                  45

Phe Ser Cys Ile His Cys Gly Phe Ser Leu Phe Ser Phe
 50                  55                  60

(2) INFORMATION FOR SEQ ID NO: 22:

(i) SEQUENCE CHARACTERISTICS:
        (A) LENGTH: 33 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 22:

Lys Lys Lys Ala Gly Leu Gly Leu Phe Asn Phe Lys Lys Arg His Gln
 1               5                  10                  15

Val Pro Val Gly Val Arg His Ile Arg Gly Glu Gly Arg Val Arg His
            20                  25                  30

Arg (2) INFORMATION FOR SEQ ID NO: 23:

(i) SEQUENCE CHARACTERISTICS:
        (A) LENGTH: 175 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 23:

Thr Met Asn Asn Leu Ala Asn Cys Gln Arg Glu Lys Asp Ile Ser Val
 1               5                  10                  15

Ser Ile Ile Gly Ala Thr Gly Ile Xaa Asn Thr Asn Lys Lys Ala Asp
            20                  25                  30

Phe Xaa Xaa Gly Asp Xaa Ser Ser Asp Lys Asn Gly Phe Gln Lys Ala
        35                  40                  45

Arg Tyr Pro Ser Val Asp Tyr Asn Leu Val Gln Asp Leu Lys Gly Asp
 50                  55                  60

Asp Thr Ala Val Arg Thr Ser His Ser Lys Arg Asp Thr Lys Cys Gln
 65                  70                  75                  80

Ser Pro Gly Ser Ser Gly Arg Arg Arg Gly Pro Arg Pro His Ser Gly
                 85                  90                  95

Xaa Ala Cys Cys Gly Pro Gly Ser Gly Gly Thr Trp Gly Val Ser
                100                 105                 110

Ser Trp Asn His Cys Ser Val Ser Leu Pro Lys Cys Ser His Ala Phe
            115                 120                 125

Ile Val Asp Phe Leu Tyr Phe Pro Phe Ser Gly Glu Ala Ser Glu Arg
130                 135                 140
```

```
Lys Arg Pro Asp Ser Gly Cys Ser Thr Ser Lys Asp Thr Lys Tyr Gln
145                 150                 155                 160

Ser Val Tyr Val Ile Ser Glu Glu Lys Asp Glu Cys Val Ile Ala
                165                 170                 175

(2) INFORMATION FOR SEQ ID NO: 24:

(i) SEQUENCE CHARACTERISTICS:
        (A) LENGTH: 2899 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 24:

GTCCAGCGGT ACCATGGGCC GTCGGAGCGC GCTACCCCTT GCCGTGGTCT CTGCCCTGCT        60

GTGCCAGGTC TGGAGCTCCG GCGTATTTGA GCTGAAGCTG CAGGAGTTCG TCAACAAGAA       120

GGGGCTGCTG GGAACCGCA ACTGCTGCCG CGGGGGCTCT GGCCCGCCTT GCGCCTGCAG        180

GACCTTCTTT CGCGTATGCC TCAACCACTA CCAGGCCAGC GTGTCACCGG AGCCACCCTG       240

CACCTACGGC AGTGCTGTCA CGCCAGTGCT GGGTCTCGAC TCCTTCAGCC TGCCTSATKG       300

SGYASGSRYC SMCCYCGAGG YCKWCRGYAW CSMYAAGYYY GATATCGMMY TYCGGCTTCA       360

CCTGGCCRGG YACCTTCTCT CTGATYATTG AAGCYCTCCA YACAGAYTCT CCYGATGACC       420

TCGCAACAGA AAACCCAGAA AGACTCATCA GCCGCCTGRC CACYCAGAGG CACCTSACKG       480

TGGGMGARGA RTGGTCYCAG GACCTKCACA GYAGCGGCCG CACRGACCTC MRGTACTCYT       540

ACCGSTTYGT GTGTGACGAR CACTACTACG GAGARGGYTG CTCTGTKTTC TGCCGWCCYC       600

GGGAYGAYGC CTTYGGCCAC TTCACCTGYG GGGASMGWGG GGAGAARRTG TGCRACCCTG       660

GCTGGAAAGG SCMGTACTGC ACWGASCCRA TCTGYCTGCC WGGRTGTGAT GASCARCATG       720

GATWYTGTGA CAAACCAGGG GARTGCAAGT GCAGAGTKGG CTGGCAGGGC CGSTACTGYG       780

ATGAGTGYAT CCGYTAYCCA GGYTGTCTCC ATGGCACCTG CCAGCARCCC TGGCAGTGYA       840

ACTGCCAGGA AGGNTGGGGG GGCCTTTTCT GCAACCARGA CCTGAACTAC TGYACWCACC       900

ATAAGCCSTG CARGAATGGA GCCACCTGCA ACMAACACGG GCCAGGGGGA GCTACACWTG       960

KTCYTTGGCC GGNCYKGGGT AYANAGGGTG CCAMCTGYGA AGCTTGGGRA KTRGAYGAGT      1020

TGTTGMYCCY AGCCCYTGGY AAGAACGGAG SGAGCTKSAC GGAYCTTCGG AGRACAGCTW      1080

CTCYTGYACC TGCCCWCCCG GCTTCTAYGG CAARRTCTGT GARYTGAGYG CCATGACCTG      1140

TGCRGAYGGC CCTTGCTTYA AYGGRGGWCG RTGYTCAGAY ARCCCYGAYG GAGGSTACAS      1200

CTGCCRYTGC CCCKTGGGCT WCTCYGGCTT CAACTGTGAG AAGAARATKG AYYWCTGCRG      1260

CTCTTCMCCY TGTTCTAAYG GTGCCAAGTG TGTGGACCTC GGYRAYKCYT ACCTGTGCCG      1320

STGCCAGGCY GGCTTCTCSG GGAGGYACTG YGASGACAAY GTGGAYGACT GYGCCTCCTC      1380

CCCGTGYGCM AAYGGGGGCA CCTGCCGGGA YRGYGTGAAC GACTTGTCCT GYACCTGCCC      1440

RCCTGGCTAC ACGGGCARGA ACTGCAGYGC CCCYGYCAGC AGGTGYGAGC AYGCACCCTG      1500

CCAYAATGGG GCCACCTGCC ACSAGAGGGG CCASCGCTAY WTGTGYGAGT GYGCCCRRRG      1560

CTAYGGSGGY CCCAACTGCC ANTTYCTGCT CCCYGAARCY GMCCMCCMGG SCCCAYGGTG      1620

GTGGAAMCTC MSYKARARRM AYMTARRAGR GCCRGGGSGG GCCCWTCCCC TKGGTGGYCG      1680

TGTGYGCCGG GGTSRTSCTT GTCCTCMTGC TGCTGCTGGG CTGTGCYGCT GTGGTGGTCT      1740

GCGTCCGGCT GARGCTRCAG AARCACCRGC CYCCASCYGA MCCCTGNSGG GGRGAGACRG      1800
```

```
ARACCATGAA CAACCTRGNC AAYTGCCAGC GYGAGAAGGA CRTYTCWGTY AGCATCATYG      1860

GGGNYACSCA CATCAAGAAC ACCAACAAGA AGGCGGACTT YCACGGGAC CAYRGNGCCR      1920

ASAAGARYRG CTTYAAGGYC CGMTACCCMR NKGTGGACTA TAACCTCGTK CRRGACCTCA     1980

AGGGWGAYGA MRCCRCSGTC AGGGAYRCRC ACAGCAARCG TGACACCAAG TGNCAGYCMC     2040

AGRGCTCYKG AGGRGARGAG AAGGGGAYCS CCGACCMACA CTYAGGGGGT GGAGGAAGMW     2100

TCYTGAMAGA AAAAGGCCRG ASTYYGGGYY TRYTCWACTT TCAAARGACA ANCMANGTAC     2160

MAGTCGGTGT NYGTYMTKTC YGNAGRAGGA AGGNTGASTG YGTYATAGGM RNYTGAGGTN     2220

GTAARNTGGN AGCGATGTGG CAANNTTCCC ATTTCTCKSA AAKNNNATTC CMMGGATATA     2280

GCYCCGNTGA ATGCTKCTGA GAGAGGAAGG GAGAGGAAAC CCAGGGACTG YTKYTCAGAA     2340

CCAGGTTCAG GCGAAGCTGG TTCTCTCAGA GTTAGCAGAG GCGCCCGACA CTGCCAGCCT     2400

AGGCTTTGGC TGCCGCTGGA CTGCCTGCTG GTTGTTCCCA TTGCACTATG GACAGTTGCT     2460

TTGAAGAGTA TATATTTAAA TGGACGAGTG ACTTGATTCA TATACGAAGC ACGCACTGCC     2520

CACACGTCTA TCTTGGATTA CTATGAGCCA GTCTTTCCTT GAACTAGAAA CACAACTGCC     2580

TTTATTGTCC TTTTTGATAC TGAGATGTGT TTTTTTTTTT CCTAGACGGG AAAAAGAAAA     2640

CGTGTGTTAT TTTTTTGGGA TTTGTAAAAA TATTTTTCAT GATATCTGTA AAGCTTGAGT     2700

ATTTTGTGAC GTTCATTTTT TTATAATTTA AATTTTGGTA AATATGTACA AAGGCACTTC     2760

GGGTCTATGT GACTATATTT TTTTGTATAT AAATGTATTT ATGGAATATT GTGCAAATGT     2820

TATTTGAGTT TTTTACTGTT TTGTTAATGA AGAAATTCAT TTTAAAAATA TTTTTCCAAA     2880

ATAAATATAA TGAACTACA                                                 2899

(2) INFORMATION FOR SEQ ID NO: 25:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 25:

Glu Lys Asp Glu Cys Val Ile Ala
  1               5

(2) INFORMATION FOR SEQ ID NO: 26:

(i) SEQUENCE CHARACTERISTICS:
        (A) LENGTH: 1981 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 26:

CATTGGGTAC GGGCCCCCCT CGAGGTCGAC GGTATCGATA AGCTTGATAT CGAATTCCGG       60

CTTCACCTGG CCGGGCACCT TCTCTCTGAT TATTGAAGCT CTCCACACAG ATTCTCCTGA      120

TGACCTCGCA ACAGAAAACC CAGAAAGACT CATCAGCCGC CTGGCCACCC AGAGGCACCT     180

GACGGTGGGC GAGGAGTGGT CCCAGGACCT GCACAGCAGC GGCCGCACGG ACCTCAAGTA     240

CTCCTACCGC TTCGTGTGTG ACGAACACTA CTACGGAGAG GGCTGCTCCG TTTTCTGCCG     300

TCCCCGGGAC GATGCCTTCG GCCACTTCAC CTGTGGGGAG CGTGGGGAGA AAGTGTGCAA     360
```

-continued

```
CCCTGGCTGG AAAGGGCCCT ACTGCACAGA GCCGATCTGC CTGCCTGGAT GTGATGAGCA     420

GCATGGATTT TGTGACAAAC CAGGGGAATG CAAGTGCAGA GTGGGCTGGC AGGGCCGGTA     480

CTGTGACGAG TGTATCCGCT ATCCAGGCTG TCTCCATGGC ACCTGCCAGC AGCCCTGGCA     540

GTGCAACTGC CAGGAAGGNT GGGGGGGCCT TTTCTGCAAC CAGGACCTGA ACTACTGCAC     600

ACACCATAAG CCCTGCAAGA ATGGAGCCAC CTGCAACAAA CACGGGCCAG GGGAGCTAC     660

ACTTGGTCTT TGGCCGGNCT GGGGTACANA GGGTGCCACC TGCGAAGCTT GGGGATTGGA     720

CGAGTTGTTG ACCCCAGCCC TTGGTAAGAA CGGAGGGAGC TTGACGGATC TTCGGAGAAC     780

AGCTACTCCT GTACCTGCCC ACCCGGCTTC TACGGCAAAA TCTGTGAATT GAGTGCCATG     840

ACCTGTGCGG ACGGCCCTTG CTTTAACGGG GGTCGGTGCT CAGACAGCCC CGATGGAGGG     900

TACAGCTGCC GCTGCCCCGT GGGCTACTCC GGCTTCAACT GTGAGAAGAA AATTGACTAC     960

TGCAGCTCTT CACCCTGTTC TAATGGTGCC AAGTGTGTGG ACCTCGGTGA TGCCTACCTG    1020

TGCCGCTGCC AGGCCGGCTT CTCGGGGAGG CACTGTGACG ACAACGTGGA CGACTGCGCC    1080

TCCTCCCCGT GCGCCAACGG GGGCACCTGC CGGGATGGCG TGAACGACTT CTCCTGCACC    1140

TGCCCGCCTG GCTACACGGG CAGGAACTGC AGTGCCCCCG CCAGCAGGTG CGAGCACGCA    1200

CCCTGCCACA ATGGGGCCAC CTGCCACGAG AGGGGCCACC GCTATTTGTG CGAGTGTGCC    1260

CGAAGCTACG GGGTCCCAA CTGCCANTTC CTGCTCCCCG AAACTGCCCC CCCGGCCCCA    1320

CGGTGGTGGA AACTCCCCTA AAAAAACCTA AAAGGGCCGG GGGGGGCCCA TCCCCTTGGT    1380

GGACGTGTGC GCCGGGGTCA TCCTTGTCCT CATGCTGCTG CTGGGCTGTG CCGCTGTGGT    1440

GGTCTGCGTC CGGCTGAGGC TGCAGAAGCA CCGGCCCCCA GCCGACCCCT GNCGGGGGA    1500

GACGGAGACC ATGAACAACC TGGNCAACTG CCAGCGTGAG AAGGACATCT CAGTCAGCAT    1560

CATCGGGGNC ACGCAGATCA AGAACACCAA CAAGAAGGCG GACTTCCACG GGACCACAG     1620

NGCCGACAAG AATGGCTTCA AGGCCCGCTA CCCAGNGGTG GACTATAACC TCGTGCAGGA    1680

CCTCAAGGGT GACGACACCG CCGTCAGGGA CGCGCACAGC AAGCGTGACA CCAAGTGNCA    1740

GCCCCAGGGC TCCTCAGGGG AGGAGAAGGG GACCCCCGAC CCACACTCAG GGGTGGAGG     1800

AAGCATCTTG AAAGAAAAAG GCCGGACTTC GGGCTTGTTC AACTTTCAAA AGACAANCAA    1860

NGTACAAGTC GGTGTNCGTC ATTTCCGNAG GAGGAAGGNT GACTGCGTCA TAGGAANTTG    1920

AGGTNGTAAA NTGGNAGTTG ANNTTGGAAA GNNNTCCCCG GATTCCGNTT TCAAAGTTTT    1980

T                                                                   1981
```

(2) INFORMATION FOR SEQ ID NO: 27:

(i) SEQUENCE CHARACTERISTICS:
        (A) LENGTH: 31 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 27:

```
His Trp Val Arg Ala Pro Leu Glu Val Asp Gly Ile Asp Lys Leu Asp
  1               5                  10                  15

Ile Glu Phe Arg Leu His Leu Ala Gly His Leu Leu Ser Asp Tyr
             20                  25                  30
```

(2) INFORMATION FOR SEQ ID NO: 28:

-continued

```
    (i) SEQUENCE CHARACTERISTICS:
        (A) LENGTH: 7 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 28:

Ser Ser Pro His Arg Phe Ser
1               5

(2) INFORMATION FOR SEQ ID NO: 29:

(i) SEQUENCE CHARACTERISTICS:
        (A) LENGTH: 45 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 29:

Pro Arg Asn Arg Lys Pro Arg Lys Thr His Gln Pro Pro Gly His Pro
1               5                   10                  15

Glu Ala Pro Asp Gly Gly Arg Gly Val Val Pro Gly Pro Ala Gln Gln
            20                  25                  30

Arg Pro His Gly Pro Gln Val Leu Leu Pro Leu Arg Val
        35                  40                  45

(2) INFORMATION FOR SEQ ID NO: 30:

(i) SEQUENCE CHARACTERISTICS:
        (A) LENGTH: 49 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 30:

Arg Thr Leu Leu Arg Arg Gly Leu Leu Arg Phe Pro Ser Pro Gly Arg
1               5                   10                  15

Cys Leu Arg Pro Leu His Leu Trp Gly Ala Trp Gly Glu Ser Val Gln
            20                  25                  30

Pro Trp Leu Glu Arg Ala Leu Leu His Arg Ala Asp Leu Pro Ala Trp
        35                  40                  45

Met (2) INFORMATION FOR SEQ ID NO: 31:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 31:

Ala Ala Trp Ile Leu
1               5

(2) INFORMATION FOR SEQ ID NO: 32:

(i) SEQUENCE CHARACTERISTICS:
```

(A) LENGTH: 16 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 32:

Gln Thr Arg Gly Met Gln Val Gln Ser Gly Leu Ala Gly Pro Val Leu
1               5                  10                  15

(2) INFORMATION FOR SEQ ID NO: 33:

(i) SEQUENCE CHARACTERISTICS:
        (A) LENGTH: 40 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 33:

Arg Val Tyr Pro Leu Ser Arg Leu Ser Pro Trp His Leu Pro Ala Ala
1               5                  10                  15

Leu Ala Val Gln Leu Pro Gly Arg Xaa Gly Gly Pro Phe Leu Gln Pro
            20                  25                  30

Gly Pro Glu Leu Leu His Thr Pro
            35                  40

(2) INFORMATION FOR SEQ ID NO: 34:

(i) SEQUENCE CHARACTERISTICS:
        (A) LENGTH: 45 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 34:

Ala Leu Gln Glu Trp Ser His Leu Gln Gln Thr Arg Ala Arg Gly Ser
1               5                  10                  15

Tyr Thr Trp Ser Leu Ala Gly Leu Gly Tyr Xaa Gly Cys His Leu Arg
            20                  25                  30

Ser Leu Gly Ile Gly Arg Val Val Asp Pro Ser Pro Trp
            35                  40                  45

(2) INFORMATION FOR SEQ ID NO: 35:

(i) SEQUENCE CHARACTERISTICS:
        (A) LENGTH: 196 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 35:

Glu Arg Arg Glu Leu Asp Gly Ser Ser Glu Asn Ser Tyr Ser Cys Thr
1               5                  10                  15

Cys Pro Pro Gly Phe Tyr Gly Lys Ile Cys Glu Leu Ser Ala Met Thr
            20                  25                  30

Cys Ala Asp Gly Pro Cys Phe Asn Gly Gly Arg Cys Ser Asp Pro Asp
            35                  40                  45

Gly Gly Tyr Ser Cys Arg Cys Pro Val Gly Tyr Ser Gly Phe Asn Cys

-continued

```
             50                  55                  60
Glu Lys Lys Ile Asp Tyr Cys Ser Ser Ser Pro Cys Ser Asn Gly Ala
 65                  70                  75                  80

Lys Cys Val Asp Leu Gly Asp Ala Tyr Leu Cys Arg Gly Gln Ala Gly
                 85                  90                  95

Phe Ser Gly Arg His Cys Asp Asp Asn Val Asp Asp Cys Ala Ser Ser
                100                 105                 110

Pro Cys Ala Asn Gly Gly Thr Cys Arg Asp Gly Val Asn Asp Phe Ser
                115                 120                 125

Cys Thr Cys Pro Pro Gly Tyr Thr Gly Arg Asn Cys Ser Ala Pro Ala
130                 135                 140

Ser Arg Cys Glu His Ala Pro Cys His Asn Gly Ala Thr Cys His Glu
145                 150                 155                 160

Arg Gly His Arg Tyr Xaa Cys Glu Cys Ala Arg Ser Tyr Gly Gly Pro
                165                 170                 175

Asn Cys Xaa Phe Leu Leu Pro Glu Thr Ala Pro Ala Pro Arg Trp
                180                 185                 190

Trp Lys Leu Pro
        195
```

(2) INFORMATION FOR SEQ ID NO: 36:

(i) SEQUENCE CHARACTERISTICS:
        (A) LENGTH: 65 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 36:

```
Lys Asn Leu Lys Gly Pro Gly Gly Ala His Pro Leu Gly Gly Arg Val
 1                   5                  10                  15

Arg Arg Gly His Pro Cys Pro His Ala Ala Gly Leu Cys Arg Cys
                 20                  25                  30

Gly Gly Leu Arg Pro Ala Glu Ala Glu Ala Pro Ala Pro Ser Arg
             35                  40                  45

Pro Leu Xaa Gly Gly Asp Gly Asp His Glu Gln Pro Gly Gln Leu Pro
 50                  55                  60

Ala
 65
```

(2) INFORMATION FOR SEQ ID NO: 37:

(i) SEQUENCE CHARACTERISTICS:
        (A) LENGTH: 42 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 37:

```
Glu Gly His Leu Ser Gln His His Arg Gly His Ala Asp Gln Glu His
 1                   5                  10                  15

Gln Gln Glu Gly Gly Leu Pro Arg Gly Pro Gln Xaa Arg Gln Glu Trp
                 20                  25                  30

Leu Gln Gly Pro Leu Pro Xaa Gly Gly Leu
             35                  40
```

(2) INFORMATION FOR SEQ ID NO: 38:

(i) SEQUENCE CHARACTERISTICS:
       (A) LENGTH: 7 amino acids
       (B) TYPE: amino acid
       (C) STRANDEDNESS: <Unknown>
       (D) TOPOLOGY: unknown (ii) MOLECULE TYPE: peptide (xi) SEQUENCE DESCRIPTION: SEQ ID NO: 38:

Pro Arg Ala Gly Pro Gln Gly
1               5

(2) INFORMATION FOR SEQ ID NO: 39:

(i) SEQUENCE CHARACTERISTICS:
       (A) LENGTH: 11 amino acids
       (B) TYPE: amino acid
       (C) STRANDEDNESS: <Unknown>
       (D) TOPOLOGY: unknown (ii) MOLECULE TYPE: peptide (xi) SEQUENCE DESCRIPTION: SEQ ID NO: 39:

Arg His Arg Arg Gln Gly Arg Ala Gln Gln Ala
1               5                   10

(2) INFORMATION FOR SEQ ID NO: 40:

(i) SEQUENCE CHARACTERISTICS:
       (A) LENGTH: 57 amino acids
       (B) TYPE: amino acid
       (C) STRANDEDNESS: <Unknown>
       (D) TOPOLOGY: unknown (ii) MOLECULE TYPE: peptide (xi) SEQUENCE DESCRIPTION: SEQ ID NO: 40:

His Gln Val Xaa Ala Pro Gly Leu Leu Arg Gly Gly Glu Gly Asp Pro
1               5                   10                  15

Arg Pro Thr Leu Arg Gly Trp Arg Lys His Leu Glu Arg Lys Arg Pro
                20                  25                  30

Asp Phe Gly Leu Val Gln Leu Ser Lys Asp Xaa Gln Xaa Thr Ser Arg
            35                  40                  45

Cys Xaa Ser Phe Pro Xaa Glu Glu Gly
    50                  55

(2) INFORMATION FOR SEQ ID NO: 41:

(i) SEQUENCE CHARACTERISTICS:
       (A) LENGTH: 8 amino acids
       (B) TYPE: amino acid
       (C) STRANDEDNESS: <Unknown>
       (D) TOPOLOGY: unknown (ii) MOLECULE TYPE: peptide (xi) SEQUENCE DESCRIPTION: SEQ ID NO: 41:

Leu Arg His Arg Xaa Leu Arg Xaa
1               5

(2) INFORMATION FOR SEQ ID NO: 42:

(i) SEQUENCE CHARACTERISTICS:
       (A) LENGTH: 13 amino acids

```
         (B) TYPE: amino acid
         (C) STRANDEDNESS: <Unknown>
         (D) TOPOLOGY: unknown (ii) MOLECULE TYPE: peptide (xi) SEQUENCE DESCRIPTION: SEQ ID NO: 42:

Xaa Trp Lys Xaa Xaa Pro Gly Phe Arg Phe Gln Ser Phe
 1               5                  10

(2) INFORMATION FOR SEQ ID NO: 43:

(i) SEQUENCE CHARACTERISTICS:
         (A) LENGTH: 276 amino acids
         (B) TYPE: amino acid
         (C) STRANDEDNESS: <Unknown>
         (D) TOPOLOGY: unknown (ii) MOLECULE TYPE: peptide (xi) SEQUENCE DESCRIPTION: SEQ ID NO: 43:

Ile Gly Tyr Gly Pro Pro Ser Arg Ser Thr Val Ser Ile Ser Leu Ile
 1               5                  10                  15

Ser Asn Ser Gly Phe Thr Trp Pro Gly Thr Phe Ser Leu Ile Ile Glu
                20                  25                  30

Ala Leu His Thr Asp Ser Pro Asp Asp Leu Ala Thr Glu Asn Pro Glu
                35                  40                  45

Arg Leu Ile Ser Arg Leu Ala Thr Gln Arg His Leu Thr Val Gly Glu
         50                  55                  60

Glu Trp Ser Gln Asp Leu His Ser Ser Gly Arg Thr Asp Leu Lys Tyr
 65                  70                  75                  80

Ser Tyr Arg Phe Val Cys Asp Glu His Tyr Tyr Gly Glu Gly Cys Ser
                85                  90                  95

Val Phe Cys Arg Pro Arg Asp Asp Ala Phe Gly His Phe Thr Cys Gly
                100                 105                 110

Glu Arg Gly Glu Lys Val Cys Asn Pro Gly Trp Lys Gly Pro Tyr Cys
            115                 120                 125

Thr Glu Pro Ile Cys Leu Pro Gly Cys Asp Glu Gln His Gly Phe Cys
130                 135                 140

Asp Lys Pro Gly Glu Cys Lys Cys Arg Val Gly Trp Gln Gly Arg Tyr
145                 150                 155                 160

Cys Asp Glu Cys Ile Arg Tyr Pro Gly Cys Leu His Gly Thr Cys Gln
                165                 170                 175

Gln Pro Trp Gln Cys Asn Cys Gln Glu Gly Trp Gly Gly Leu Phe Cys
                180                 185                 190

Asn Gln Asp Leu Asn Tyr Cys Thr His His Lys Pro Cys Lys Asn Gly
            195                 200                 205

Ala Thr Cys Asn Lys His Gly Pro Gly Ala Thr Leu Gly Leu Trp
210                 215                 220

Pro Xaa Trp Gly Thr Xaa Gly Ala Thr Cys Glu Ala Trp Gly Leu Asp
225                 230                 235                 240

Glu Leu Leu Thr Pro Ala Leu Gly Lys Asn Gly Gly Ser Leu Thr Asp
                245                 250                 255

Leu Arg Arg Thr Ala Thr Pro Val Pro Ala His Pro Ala Ser Thr Ala
                260                 265                 270

Lys Ser Val Asn
        275
```

(2) INFORMATION FOR SEQ ID NO: 44:

(i) SEQUENCE CHARACTERISTICS:
        (A) LENGTH: 93 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 44:

```
Pro Val Arg Thr Ala Leu Ala Leu Thr Gly Val Gly Ala Gln Thr Ala
 1               5                  10                  15

Pro Met Glu Gly Thr Ala Ala Ala Pro Trp Ala Thr Pro Ala Ser
                20                  25                  30

Thr Val Arg Arg Lys Leu Thr Thr Ala Ala Leu His Pro Val Leu Met
            35                  40                  45

Val Pro Ser Val Trp Thr Ser Val Met Pro Thr Cys Ala Ala Ala Arg
        50                  55                  60

Pro Ala Ser Arg Gly Gly Thr Val Thr Thr Thr Trp Thr Thr Ala Pro
65                  70                  75                  80

Pro Pro Arg Ala Pro Thr Gly Ala Pro Ala Gly Met Ala
                85                  90
```

(2) INFORMATION FOR SEQ ID NO: 45:

(i) SEQUENCE CHARACTERISTICS:
        (A) LENGTH: 74 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 45:

```
Thr Thr Ser Pro Ala Pro Ala Arg Leu Ala Thr Arg Ala Gly Thr Ala
 1               5                  10                  15

Val Pro Pro Pro Ala Gly Ala Ser Thr His Pro Ala Thr Met Gly Pro
                20                  25                  30

Pro Ala Thr Arg Gly Ala Thr Ala Ile Cys Ala Ser Val Pro Glu Ala
            35                  40                  45

Thr Gly Val Pro Thr Ala Xaa Ser Cys Pro Lys Leu Pro Pro Arg Pro
        50                  55                  60

His Gly Gly Gly Asn Ser Pro Lys Lys Thr
65                  70
```

(2) INFORMATION FOR SEQ ID NO: 46:

(i) SEQUENCE CHARACTERISTICS:
        (A) LENGTH: 187 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 46:

```
Lys Gly Arg Gly Gly Pro Ile Pro Leu Val Asp Val Cys Ala Gly Val
 1               5                  10                  15

Ile Leu Val Leu Met Leu Leu Leu Gly Cys Ala Ala Val Val Val Cys
                20                  25                  30

Val Arg Leu Arg Leu Gln Lys His Arg Pro Pro Ala Asp Pro Xaa Arg
            35                  40                  45
```

```
Gly Glu Thr Glu Thr Met Asn Asn Leu Xaa Asn Cys Gln Arg Glu Lys
 50                  55                  60
Asp Ile Ser Val Ser Ile Ile Gly Xaa Thr Gln Ile Lys Asn Thr Asn
 65                  70                  75                  80
Lys Lys Ala Asp Phe His Gly Asp His Ala Asp Lys Asn Gly Phe Lys
                     85                  90                  95
Ala Arg Tyr Pro Xaa Val Asp Tyr Asn Leu Val Gln Asp Leu Lys Gly
                100                 105                 110
Asp Asp Thr Ala Val Arg Asp Ala His Ser Lys Arg Asp Thr Lys Xaa
                115                 120                 125
Gln Pro Gln Gly Ser Ser Gly Glu Glu Gly Thr Pro Asp Pro His Ser
            130                 135                 140
Gly Gly Gly Gly Ser Ile Leu Lys Glu Lys Gly Arg Thr Ser Gly Leu
145                 150                 155                 160
Phe Asn Phe Gln Lys Thr Xaa Xaa Val Gln Val Gly Val Arg His Phe
                165                 170                 175
Arg Arg Arg Lys Xaa Asp Cys Val Ile Gly Xaa
                180                 185

(2) INFORMATION FOR SEQ ID NO: 47:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 47:

Gly Xaa Lys Xaa Xaa Val Xaa Xaa Gly Lys Xaa Ser Pro Asp Ser Xaa
 1               5                  10                  15
Phe Lys Val Phe
            20

(2) INFORMATION FOR SEQ ID NO: 48:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 48:

Leu Gly Thr Gly Pro Pro Arg Gly Arg Arg Tyr Arg
 1               5                  10

(2) INFORMATION FOR SEQ ID NO: 49:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 49:

Tyr Arg Ile Pro Ala Ser Pro Gly Arg Ala Pro Ser Leu
 1               5                  10
```

(2) INFORMATION FOR SEQ ID NO: 50:

(i) SEQUENCE CHARACTERISTICS:
        (A) LENGTH: 30 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 50:

```
Leu Leu Lys Leu Ser Thr Gln Ile Leu Leu Met Thr Ser Gln Gln Lys
 1               5                  10                  15

Thr Gln Lys Asp Ser Ser Ala Ala Trp Pro Pro Arg Gly Thr
            20                  25                  30
```

(2) INFORMATION FOR SEQ ID NO: 51:

(i) SEQUENCE CHARACTERISTICS:
        (A) LENGTH: 135 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 51:

```
Arg Trp Ala Arg Ser Gly Pro Arg Thr Cys Thr Ala Ala Ala Arg
 1               5                  10                  15

Thr Ser Ser Thr Pro Thr Ala Ser Cys Val Thr Asn Thr Thr Thr Glu
            20                  25                  30

Arg Ala Ala Pro Phe Ser Ala Val Pro Gly Thr Met Pro Ser Ala Thr
                35                  40                  45

Ser Pro Val Cys Ser Val Gly Arg Lys Cys Ala Thr Leu Ala Gly Lys
            50                  55                  60

Gly Pro Thr Ala Gln Ser Arg Ser Ala Cys Leu Asp Val Met Ser Ser
 65                  70                  75                  80

Met Asp Phe Phe Val Thr Asn Gln Asn Ala Ser Ala Glu Trp Ala Gly
                85                  90                  95

Arg Ala Gly Thr Val Thr Ser Val Ser Ala Ile Gln Ala Val Ser Met
               100                 105                 110

Ala Pro Ala Ser Ser Pro Gly Ser Ala Thr Ala Arg Lys Xaa Gly Gly
            115                 120                 125

Ala Phe Ser Ala Thr Arg Thr
            130                 135
```

(2) INFORMATION FOR SEQ ID NO: 52:

(i) SEQUENCE CHARACTERISTICS:
        (A) LENGTH: 46 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 52:

```
Thr Thr Ala His Thr Ile Ser Pro Ala Arg Met Glu Pro Pro Ala Thr
 1               5                  10                  15

Asn Thr Gly Gln Gly Glu Leu His Leu Val Phe Gly Arg Xaa Gly Val
            20                  25                  30

Xaa Arg Val Pro Pro Ala Lys Leu Gly Asp Trp Thr Ser Cys
```

35                  40                  45

(2) INFORMATION FOR SEQ ID NO: 53:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 53:

Pro Gln Pro Leu Val Arg Thr Glu Gln Glu
1               5                   10

(2) INFORMATION FOR SEQ ID NO: 54:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 54:

Arg Ile Phe Gly Glu Gln Leu Leu Leu Tyr Leu Pro Thr Arg Leu Leu
1               5                   10                  15

Arg Gln Asn Leu
            20

(2) INFORMATION FOR SEQ ID NO: 55:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 55:

Ile Glu Cys His Asp Leu Cys Gly Arg Pro Leu Leu
1               5                   10

(2) INFORMATION FOR SEQ ID NO: 56:

(i) SEQUENCE CHARACTERISTICS:
        (A) LENGTH: 25 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 56:

Arg Gly Ser Val Leu Arg Gln Pro Arg Trp Arg Val Gln Leu Pro Leu
1               5                   10                  15

Pro Arg Gly Leu Leu Arg Leu Gln Leu
            20                  25

(2) INFORMATION FOR SEQ ID NO: 57:

(i) SEQUENCE CHARACTERISTICS:
        (A) LENGTH: 8 amino acids
        (B) TYPE: amino acid
        (C) STRANDEDNESS: <Unknown>

```
            (D) TOPOLOGY: unknown (ii) MOLECULE TYPE: peptide (xi) SEQUENCE DESCRIPTION: SEQ ID NO: 57:

Leu Leu Gln Leu Phe Thr Leu Phe
 1               5

(2) INFORMATION FOR SEQ ID NO: 58:

(i) SEQUENCE CHARACTERISTICS:
            (A) LENGTH: 8 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 58:

Trp Cys Gln Val Cys Gly Pro Arg
 1               5

(2) INFORMATION FOR SEQ ID NO: 59:

(i) SEQUENCE CHARACTERISTICS:
            (A) LENGTH: 15 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 59:

Cys Leu Pro Val Pro Leu Pro Gly Arg Leu Leu Gly Glu Ala Leu
 1               5                  10                  15

(2) INFORMATION FOR SEQ ID NO: 60:

(i) SEQUENCE CHARACTERISTICS:
            (A) LENGTH: 131 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 60:

Arg Gln Arg Gly Arg Leu Arg Leu Leu Pro Val Arg Gln Gly His Leu
 1               5                  10                  15

Pro Gly Trp Arg Glu Arg Leu Leu Leu His Leu Pro Ala Trp Leu His
                20                  25                  30

Gly Gln Glu Leu Gln Cys Pro Arg Gln Val Arg Ala Arg Thr Leu
            35                  40                  45

Pro Gln Trp Gly His Leu Pro Arg Glu Gly Pro Pro Leu Phe Val Arg
    50                  55                  60

Val Cys Pro Lys Leu Arg Gly Ser Gln Leu Pro Xaa Pro Ala Pro Arg
65                  70                  75                  80

Asn Cys Pro Pro Gly Pro Thr Val Val Glu Thr Pro Leu Lys Lys Pro
                85                  90                  95

Lys Arg Ala Gly Gly Gly Pro Ser Pro Trp Trp Thr Cys Ala Pro Gly
                100                 105                 110

Ser Ser Leu Ser Ser Cys Cys Cys Trp Ala Val Pro Leu Trp Trp Ser
            115                 120                 125

Ala Ser Gly
```

130

(2) INFORMATION FOR SEQ ID NO: 61:

(i) SEQUENCE CHARACTERISTICS:
       (A) LENGTH: 18 amino acids
       (B) TYPE: amino acid
       (C) STRANDEDNESS: <Unknown>
       (D) TOPOLOGY: unknown (ii) MOLECULE TYPE: peptide (xi) SEQUENCE DESCRIPTION: SEQ ID NO: 61:

Gly Cys Arg Ser Thr Gly Pro Gln Pro Thr Pro Xaa Gly Gly Arg Arg
 1               5                  10                  15

Arg Pro (2) INFORMATION FOR SEQ ID NO: 62:

(i) SEQUENCE CHARACTERISTICS:
       (A) LENGTH: 98 amino acids
       (B) TYPE: amino acid
       (C) STRANDEDNESS: <Unknown>
       (D) TOPOLOGY: unknown (ii) MOLECULE TYPE: peptide (xi) SEQUENCE DESCRIPTION: SEQ ID NO: 62:

Thr Thr Trp Xaa Thr Ala Ser Val Arg Arg Thr Ser Gln Ser Ala Ser
 1               5                  10                  15

Ser Gly Xaa Arg Arg Ser Arg Thr Pro Thr Arg Arg Arg Thr Ser Thr
                20                  25                  30

Gly Thr Thr Xaa Pro Thr Arg Met Ala Ser Arg Pro Ala Thr Gln Xaa
                35                  40                  45

Trp Thr Ile Thr Ser Cys Arg Thr Ser Arg Val Thr Thr Pro Pro Ser
 50                  55                  60

Gly Thr Arg Thr Ala Ser Val Thr Pro Ser Xaa Ser Pro Arg Ala Pro
65                  70                  75                  80

Gln Gly Arg Arg Arg Cys Pro Pro Thr His Thr Gln Gly Val Glu Glu
                85                  90                  95

Ala Ser (2) INFORMATION FOR SEQ ID NO: 63:

(i) SEQUENCE CHARACTERISTICS:
       (A) LENGTH: 33 amino acids
       (B) TYPE: amino acid
       (C) STRANDEDNESS: <Unknown>
       (D) TOPOLOGY: unknown (ii) MOLECULE TYPE: peptide (xi) SEQUENCE DESCRIPTION: SEQ ID NO: 63:

Lys Lys Lys Ala Gly Leu Arg Ala Cys Ser Thr Phe Lys Arg Gln Xaa
 1               5                  10                  15

Xaa Tyr Lys Ser Val Xaa Val Ile Ser Xaa Gly Gly Arg Xaa Thr Ala
                20                  25                  30

Ser (2) INFORMATION FOR SEQ ID NO: 64:

(i) SEQUENCE CHARACTERISTICS:
       (A) LENGTH: 22 amino acids (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 64:

Glu Xaa Glu Val Val Xaa Trp Xaa Leu Xaa Leu Glu Xaa Xaa Pro Arg
 1               5                  10                  15

Ile Pro Xaa Ser Lys Phe
            20

(2) INFORMATION FOR SEQ ID NO: 65:

(i) SEQUENCE CHARACTERISTICS:
        (A) LENGTH: 192 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 65:

Gly Phe Thr Trp Pro Gly Thr Phe Ser Leu Ile Ile Glu Ala Leu His
 1               5                  10                  15

Thr Asp Ser Pro Asp Asp Leu Ala Thr Glu Asn Pro Glu Arg Leu Ile
                20                  25                  30

Ser Arg Leu Ala Thr Gln Arg His Leu Thr Val Gly Glu Glu Trp Ser
            35                  40                  45

Gln Asp Leu His Ser Ser Gly Arg Thr Asp Leu Lys Tyr Ser Tyr Arg
    50                  55                  60

Phe Val Cys Asp Glu His Tyr Tyr Gly Glu Gly Cys Ser Val Phe Cys
65                  70                  75                  80

Arg Pro Arg Asp Asp Ala Phe Gly His Phe Thr Cys Gly Glu Arg Gly
                85                  90                  95

Glu Lys Val Cys Asn Pro Gly Trp Lys Gly Pro Tyr Cys Thr Glu Pro
            100                 105                 110

Ile Cys Leu Pro Gly Cys Asp Glu Gln His Gly Phe Cys Asp Lys Pro
        115                 120                 125

Gly Glu Cys Lys Cys Arg Val Gly Trp Gln Gly Arg Tyr Cys Asp Glu
    130                 135                 140

Cys Ile Arg Tyr Pro Gly Cys Leu His Gly Thr Cys Gln Gln Pro Trp
145                 150                 155                 160

Gln Cys Asn Cys Gln Glu Gly Trp Gly Gly Leu Phe Cys Asn Gln Asp
                165                 170                 175

Leu Asn Tyr Cys Thr His His Lys Pro Cys Lys Asn Gly Ala Thr Cys
            180                 185                 190

(2) INFORMATION FOR SEQ ID NO: 66:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 66:

Thr Asn Thr Gly Gln Gly
 1               5

(2) INFORMATION FOR SEQ ID NO: 67:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 67:

```
Lys Asn Gly Gly Ser Leu Thr Asp Leu
 1               5
```

(2) INFORMATION FOR SEQ ID NO: 68:

(i) SEQUENCE CHARACTERISTICS:
        (A) LENGTH: 157 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 68:

```
Glu Asn Ser Tyr Ser Cys Thr Cys Pro Pro Gly Phe Tyr Gly Lys Ile
 1               5                  10                  15

Cys Glu Leu Ser Ala Met Thr Cys Ala Asp Gly Pro Cys Phe Asn Gly
                20                  25                  30

Gly Arg Cys Ser Asp Ser Pro Asp Gly Tyr Ser Cys Arg Cys Pro
            35                  40                  45

Val Gly Tyr Ser Gly Phe Asn Cys Glu Lys Lys Ile Asp Tyr Cys Ser
 50                  55                  60

Ser Ser Pro Cys Ser Asn Gly Ala Lys Cys Val Asp Leu Gly Asp Ala
 65                  70                  75                  80

Tyr Leu Cys Arg Cys Gln Ala Gly Phe Ser Gly Arg His Cys Asp Asp
                85                  90                  95

Asn Val Asp Asp Cys Ala Ser Ser Pro Cys Ala Asn Gly Gly Thr Cys
                100                 105                 110

Arg Asp Gly Val Asn Asp Phe Ser Cys Thr Cys Pro Pro Gly Tyr Thr
            115                 120                 125

Gly Arg Asn Cys Ser Ala Pro Ala Ser Arg Cys Glu His Ala Pro Cys
            130                 135                 140

His Asn Gly Ala Thr Cys His Glu Arg Gly His Arg Tyr
145                 150                 155
```

(2) INFORMATION FOR SEQ ID NO: 69:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 69:

```
Cys Glu Cys Ala Arg Ser Tyr Gly Gly Pro Asn Cys
 1               5                  10
```

(2) INFORMATION FOR SEQ ID NO: 70:

(i) SEQUENCE CHARACTERISTICS:

(A) LENGTH: 5 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 70:

Phe Leu Leu Pro Glu
 1           5

(2) INFORMATION FOR SEQ ID NO: 71:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 71:

Pro Pro Gly Pro
 1

(2) INFORMATION FOR SEQ ID NO: 72:

(i) SEQUENCE CHARACTERISTICS:
        (A) LENGTH: 25 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 72:

Leu Leu Leu Gly Cys Ala Ala Val Val Cys Val Arg Leu Arg Leu
 1           5                  10                  15

Gln Lys His Arg Pro Pro Ala Asp Pro
            20                  25

(2) INFORMATION FOR SEQ ID NO: 73:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 73:

Arg Gly Glu Thr Glu Thr Met Asn Asn Leu
 1           5                      10

(2) INFORMATION FOR SEQ ID NO: 74:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 74:

Asn Cys Gln Arg Glu Lys Asp Ile Ser Val Ser Ile Ile Gly
 1           5                      10

(2) INFORMATION FOR SEQ ID NO: 75:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 75:

Thr Gln Ile Lys Asn Thr Asn Lys Lys Ala Asp Phe His Gly Asp His
1               5                   10                  15

(2) INFORMATION FOR SEQ ID NO: 76:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 76:

Ala Asp Lys Asn Gly Phe Lys Ala Arg Tyr Pro
1               5                   10

(2) INFORMATION FOR SEQ ID NO: 77:

(i) SEQUENCE CHARACTERISTICS:
        (A) LENGTH: 26 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 77:

Val Asp Tyr Asn Leu Val Gln Asp Leu Lys Gly Asp Asp Thr Ala Val
1               5                   10                  15
Arg Asp Ala His Ser Lys Arg Asp Thr Lys
            20                  25

(2) INFORMATION FOR SEQ ID NO: 78:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 78:

Gln Pro Gln Gly Ser Ser Gly Glu Glu Lys Gly Thr Pro
1               5                   10

(2) INFORMATION FOR SEQ ID NO: 79:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 79:

```
Pro Thr Leu Arg
 1
```

(2) INFORMATION FOR SEQ ID NO: 80:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 80:

```
Arg Lys Arg Pro
 1
```

(2) INFORMATION FOR SEQ ID NO: 81:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Modified Base
        (B) LOCATION: 6
        (D) OTHER INFORMATION: N=Inosine (xi) SEQUENCE DESCRIPTION: SEQ ID NO: 81:

```
TTCGGNTTYA CNTGGCCNGG NAC                                              23
```

(2) INFORMATION FOR SEQ ID NO: 82:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Modified Base
        (B) LOCATION: 3
        (D) OTHER INFORMATION: N=Inosine (xi) SEQUENCE DESCRIPTION: SEQ ID NO: 82:

```
TCNATGCANG TNCCNCCRTT                                                  20
```

(2) INFORMATION FOR SEQ ID NO: 83:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 83:

```
Phe Gly Phe Thr Trp Pro Gly Thr
 1               5
```

(2) INFORMATION FOR SEQ ID NO: 84:

```
        (i) SEQUENCE CHARACTERISTICS:
            (A) LENGTH: 7 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 84:

Asn Gly Gly Thr Cys Ile Asp
  1               5

(2) INFORMATION FOR SEQ ID NO: 85:

(i) SEQUENCE CHARACTERISTICS:
            (A) LENGTH: 12 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 85:

Ser Ile Pro Pro Gly Ser Arg Thr Ser Leu Gly Val
  1               5                  10

(2) INFORMATION FOR SEQ ID NO: 86:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: Modified Base
            (B) LOCATION: 3
            (D) OTHER INFORMATION: N=Inosine (xi) SEQUENCE DESCRIPTION: SEQ ID NO: 86:

GGNTTCACNT GGCCNGGNAC NTT                                              23

(2) INFORMATION FOR SEQ ID NO: 87:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: Modified Base
            (B) LOCATION: 3
            (D) OTHER INFORMATION: N=Inosine (xi) SEQUENCE DESCRIPTION: SEQ ID NO: 87:

GTNCCNCCRT TYTTRCANGG RTT                                              23

(2) INFORMATION FOR SEQ ID NO: 88:

(i) SEQUENCE CHARACTERISTICS:
            (A) LENGTH: 8 amino acids
            (B) TYPE: amino acid
            (C) STRANDEDNESS: <Unknown>
            (D) TOPOLOGY: unknown (ii) MOLECULE TYPE: peptide
```

(xi) SEQUENCE DESCRIPTION: SEQ ID NO: 88:

Asn Pro Cys Lys Asn Gly Gly Thr
1               5

(2) INFORMATION FOR SEQ ID NO: 89:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: Modified Base
            (B) LOCATION: 3
            (D) OTHER INFORMATION: N=Inosine (xi) SEQUENCE DESCRIPTION: SEQ ID NO: 89:

ACNATGAAYA AYCTNGCNAA YTG                                              23

(2) INFORMATION FOR SEQ ID NO: 90:

(i) SEQUENCE CHARACTERISTICS:
            (A) LENGTH: 8 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 90:

Thr Met Asn Asn Leu Ala Asn Cys
1               5

(2) INFORMATION FOR SEQ ID NO: 91:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: Modified Base
            (B) LOCATION: 6
            (D) OTHER INFORMATION: N=Inosine (xi) SEQUENCE DESCRIPTION: SEQ ID NO: 91:

ACRTANACNG AYTGRTAYTT NGT                                              23

(2) INFORMATION FOR SEQ ID NO: 92:

(i) SEQUENCE CHARACTERISTICS:
            (A) LENGTH: 8 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 92:

Thr Lys Tyr Gln Ser Val Tyr Val
1               5

-continued

```
(2) INFORMATION FOR SEQ ID NO: 93:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Modified Base
        (B) LOCATION: 6
        (D) OTHER INFORMATION: N=Inosine (xi) SEQUENCE DESCRIPTION: SEQ ID NO: 93:

GCDATNACRC AYTCRTCYTT YTC                                          23

(2) INFORMATION FOR SEQ ID NO: 94:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 94:

Gly Phe Thr Trp Pro Gly Thr Phe
1               5
```